US009310370B2

(12) United States Patent
Guilford

(10) Patent No.: US 9,310,370 B2
(45) Date of Patent: Apr. 12, 2016

(54) MARKERS FOR DETECTION OF GASTRIC CANCER

(75) Inventor: Parry John Guilford, Dunedin (NZ)

(73) Assignee: Pacific Edge Limited, Dunedin (NZ)

( * ) Notice: Subject to any disclaimer, the term of this patent is extended or adjusted under 35 U.S.C. 154(b) by 140 days.

(21) Appl. No.: 13/320,392

(22) PCT Filed: May 14, 2010

(86) PCT No.: PCT/NZ2010/000089
§ 371 (c)(1), (2), (4) Date: Jan. 17, 2012

(87) PCT Pub. No.: WO2010/131984
PCT Pub. Date: Nov. 18, 2010

(65) Prior Publication Data

US 2012/0135881 A1 May 31, 2012

(30) Foreign Application Priority Data

May 15, 2009 (NZ) ........................................ 577012

(51) Int. Cl.
*C12Q 1/68* (2006.01)
*G01N 33/574* (2006.01)

(52) U.S. Cl.
CPC ........ *G01N 33/57446* (2013.01); *C12Q 1/6886* (2013.01); *C12Q 2600/158* (2013.01)

(58) Field of Classification Search
None
See application file for complete search history.

(56) References Cited

U.S. PATENT DOCUMENTS

2011/0098189 A1* 4/2011 Lapointe et al. .................. 506/9

FOREIGN PATENT DOCUMENTS

AU WO 2009/052567 A1 * 4/2009 ............... C12Q 1/68
WO WO98/44160 A1 * 10/1998 ............... C12Q 1/68
WO WO 2005/044990 A2 * 5/2005

OTHER PUBLICATIONS

Zhou et al in "hZG16, a novel human secreted protein expressed in liver, was down-regulated in hepatocellular carcinoma" (Biochem and Biophy Res Comm, Apr. 13, 2007, vol. 355 No. 3, pp. 679-686).*
Moniaux et al (J Biol chem 2006 vol. 281: pp. 23676-23685).*
Haab & Lizardi in RCA-enhanced protein detection arrays. (Methods Mol Biol 2006 vol. 328: pp. 15-29).*

* cited by examiner

*Primary Examiner* — Catherine S Hibbert
(74) *Attorney, Agent, or Firm* — D. Benjamin Borson; Borson Law Group, PC

(57) ABSTRACT

Early detection of tumors is a major determinant of survival of patients suffering from tumors, including gastric tumors. Members of the GTM gene family can be differentially expressed in gastric tumor tissue, and thus can be used as markers for the detection of gastric and other types of cancer. The present invention provides for novel GTMs for the detection of tumors, including gastric tumors, and in particular human zymogen granule protein 16 (ZG16). The GTMs can be used in isolation or together with other known GTMs to provide for novel signatures to be used in the detection of tumors, including gastric tumors.

13 Claims, 4 Drawing Sheets

| name | symbol | MWG oligo | Unigene mRNA ref sequence | Protein ref sequence | Rank intensity (tumor) | Rank Intensity (non-malignant) |
|---|---|---|---|---|---|---|
| Mucin 5, subtypes A and C | MUC5AC | 30K#B:7561 | NM_017511 | NP_059981 | 404 | 328 |
| Mucin 17, cell surface associated | MUC17 | 30K#C:0346 | NM_001040105 | NP_001035194 | 2043 | 1485 |
| Zymogen granule protein 16 | ZG16 | 30K#C:0156 | NM_152338 | NP_689551 | 3606 | 3249 |
| carcinoembryonic antigen-related cell adhesion molecule 5 | CEACAM5 | 30K#B:5440 | NM_004363 | NP_004354 | 4873 | 7668 |

| name | symbol | MWG oligo | Unigene mRNA ref sequence | Protein ref sequence | Rank intensity (tumor) | Rank Intensity (non-malignant) |
|---|---|---|---|---|---|---|
| Mucin 5, subtypes A and C | MUC5AC | 30K#B: 7561 | NM_017511 | NP_059981 | 404 | 328 |
| Mucin 17, cell surface associated | MUC17 | 30K#C: 0346 | NM_001040105 | NP_001035 194 | 2043 | 1485 |
| Zymogen granule protein 16 | ZG16 | 30K#C: 0156 | NM_152338 | NP_689551 | 3606 | 3249 |
| carcinoembryonic antigen-related cell adhesion molecule 5 | CEACAM5 | 30K#B: 5440 | NM_004363 | NP_004354 | 4873 | 7668 |

Figure 1

| **Gastric cancer patients** | | **Controls** | |
|---|---|---|---|
| Stage T1 | 2 | Colorectal cancer Stage T2 | 1 |
| Stage T2 | 15 | Colorectal cancer Stage T3 | 9 |
| Stage T3 | 13 | Colorectal cancer Stage T4 | 1 |
| Stage T4 | 1 | Colorectal cancer Post-surgery | 7 |
| Gastrointestinal stromal tumours | 2 | Non-malignant disease | 10 |
| | | Healthy | 13 |
| **TOTAL** | **33** | **TOTAL** | **41** |

SEQUENCE LISTING

<160> NUMBER OF SEQ ID NOS: 11

<210> SEQ ID NO 1
<211> LENGTH: 21
<212> TYPE: DNA
<213> ORGANISM: Human

<400> SEQUENCE: 1
gaggtggtca gcagcattga c 21

<210> SEQ ID NO 2
<211> LENGTH: 23
<212> TYPE: DNA
<213> ORGANISM: Human

<400> SEQUENCE: 2
cctgggaaga gtggtttttt agc 23

<210> SEQ ID NO 3
<211> LENGTH: 23
<212> TYPE: DNA
<213> ORGANISM: Human

<400> SEQUENCE: 3
caccaatgcc attcaggcca ggt 23

<210> SEQ ID NO 4
<211> LENGTH: 19
<212> TYPE: DNA
<213> ORGANISM: Human

<400> SEQUENCE: 4
tcagcatctg ctgcagcta 19

<210> SEQ ID NO 5
<211> LENGTH: 25
<212> TYPE: DNA
<213> ORGANISM: Human

<400> SEQUENCE: 5
cctggtgctc aaatttcagt tctgc 25

<210> SEQ ID NO 6
<211> LENGTH: 18750
<212> TYPE: DNA
<213> ORGANISM: Human

<400> SEQUENCE: 6
atgtcgctgc agttcaatgg gtttgtgcgt tgtgatcaca cggtcctgcc cacagagctg 60

-continued

```
aatgggctat tggggtttcc ttggaggctg ctgagggaca gggcactctt ccccgccgtc    120
cacacaatga gtgttggccg gaggaagctg gccctgctct gggccctggc tctcgctctg    180
gcctgcaccc ggcacacagg ccatgcccag gatggctcct ccgaatccag ctacaagcac    240
caccctgccc tctctcctat cgcccggggg cccagcgggg tcccgctccg tggggcgact    300
gtcttcccat ctctgaggac catccctgtg gtacgagcct ccaacccggc gcacaacggg    360
cgggtgtgca gcacctgggg cagcttccac tacaagacct tcgacggcga cgtcttccgc    420
ttccccggcc tctgcaacta cgtgttctcc gagcactgcg gtgccgccta cgaggatttt    480
aacatccagc tacgccgcag ccaggagtca gcggccccca cgctgagcag ggtcctcatg    540
aaggtggatg gcgtggtcat ccagctgacc aagggctccg tcctggtcaa cggccacccg    600
gtcctgctgc ccttcagcca gtctggggtc ctcattcagc agagcagcag ctacaccaag    660
gtggaggcca ggctgggcct tgtcctcatg tggaaccacg atgacagcct gctgctggag    720
ctggacacca aatacgccaa caagacctgt gggctctgtg gggacttcaa cgggatgccc    780
gtggtcagcg agctcctctc ccacaacacc aagctgacac ccatggaatt cgggaacctg    840
cagaagatgg acgaccccac ggagcagtgt caggaccctg tccctgaacc cccgaggaac    900
tgctccactg gctttggcat ctgtgaggag ctcctgcacg gccagctgtt ctctggctgc    960
gtggccctgg tggacgtcgg cagctacctg gaggcttgca ggcaagacct ctgcttctgt   1020
gaagacaccg acctgctcag ctgcgtctgc cacacccttg ccgagtactc ccggcagtgc   1080
acccatgcag gggggttgcc ccaggactgg cggggccctg acttctgccc ccagaagtgc   1140
cccaacaaca tgcagtacca cgagtgccgc tccccctgcg cagacacctg ctccaaccag   1200
gagcactccc gggcctgtga ggaccactgt gtggccggct gcttctgccc tgaggggacg   1260
gtgcttgacg acatcggcca gaccggctgt gtccctgtgt caaagtgtgc ctgcgtctac   1320
aacggggctg cctatgcccc agggggccacc tactccacag actgcaccaa ctgcacctgc   1380
tccggaggcc ggtggagctg ccaggaggtt ccatgcccgg gtacctgctc tgtgcttgga   1440
ggtgcccact tctcaacgtt tgacgggaag caatacacgg tgcacggcga ctgcagctat   1500
gtgctgacca agccctgtga cagcagtgcc ttcactgtac tggctgagct gcgcaggtgc   1560
gggctgacgg acagcgagac ctgcctgaag agcgtgacac tgagcctgga tggggcgcag   1620
acggtggtgg tgatcaaggc cagtggggaa gtgttcctga accagatcta cacccagctg   1680
cccatctctg cagccaacgt caccatcttc agaccctcaa ccttcttcat catcgcccag   1740
accagcctgg gcctgcagct gaacctgcag ctggtgccca ccatgcagct gttcatgcag   1800
ctggcgccca agctccgtgg gcagacctgc ggtctctgtg ggaacttcaa cagcatccag   1860
gccgatgact tccggaccct cagtggggtg gtggaggcca ccgctgcggc cttcttcaac   1920
accttcaaga cccaggccgc ctgccccaac atcaggaaca gcttcgagga cccctgctct   1980
ctgagcgtgg agaatgcccc caggatgggt gccccgagcg cgtgccggac gctggtgttg   2040
gctctggcgg ccatgctcgt ggtgccgcag gcagagaccc agggccctgt ggagccgagc   2100
tgggagaatg cagggcacac catggatggc ggtgccccga cgtcctcgcc cacccggcgc   2160
gtgagctttg ttccacccgt cactgtcttc cccagcctga gccgtaagca gatgctgccc   2220
ctgccagccg ggaagggggt gtttgccagt cccaaaggtg ggggcccaga tctaggggtg   2280
cagctgccac cagccctgaa cccggcgcac aatgggcggg tgtgcagcac ctggggtgac   2340
ttccactaca agaccttcga cggcgacgtc ttccgcttcc ctggcctttg caactacgtg   2400
```

-continued

```
ttctctgagc actgccgcgc cgcctacgag gacttcaacg tccagctacg ccgaggccta   2460
gtgggctcca ggcctgtggt cacccgtgtt gtcatcaagg cccaggggct ggtgctggag   2520
gcgtccaacg gctccgtcct catcaatggg cagcgggagg agctgcctta cagccgcact   2580
ggcctcctgg tggagcagag cggggactac atcaaggtca gcatccggct ggtgctgaca   2640
ttcctgtgga acggagagga cagtgccctg ctggagctgg atcccaaata cgccaaccag   2700
acctgtggcc tgtgtgggga cttcaacggc ctcccggcct tcaacgagtt ctatgcccac   2760
aacgccaggc tgaccccgct ccagtttggg aacctgcaga agttggatgg gcccacggag   2820
cagtgcccgg acccgctgcc cttgccggcc ggcaactgca cggacgagga gggcatctgc   2880
caccgcaccc tgctggggcc ggcctttgcg gagtgccacg cactggtgga cagcactgcg   2940
tacctggccg cctgcgccca ggacctgtgc cgctgcccca cctgcccgtg tgccaccttt   3000
gtggaatact cacgccagtg cgcccacgcg gggggccagc cgcggaactg gaggtgccct   3060
gagctctgcc cccggacctg ccccctcaac atgcagcacc aggagtgtgg ctcaccctgc   3120
acggacacct gctccaaccc ccagcgcgcg cagctctgcg aggaccactg tgtggacggc   3180
tgcttctgcc ccccaggcag gtcttgcacg gtgctggatg acatcacgca ctctggctgc   3240
ctgcccctcg ggcagtgccc ctgcacccac ggcggccgca cctacagccc gggcacctcc   3300
ttcaacacca cctgcagctc ctgcacctgc tccgggggc tatggcagtg ccaggacctg   3360
ccgtgccctg gcacctgctc tgtgcagggc ggggcccaca tctccaccta tgatgagaaa   3420
ctctacgacc tgcatggtga ctgcagctac gttctgtcca agaaatgtgc cgacagcagc   3480
ttcaccgtgc tggctgagct gcggaagtgc ggcctgacgg acaacgagaa ctgcctgaaa   3540
gcggtgacgc tcagcctgga cggcggggac acggccatcc gggtccaagc ggacggcggc   3600
gtgttcctca actccatcta cacgcagctg cccctgtcgg cagccaacat caccctgttc   3660
acaccctcga gcttcttcat cgtggtgcag acaggcctcg ggctgcagct gctggtgcag   3720
ctggtgccac tcatgcaggt gtttgtcagg ctggaccccg cccaccaggg ccagatgtgc   3780
ggcctgtgtg ggaacttcaa ccagaaccag gctgacgact tcacggccct cagcggggtg   3840
gtggaggcca cgggcgcagc cttcgccaac acctggaagg cccaggctgc ctgtgccaat   3900
gccaggaaca gctttgagga cccctgctcc ctcagtgtgg agaatgagaa ctacgcccgg   3960
cactggtgct cgcgcctgac cgatcccaac agtgccttct cgcgctgcca ctccatcatc   4020
aaccccaagc ccttccactc gaactgcatg tttgacacct gcaactgtga gcggagcgag   4080
gactgcctgt gcgccgcgct gtcctcctac gtgcacgcct gtgccgccaa gggcgtacag   4140
ctcagcgact ggagggacgg cgtctgcacc aagtacatgc agaactgccc caagtcccag   4200
cgctacgcct acgtggtgga tgcctgccag cccacttgcc gcggcctgag tgaggccgac   4260
gtcacctgca gcgtttcctt cgtgcctgtg gacggctgca cctgccccgc gggcaccttc   4320
ctcaatgacg cgggcgcctg tgtgcccgcc caggagtgcc cctgctacgc tcacggcacc   4380
gtgctggctc ctggagaggt ggtgcacgac gagggcgccg tgtgttcatg tacgggtggg   4440
aagctaagct gcctgggagc ctctctgcag aaaagcacag ggtgtgcagc ccccatggtg   4500
tacctggact gcagcaacag ctcggcgggc acccctgggg ccgagtgcct ccggagctgc   4560
cacacgctgg acgtgggctg tttcagcaca cactgcgtgt ccggctgtgt ctgtcccccg   4620
gggctggtgt cggatgggag tgggggctgc attgccgagg aggactgccc ctgtgtgcac   4680
aacgaggcca cctacaagcc tggagagacc atcagggtcg actgcaacac ctgcacctgc   4740
aggaaccgga ggtgggagtg cagccaccgg ctctgcctgg gcacctgcgt ggcctacggg   4800
```

```
gatggccact tcatcacctt tgatggcgat cgctacagct ttgaaggcag ctgcgagtac   4860
atcttggccc aggactactg tggggacaac accacccacg ggaccttccg catcgtcacc   4920
gagaacatcc cctgtgggac caccggcacc acctgctcca aggccatcaa gctcttcgtg   4980
gaggtgagaa cggccccagc tgtgagcacc cccgaccctg cagccaacga gccggccccc   5040
agggaagctt cggtcggctt ccggcagcgt ctgcctcccc tgcagagcta cgagctgatc   5100
ctccaagagg ggacctttaa ggcggtggcg agagggccgg gtggggaccc accctacaag   5160
atacgctaca tggggatctt cctggtcatc gagacccacg ggatggccgt gtcctgggac   5220
cggaagacca gcgtgttcat ccgactgcac caggactaca agggcagggt ctgcggcctg   5280
tgcgggaact tcgacgacaa tgccatcaat gactttgcca cgcgtagccg gtccgtggtg   5340
ggggacgcac tggagtttgg gaacagctgg aagctctccc cctcctgccc ggacgccctg   5400
gcacccaagg acccctgcac ggccaacccc ttccgcaagt cctgggccca gaagcagtgc   5460
agcatcctcc acggccccac cttcgccgcc tgccgctccc aggttgactc caccaagtac   5520
tacgaggcct gcgtgaacga cgcgtgtgcc tgcgactcgg gtggcgactg cgagtgtttc   5580
tgcacggctg tggctgccta cgcccaggcc tgccacgacg cgggcctgtg tgtgtcctgg   5640
cggactccgg acacctgccc cttgttctgt gacttctaca acccacatgg gggctgtgag   5700
tggcactacc agccctgcgg ggcaccctgc ctaaaaacct gccggaaccc cagtgggcac   5760
tgcctggtgg acctgcctgg cctggaaggc tgctacccga agtgcccacc cagccagccc   5820
ttcttcaatg aggaccagat gaagtgcgtg gcccagtgtg gctgctacga caaggacgga   5880
aactactatg acgtcggtgc aagggtcccc acagcggaga actgccagag ctgtaactgc   5940
acacccagtg gcatccagtg cgctcacagc cttgaggcct gcacctgcac ctatgaggac   6000
aggacctaca gctaccagga cgtcatctac aacaccaccg atgggcttgg cgcctgcttg   6060
atcgccatct gcggaagcaa cggcaccatc atcaggaagg ctgtggcatg tcctggaact   6120
ccagccacaa cgccattcac cttcaccacc gcctgggtcc cccactccac gacaagcccg   6180
gccctcccgg tctccaccgt gtgtgtccgc gaggtctgcc gctggtccag ctggtacaat   6240
gggcaccgcc cagagcccgg cctgggaggc ggagactttg agacgtttga aaacctgagg   6300
cagagagggt accaggtatg ccctgtgctg gctgacatcg agtgccgggc ggcgcagctt   6360
cccgacatgc cgctggagga gctgggccag caggtggact gtgaccgcat gcgggggctg   6420
atgtgcgcca acagccaaca gagtccccg ctctgtcacg actacgagct gcgggttctc   6480
tgctgcgaat acgtgccctg tggcccctcc ccggccccag gcaccagccc tcagccctcc   6540
ctcagtgcca gcacggagcc tgctgtgcct accccaaccc agaccacagc aaccgaaaag   6600
accaccctat gggtgacccc gagcatccgg tcgacggcgg ccctcacctc gcagactggg   6660
tccagctcag gccccgtgac ggtcaccccc tcggccccag gtaccaccac ctgccagccc   6720
cggtgtcagt ggacagagtg gtttgatgag gactacccca agtctgaaca acttggaggg   6780
gacgttgagt cctacgataa gatcagggcc gctggagggc acttatgcca gcagcctaag   6840
gacatagagt gccaggccga gagcttcccc aactggaccc tggcacaggt ggggcagaag   6900
gtgcactgtg acgtccactt cggcctggtg tgcaggaact gggagcagga gggcgtcttc   6960
aagatgtgct acaactacag gatccgggtc ctctgctgca gtgacgacca ctgcagggga   7020
cgtgccacaa ccccgccacc gaccacagag ctggagacgg ccaccaccac caccacccag   7080
gccctgttct caacgccgca gcctacgagt agcccggggc tgaccagggc tcccccggcc   7140
```

-continued agcaccacag cagtccccac cctctcagaa ggactgacat cccccagata cacaagcacc 7200
cttggtacag ccaccacggg aggccccacg acgcctgcag gctccacaga acccactgtc 7260
ccaggggtgg ccacatccac ccttccaaca cgctcagccc ttccagggac gacggggagc 7320
ttgggcacat ggcgcccctc acagccaccc acgctggccc caacaacaat ggcaacctcc 7380
agagctcgcc cgacaggcac agccagcacc gcttccaaag agccgctgac cacgagcctg 7440
gcgccaacac tcacgagcga gctgtccacc tctcaggccg agaccagcac gcccaggaca 7500
gagacgacaa tgagcccctt gactaacacc accaccagcc agggcacgac ccgctgtcaa 7560
ccgaagtgtg agtggacaga gtggtttgac gtggacttcc caacctcagg ggttgcaggc 7620
ggggacatgg aaacttttga aaacatcagg gctgctgggg gcaagatgtg ctgggcacca 7680
aagagcatag agtgccgggc ggagaactac cccgaggtaa gcatcgacca ggtcgggcag 7740
gtgctgacct gcagcctgga gacggggctg acctgcaaga acgaagacca gacaggcagg 7800
ttcaacatgt gcttcaacta caacgtgcgt gtgctttgct gtgacgacta cagccactgc 7860
cccagtaccc cagccaccag ctccacggcc acgccctcct caactccggg gacgacctgg 7920
atcctcacaa agccgaccac aacagccact acgactgcgt ccactggatc cacggccacc 7980
ccgacctcca ccctgagaac agctccccct cccaaagtgc tgaccaccac ggccaccaca 8040
cccacagtca ccagctccaa agccactccc tcctccagtc cagggactgc aaccgccctt 8100
ccagcactga gaagcacagc caccacaccc acagctacca gcgttacacc catcccctct 8160
tcctccctgg gcaccacctg gacccgccta tcacagacca ccacacccac ggccaccatg 8220
tccacagcca caccctcctc cactccagag actgcccaca cctccacagt gcttaccgcc 8280
acggccacca caactggggc caccggctct gtggccaccc cctcctccac cccaggaaca 8340
gctcacacta ccaaagtgcc aactaccaca accacgggct tcacagccac cccctcctcc 8400
agcccaggga cggcactcac gcctccagtg tggatcagca caaccaccac acccacaacc 8460
agaggctcca cggtgacccc ctcctccatc ccggggacca cccacaccgc cacagtgctg 8520
accaccacca ccacaactgt ggccactggt tctatggcaa caccctcctc tagcacacag 8580
accagtggga ccacccacac acccccagtg ccgaacacca tggccaccac acacgggcga 8640
tccctgcccc ccagcagtcc ccacacggtg cgcacagcct ggacttcggc cacctcgggc 8700
atcttgggca ccacccacat cacagagcct tccacggtga cttcccacac cctagcagca 8760
accaccggta ccacccagca ctcgactcca gccctttcca gccctcaccc tagcagcaga 8820
accaccgagt caccccccttc tccagggacg accaccccgg gccacaccac ggccacctcc 8880
aggaccacag ccacggccac acccagcaag acccgcacct cgaccctgct gcccagcagc 8940
cccacatcgg cccccataac cacggtggtg accatgggct gtgagcccca gtgtgcctgg 9000
tcagagtggc tggactacag ctaccccatg ccggggccct ctggcgggga ctttgacacc 9060
tactccaaca tccgtgcggc cggaggggcc gtctgtgagc agcccctggg cctcgagtgc 9120
cgtgcccagg cccagcctgg tgtcccccctg cgggagttgg gccaggtcgt ggaatgcagc 9180
ctggactttg gcctggtctg caggaaccgt gagcaggtgg ggaagttcaa gatgtgcttc 9240
aactatgaaa tccgtgtgtt ctgctgcaac tacggccact gccccagcac cccggccacc 9300
agctctacgg ccatgccctc ctccactccg gggacgacct ggatcctcac agagctgacc 9360
acaacagcca ctacgactga gtccactgga tccacggcca ccccgtcctc caccccaggg 9420
accacctgga tcctcacaga gccgagcact acagccaccg tgacggtgcc caccggatcc 9480
acggccaccg cctcctccac ccaggcaact gctggcaccc cacatgtgag caccacggcc 9540

```
acgacaccca cagtcaccag ctccaaagcc actcccttct ccagtccagg gactgcaacc   9600
gcccttccag cactgagaag cacagccacc acacccacag ctaccagctt tacagccatc   9660
ccctcctcct ccctgggcac cacctggacc cgcctatcac agaccaccac acccacggcc   9720
accatgtcca cagccacacc ctcctccact ccagagactg tccacacctc cacagtgctt   9780
accaccacgg ccaccacaac cggggccacc ggctctgtgg ccaccccctc ctccacccca   9840
ggaacagctc acactaccaa agtgctgact accacaacca cgggcttcac agccaccccc   9900
tcctccagcc cagggacggc acgcacgctt ccagtgtgga tcagcacaac caccacaccc   9960
acaaccagag gttccacggt gacccccctcc tccatcccgg ggaccaccca cacccccaca  10020
gtgctgacca ccaccaccac aactgtggcc actggttcta tggcaacacc ctcctctagc  10080
acacagacca gtgggaccac ccacacaccc ccagtgccga acaccacggc caccacacac  10140
gggcgatccc tgtcccccag cagtccccac acggtgcgca cagcctggac ttcggccacc  10200
tcaggcacct tgggcaccac ccacatcaca gagccttcca cggggacttc ccacacccca  10260
gcagcaacca ccggtaccac ccagcactcg actccagccc tgtccagccc tcaccctagc  10320
agcaggacca ccgagtcacc cccttctcca gggacgacca ccccgggcca caccagggcc  10380
acctccagga ccacggccac ggccacaccc agcaagaccc gcacctcgac cctgctgccc  10440
agcagcccca catcggcccc aataaccacg gtggtgacca tgggctgtga gccccagtgt  10500
gcctggtcag agtggctgga ctacagctac cccatgccgg ggccctctgg cggggacttt  10560
gacacctact ccaacatccg tgcggccgga ggggccgtct gtgagcagcc cctgggcctc  10620
gagtgccgtg cccaggccca gcctggtgtc cccctgcggg agttgggcca ggtcgtggaa  10680
tgcagcctgg actttggcct ggtctgcagg aaccgtgagc aggtggggaa gttcaagatg  10740
tgcttcaact atgaaatccg tgtgttctgc tgcaactacg gccactgccc cagcaccccg  10800
gccaccagct ctacggccac gccctcctcc actccaggga cgacctggat cctcacagag  10860
cagaccacag cagccactac gaccgcaacc actggatcca cggccatccc gtcctccacc  10920
ccgggaacag ctcccccctcc caaagtgctg accagcacgg ccaccacacc cacagccacc  10980
agttccaaag ccacttcctc ctccagtcca aggactgcaa ccacccttcc agtgctgaca  11040
agcacagcca ccaaatccac agctaccagc tttacaccca tcccctcctt caccccttggg  11100
accaccggga ccctcccaga acagaccacc acacccatgg ccaccatgtc cacaatccac  11160
ccctcctcca ctccggagac cacccacacc tccacagtgc tgaccacgaa ggccaccacg  11220
acaagggcca ccagttccat gtccaccccc tcctccactc cggggacgac ctggatcctc  11280
acagagctga ccacagcagc cactacaact gcagccactg gccccacggc caccccgtcc  11340
tccaccccag ggaccacctg gatcctcaca gagcccagca ctacagccac cgtgacggtg  11400
cccaccggat ccacggccac cgcctcctcc acccgggcaa ctgctggcac cctcaaagtg  11460
ctgaccagca cggccaccac acccacagtc atcagctcca gagccactcc ctcctccagt  11520
ccagggactg caaccgccct tccagcactg agaagcacag ccaccacacc cacagctacc  11580
agcgttacag ccatcccctc ttcctccctg ggcaccgcct ggacccgcct atcacagacc  11640
accacaccca cggccaccat gtccacagcc acaccctcct ctactccaga gactgtccac  11700
acctccacag tgcttaccac cacgaccacc acaaccaggg ccaccggctc tgtggccacc  11760
ccctcctcca ccccaggaac agctcacact accaaagtgc cgactaccac aaccacgggc  11820
ttcacagcca ccccctcctc cagcccaggg acggcactca cgcctccagt gtggatcagc  11880
```

```
acaaccacca cacccacaac cagaggctcc acggtgaccc cctcctccat cccggggacc  11940
acccacaccg ccacagtgct gaccaccacc accacaactg tggccactgg ttctatggca  12000
acaccctcct ctagcacaca gaccagtggg accacccaca cacccccagt gccgaacacc  12060
acggccacca cacacgggcg gtccctgccc cccagcagtc cccacacggt gcgcacagcc  12120
tggacttcgg ccacctcggg catcttgggc accacccaca tcacagagcc ttccacggtg  12180
acttcccaca ccccagcagc aaccaccagt accacccagc actcgactcc agccctgtcc  12240
agccctcacc ctagcagcag gaccaccgag tcaccccctt ctccagggac gaccaccccg  12300
ggccacacca ggggcacctc caggaccaca gccacagcca cacccagcaa gacccgcacc  12360
tcgaccctgc tgcccagcag ccccacatcg gcccccataa ccacggtggt gaccacgggc  12420
tgtgagcccc agtgtgcctg gtcagagtgg ctggactaca gctaccccat gccggggccc  12480
tctggcgggg actttgacac ctactccaac atccgtgcgg ccggaggggc agtctgtgag  12540
cagcccctgg gcctcgagtg ccgtgcccag gcccagcctg gtgtcccccct gcgggagttg  12600
ggccaggtcg tggaatgcag cctggacttt ggcctggtct gcaggaaccg tgagcaggtg  12660
gggaagttca agatgtgctt caactatgaa atccgtgtgt tctgctgcaa ctacggccac  12720
tgccccagca ccccggccac cagctctacg gccacgccct cctcaactcc ggggacgacc  12780
tggatcctca caaagctgac cacaacagcc actacgactg agtccactgg atccacggcc  12840
accccgtcct ccaccccagg gaccacctgg atcctcacag agccgagcac tacagccacc  12900
gtgacggtgc ccaccggatc cacggccacc gcctcctcca cccaggcaac tgctggcacc  12960
ccacatgtga gcaccacggc cacgacaccc acagtcacca gctccaaagc cactcccttc  13020
tccagtccag ggactgcaac cgcccttcca gcactgagaa gcacagccac cacacccaca  13080
gctaccagct ttacagccat cccctcctcc tccctgggca ccacctggac ccgcctatca  13140
cagaccacca cacccacggc caccatgtcc acagccacac cctcctccac tccagagact  13200
gcccacacct ccacagtgct taccaccacg gccaccacaa ccagggccac cggctctgtg  13260
gccacccccct cttccacccc aggaacagct cacactacca aagtgccgac taccacaacc  13320
acgggcttca cagtcacccc ctcctccagc ccagggacgg cacgcacgcc tccagtgtgg  13380
atcagcacaa ccaccacacc cacaaccagt ggctccacgg tgacccccctc ctccgtcccg  13440
gggaccaccc acacccccac agtgctgacc accaccacca caactgtggc cactggttct  13500
atggcaacac cctcctctag cacacagacc agtgggacca cccacacacc cccagtgccg  13560
aacaccacgg ccaccacaca cgggcgatcc ctgtccccca gcagtcccca cacggtgcgc  13620
acagcctgga cttcggccac ctcaggcacc ttgggcacca cccacatcac agagccttcc  13680
acggggactt cccacacccc agcagcaacc accggtacca cccagcactc gactccagcc  13740
ctgtccagcc ctcaccctag cagcaggacc accgagtcac cccctcccc agggacgacc  13800
accccgggcc acaccacggc cacctccagg accacggcca cggccacacc cagcaagacc  13860
cgcacctcga ccctgctgcc cagcagcccc acatcggccc ccataaccac ggtggtgacc  13920
acgggctgtg agccccagtg tgcctggtca gagtggctgg actacagcta ccccatgccg  13980
gggccctctg gcggggactt tgacacctac tccaacatcc gtgcggccgg aggggccgtc  14040
tgtgagcagc ccctgggcct cgagtgccgt gcccaggccc agcctggtgt cccccctgggg  14100
gagttgggcc aggtcgtgga atgcagcctg gactttggcc tggtctgcag gaaccgtgag  14160
caggtgggga agttcaagat gtgcttcaac tatgaaatcc gtgtgttctg ctgcaactac  14220
ggccactgcc ccagcacccc ggccaccagc tctacggcca tgccctcctc cactccgggg  14280
```

```
acgacctgga tcctcacaga gctgaccaca acagccacta cgactgcatc cactggatcc  14340
acggccaccc cgtcctccac cccgggaaca gctccccctc ccaaagtgct gaccagcccg  14400
gccaccacac ccacagccac cagttccaaa gccacttcct cctccagtcc aaggactgca  14460
accacccttc cagtgctgac aagcacagcc accaaatcca cagctaccag cgttacaccc  14520
atcccctcct ccaccccttgg gaccaccggg accctcccag aacagaccac cacacccgtg  14580
gccaccatgt ccacaatcca cccctcctcc actccggaga ccacccacac ctccacagtg  14640
ctgaccacga aggccaccac gacaagggcc accagttcca cgtccacccc ctcctccact  14700
ccggggacga cctggatcct cacagagctg accacagcag ccactacaac tgcagccact  14760
ggccccacgg ccaccccgtc ctccacccca gggaccacct ggatcctcac agagctgacc  14820
acaacagcca ctacgactgc gtccactgga tccacggcca ccccgtcctc caccccaggg  14880
accacctgga tcctcacaga gccgagcact acagccaccg tgacggtgcc caccggatcc  14940
acggccaccg cctcctccac ccaggcaact gctggcaccc cacatgtgag caccacggcc  15000
acgacaccca cagtcaccag ctccaaagcc actccctcct ccagtccagg gactgcaact  15060
gcccttccag cactgagaag cacagccacc acacccacag ctaccagctt tacagccatc  15120
ccctcctcct ccctgggcac cacctggacc cgcctatcac agaccaccac acccacggcc  15180
accatgtcca cagccacacc ctcctccact ccagagactg tccacacctc cacagtgctt  15240
accgccacgg ccaccacaac cggggccacc ggctctgtgg ccacccccctc ctccacccca  15300
ggaacagctc acactaccaa agtgccgact accacaacca cgggcttcac agccaccccc  15360
tcctccagcc cagggacggc actcacgcct ccaaccacca cacccatgtc caccatgtcc  15420
acaatccaca cctcctctac tccagagacc acccacacct ccacagtgct gaccaccaca  15480
gccaccatga caagggccac caattccacg gccacaccct cctccactct ggggacgacc  15540
cggatcctca ctgagctgac cacaacagcc actacaactg cagccactgg atccacggcc  15600
accctgtcct ccaccccagg gaccacctgg atcctcacag agccgagcac tatagccacc  15660
gtgatggtgc ccaccggttc cacggccacc gcctcctcca ctctgggaac agctcacacc  15720
cccaaagtgg tgaccaccat ggccactatg cccacagcca ctgcctccac ggttcccagc  15780
tcgtccaccg tggggaccac ccgcacccct gcagtgctcc ccagcagcct gccaaccttc  15840
agcgtgtcca ctgtgtcctc ctcagtcctc accaccctga gacccactgg cttccccagc  15900
tcccacttct ctactccctg cttctgcagg gcatttggac agtttttctc gcccggggaa  15960
gtcatctaca ataagaccga ccgagccggc tgccatttct acgcagtgtg caatcagcac  16020
tgtgacattg accgcttcca gggcgcctgt cccacctccc caccgccagt gtcctccgcc  16080
ccgctgtcct cgccctcccc tgcccctggc tgtgacaatg ccatccctct ccggcaggtg  16140
aatgagacct ggaccctgga gaactgcacg gtggccaggt gcgtgggtga caaccgtgtc  16200
gtcctgctgg acccaaagcc tgtggccaac gtcacctgcg tgaacaagca cctgcccatc  16260
aaagtgtcgg acccgagcca gccctgtgac ttccactatg agtgcgagtg tgagtgcgtc  16320
ggtggccgcg ggattacccc gggggcaggc atctgcagca tgtggggcgg ctcccactat  16380
tccacctttg acggcacctc ttacaccttc cggggcaact gcacctatgt cctcatgaga  16440
gagatccatg cacgctttgg gaatctcagc ctctacctgg acaaccacta ctgcacggcc  16500
tctgccactg ccgctgccgc tgccgcccgc tgcccccgcg ccctcagcat ccactacaag  16560
tccatggata tcgtcctcac tgtcaccatg gtgcatggga aggaggaggg cctgatcctg  16620
```

```
tttgaccaaa ttccggtgag cagcggtttc agcaagaacg gcgtgcttgt gtctgtgctg  16680
gggaccacca ccatgcgtgt ggacattcct gccctgggcg tgagcgtcac cttcaatggc  16740
caagtcttcc aggcccggct gccctacagc ctcttccaca acaacaccga gggccagtgc  16800
ggcacctgca ccaacaacca gagggacgac tgtctccagc gggacggaac cactgccgcc  16860
agttgcaagg acatggccaa gacgtggctg gtccccgaca gcagaaagga tggctgctgg  16920
gccccgactg gcacaccccc cactgccagc cccgcagccc cggtgtctag cacacccacc  16980
cccaccccat gcccaccaca gccgctctgt gatctgatgc tgagccaggt ctttgctgag  17040
tgccacaacc ttgtgccccc gggcccattc ttcaacgcct gcatcagcga ccactgcagg  17100
ggccgccttg aggtgccctg ccagagcctg gaggcttacg cagagctctg ccgcgcccgg  17160
ggagtgtgca gtgactggcg aggtgcaacc ggtggcctgt gcgacctcac ctgcccaccc  17220
accaaagtgt acaagccatg cggccccata cagcctgcca cctgcaactc taggaaccag  17280
agcccacagc tggaggggat ggcggagggc tgcttctgcc ctgaggacca gatcctcttc  17340
aacgcacaca tgggcatctg cgtgcaggcc tgcccctgcg tgggacccga tgggtttcct  17400
aaatttcccg gggagcggtg ggtcagcaac tgccagtcct gcgtgtgtga cgagggttca  17460
gtgtcggtgc agtgcaagcc cctgccctgt gacgcccagg gtcagccccc gccgtgcaac  17520
cgtcccggct tcgtaaccgt gaccaggccc cgggccgaga acccctgctg ccccgagacg  17580
gtgtgcgtgt gcaacacaac cacctgcccc cagagcctgc ctgtgtgccc gccagggcag  17640
gagtccatct gcacccagga ggagggcgac tgctgtccca ccttccgctg cagacctcag  17700
ctgtgttcgt acaatggcac cttctacggg gttggtgcaa ccttcccagg cgcccttccc  17760
tgccacatgt gtacctgcct ctctggggac acccaggacc caacggtgca atgtcaggag  17820
gatgcctgca acaatactac ctgtccccag ggctttgagt acaagagagt ggccgggcag  17880
tgctgtgggg agtgcgtcca gaccgcctgc ctcacgcccg atggccagcc agtccagctg  17940
aatgaaacct gggtcaacag ccatgtggac aactgcaccg tgtacctctg tgaggctgag  18000
ggtggagtcc atttgctgac cccacagcct gcatcctgcc cagatgtgtc cagctgcagg  18060
gggagcctca ggaaaaccgg ctgctgctac tcctgtgagg aggactcctg tcaagtccgc  18120
atcaacacga ccatcctgtg gcaccagggc tgcgagaccg aggtcaacat caccttctgc  18180
gagggctcct gccccggagc gtccaagtac tcagcagagg cccaggccat gcagcaccag  18240
tgcacctgct gccaggagag gcgggtccac gaggagacgg tgcccttgca ctgtcctaac  18300
ggctcagcca tcctgcacac ctacacccac gctgtccagg tcctctgtgg gctgcttgcc  18360
tggggcctgc aggctggagg acacatccgg ggggcagtcc aggaccccca gcagccactg  18420
aaggaccagg aagcctctgg gaaggccagg caggggggtg gctacaggca gaccgtggcc  18480
tggggagaca aaagcaatgc tcgtgcctgg ctgcagaagc ctgtggtgtg ggtgcagagc  18540
ggggccttcc ccacaccggg gcctgcctct gccctgtgcc cttggaaaat gggcattcag  18600
cctgaaacca ccaagcagct cagagatgct aacatcctga aggagagcaa acgctccatc  18660
agtagagaaa gacaaaggca atgtgctcaa gctatcaggt ttaatagagg atttggagga  18720
cagatctgga aatctcaacg ctttttctag                                    18750
```

<210> SEQ ID NO 7
<211> LENGTH: 14360
<212> TYPE: DNA
<213> ORGANISM: Human

<400> SEQUENCE: 7

```
tttcgccagc tcctctgggg gtgacaggca agtgagacgt gctcagagct ccgatgccaa     60
ggccagggac catggcgctg tgtctgctga ccttggtcct ctcgctcttg cccccacaag    120
ctgctgcaga acaggacctc agtgtgaaca gggctgtgtg ggatggagga gggtgcatct    180
cccaagggga cgtcttgaac cgtcagtgcc agcagctgtc tcagcacgtt aggacaggtt    240
ctgcggcaaa caccgccaca ggtacaacat ctacaaatgt cgtggagcca agaatgtatt    300
tgagttgcag caccaaccct gagatgacct cgattgagtc cagtgtgact tcagacactc    360
ctggtgtctc cagtaccagg atgacaccaa cagaatccag aacaacttca gaatctacca    420
gtgacagcac cacacttttc cccagttcta ctgaagacac ttcatctcct acaactcctg    480
aaggcaccga cgtgcccatg tcaacaccaa gtgaagaaag catttcatca acaatggctt    540
ttgtcagcac tgcacctctt cccagttttg aggcctacac atctttaaca tataaggttg    600
atatgagcac acctctgacc acttctactc aggcaagttc atctcctact actcctgaaa    660
gcaccaccat acccaaatca actaacagtg aaggaagcac tccattaaca agtatgcctg    720
ccagcaccat gaaggtggcc agttcagagg ctatcaccct tttgacaact cctgttgaaa    780
tcagcacacc tgtgaccatt tctgctcaag ccagttcatc tcctacaact gctgaaggtc    840
ccagcctgtc aaactcagct cctagtggag gaagcactcc attaacaaga atgcctctca    900
gcgtgatgct ggtggtcagt tctgaggcta gcaccctttc aacaactcct gctgccacca    960
acattcctgt gatcacttct actgaagcca gttcatctcc tacaacggct gaaggcacca   1020
gcataccaac ctcaacttat actgaaggaa gcactccatt aacaagtacg cctgccagca   1080
ccatgccggt tgccacttct gaaatgagca cactttcaat aactcctgtt gacaccagca   1140
cacttgtgac cacttctact gaacccagtt cacttcctac aactgctgaa gctaccagca   1200
tgctaacctc aactcttagt gaaggaagca ctccattaac aaatatgcct gtcagcacca   1260
tattggtggc cagttctgag gctagcacca cttcaacaat tcctgttgac tccaaaactt   1320
ttgtgaccac tgctagtgaa gccagctcat ctcccacaac tgctgaagat accagcattg   1380
caacctcaac tcctagtgaa ggaagcactc cattaacaag tatgcctgtc agcaccactc   1440
cagtggccag ttctgaggct agcaaccttt caacaactcc tgttgactcc aaaactcagg   1500
tgaccacttc tactgaagcc agttcatctc ctccaactgc tgaagttaac agcatgccaa   1560
cctcaactcc tagtgaagga agcactccat taacaagtat gtctgtcagc accatgccgg   1620
tggccagttc tgaggctagc accctttcaa caactcctgt tgacaccagc acacctgtga   1680
ccacttctag tgaagccagt tcatcttcta caactcctga aggtaccagc ataccaacct   1740
caactcctag tgaaggaagc actccattaa caaacatgcc tgtcagcacc aggctggtgg   1800
tcagttctga ggctagcacc acttcaacaa ctcctgctga ctccaacact tttgtgacca   1860
cttctagtga agctagttca tcttctacaa ctgctgaagg taccagcatg ccaacctcaa   1920
cttacagtga aagaggcact acaataacaa gtatgtctgt cagcaccaca ctggtggcca   1980
gttctgaggc tagcaccctt tcaacaactc ctgttgactc caacactcct gtgaccactt   2040
caactgaagc cacttcatct tctacaactg cggaaggtac cagcatgcca acctcaactt   2100
atactgaagg aagcactcca ttaacaagta tgcctgtcaa caccacactg gtggccagtt   2160
ctgaggctag caccctttca acaactcctg ttgacaccag cacacctgtg accacttcaa   2220
ctgaagccag ttcctctcct acaactgctg atggtgccag tatgccaacc tcaactccta   2280
gtgaaggaag cactccatta acaagtatgc ctgtcagcaa aacgctgttg accagttctg   2340
```

```
aggctagcac cctttcaaca actcctcttg acacaagcac acatatcacc acttctactg   2400
aagccagttg ctctcctaca accactgaag gtaccagcat gccaatctca actcctagtg   2460
aaggaagtcc tttattaaca agtatacctg tcagcatcac accggtgacc agtcctgagg   2520
ctagcaccct ttcaacaact cctgttgact ccaacagtcc tgtgaccact tctactgaag   2580
tcagttcatc tcctacacct gctgaaggta ccagcatgcc aacctcaact tatagtgaag   2640
gaagaactcc tttaacaagt atgcctgtca gcaccacact ggtggccact tctgcaatca   2700
gcaccctttc aacaactcct gttgacacca gcacacctgt gaccaattct actgaagccc   2760
gttcgtctcc tacaacttct gaaggtacca gcatgccaac ctcaactcct ggggaaggaa   2820
gcactccatt aacaagtatg cctgacagca ccacgccggt agtcagttct gaggctagaa   2880
cactttcagc aactcctgtt gacaccagca cacctgtgac cacttctact gaagccactt   2940
catctcctac aactgctgaa ggtaccagca taccaacctc gactcctagt gaaggaacga   3000
ctccattaac aagcacacct gtcagccaca cgctggtggc caattctgag gctagcaccc   3060
tttcaacaac tcctgttgac tccaacactc ctttgaccac ttctactgaa gccagttcac   3120
ctcctcccac tgctgaaggt accagcatgc caacctcaac tcctagtgaa ggaagcactc   3180
cattaacacg tatgcctgtc agcaccacaa tggtggccag ttctgaaacg agcacacttt   3240
caacaactcc tgctgacacc agcacacctg tgaccactta ttctcaagcc agttcatctt   3300
ctacaactgc tgacggtacc agcatgccaa cctcaactta tagtgaagga agcactccac   3360
taacaagtgt gcctgtcagc accaggctgg tggtcagttc tgaggctagc accctttcca   3420
caactcctgt cgacaccagc atacctgtca ccacttctac tgaagccagt tcatctccta   3480
caactgctga aggtaccagc ataccaacct cacctcccag tgaaggaacc actccgttag   3540
caagtatgcc tgtcagcacc acgctggtgg tcagttctga ggctaacacc ctttcaacaa   3600
ctcctgtgga ctccaaaact caggtggcca cttctactga agccagttca cctcctccaa   3660
ctgctgaagt taccagcatg ccaacctcaa ctcctggaga aagaagcact ccattaacaa   3720
gtatgcctgt cagacacacg ccagtggcca gttctgaggc tagcaccctt tcaacatctc   3780
ccgttgacac cagcacacct gtgaccactt ctgctgaaac cagttcctct cctacaaccg   3840
ctgaaggtac cagcttgcca acctcaacta ctagtgaagg aagtactcta ttaacaagta   3900
tacctgtcag caccacgctg gtgaccagtc ctgaggctag caccctttta acaactcctg   3960
ttgacactaa aggtcctgtg gtcacttcta atgaagtcag ttcatctcct acacctgctg   4020
aaggtaccag catgccaacc tcaacttata gtgaaggaag aactccttta acaagtatac   4080
ctgtcaacac cacactggtg gccagttctg caatcagcat cctttcaaca actcctgttg   4140
acaacagcac acctgtgacc acttctactg aagcctgttc atctcctaca acttctgaag   4200
gtaccagcat gccaaactca aatcctagtg aaggaaccac tccgttaaca agtatacctg   4260
tcagcaccac gccggtagtc agttctgagg ctagcaccct ttcagcaact cctgttgaca   4320
ccagcacccc tgggaccact tctgctgaag ccacttcatc tcctacaact gctgaaggta   4380
tcagcatacc aacctcaact cctagtgaag gaaagactcc attaaaaagt atacctgtca   4440
gcaacacgcc ggtggccaat tctgaggcta gcaccctttc aacaactcct gttgactcta   4500
acagtcctgt ggtcacttct acagcagtca gttcatctcc tacacctgct gaaggtacca   4560
gcatagcaat ctcaacgcct agtgaaggaa gcactgcatt aacaagtata cctgtcagca   4620
ccacaacagt ggccagttct gaaatcaaca gcctttcaac aactcctgct gtcaccagca   4680
cacctgtgac cacttattct caagccagtt catctcctac aactgctgac ggtaccagca   4740
```

```
tgcaaacctc aacttatagt gaaggaagca ctccactaac aagtttgcct gtcagcacca   4800
tgctggtggt cagttctgag gctaacaccc tttcaacaac ccctattgac tccaaaactc   4860
aggtgaccgc ttctactgaa gccagttcat ctacaaccgc tgaaggtagc agcatgacaa   4920
tctcaactcc tagtgaagga agtcctctat taacaagtat acctgtcagc accacgccgg   4980
tggccagtcc tgaggctagc accctttcaa caactcctgt tgactccaac agtcctgtga   5040
tcacttctac tgaagtcagt tcatctccta cacctgctga aggtaccagc atgccaacct   5100
caacttatac tgaaggaaga actcctttaa caagtataac tgtcagaaca acaccggtgg   5160
ccagctctgc aatcagcacc ctttcaacaa ctcccgttga caacagcaca cctgtgacca   5220
cttctactga agcccgttca tctcctacaa cttctgaagg taccagcatg ccaaactcaa   5280
ctcctagtga aggaaccact ccattaacaa gtatacctgt cagcaccacg ccggtactca   5340
gttctgaggc tagcaccctt tcagcaactc ctattgacac cagcacccct gtgaccactt   5400
ctactgaagc cacttcgtct cctacaactg ctgaaggtac cagcatacca acctcgactc   5460
ttagtgaagg aatgactcca ttaacaagca cacctgtcag ccacacgctg gtggccaatt   5520
ctgaggctag caccctttca acaactcctg ttgactctaa cagtcctgtg gtcacttcta   5580
cagcagtcag ttcatctcct acacctgctg aaggtaccag catagcaacc tcaacgccta   5640
gtgaaggaag cactgcatta acaagtatac ctgtcagcac cacaacagtg gccagttctg   5700
aaaccaacac cctttcaaca actcccgctg tcaccagcac acctgtgacc acttatgctc   5760
aagtcagttc atctcctaca actgctgacg gtagcagcat gccaacctca actcctaggg   5820
aaggaaggcc tccattaaca agtatacctg tcagcaccac aacagtggcc agttctgaaa   5880
tcaacaccct ttcaacaact cttgctgaca ccaggacacc tgtgaccact tattctcaag   5940
ccagttcatc tcctacaact gctgatggta ccagcatgcc aaccccagct tatagtgaag   6000
gaagcactcc actaacaagt atgcctctca gcaccacgct ggtggtcagt tctgaggcta   6060
gcactctttc cacaactcct gttgacacca gcactcctgc caccacttct actgaaggca   6120
gttcatctcc tacaactgca ggaggtacca gcatacaaac ctcaactcct agtgaacgga   6180
ccactccatt agcaggtatg cctgtcagca ctacgcttgt ggtcagttct gagggtaaca   6240
ccctttcaac aactcctgtt gactccaaaa ctcaggtgac caattctact gaagccagtt   6300
catctgcaac cgctgaaggt agcagcatga caatctcagc tcctagtgaa ggaagtcctc   6360
tactaacaag tatacctctc agcaccacgc cggtggccag tcctgaggct agcacccttt   6420
caacaactcc tgttgactcc aacagtcctg tgatcacttc tactgaagtc agttcatctc   6480
ctatacctac tgaaggtacc agcatgcaaa cctcaactta tagtgacaga agaactcctt   6540
taacaagtat gcctgtcagc accacagtgg tggccagttc tgcaatcagc accctttcaa   6600
caactcctgt tgacaccagc acacctgtga ccaattctac tgaagcccgt tcatctccta   6660
caacttctga aggtaccagc atgccaacct caactcctag tgaaggaagc actccattca   6720
caagtatgcc tgtcagcacc atgccggtag ttacttctga ggctagcacc ctttcagcaa   6780
ctcctgttga caccagcaca cctgtgacca cttctactga agccacttca tctcctacaa   6840
ctgctgaagg taccagcata ccaacttcaa ctcttagtga aggaacgact ccattaacaa   6900
gtatacctgt cagccacacg ctggtggcca attctgaggt tagcaccctt tcaacaactc   6960
ctgttgactc caacactcct ttcactactt ctactgaagc cagttcacct cctcccactg   7020
ctgaaggtac cagcatgcca acctcaactt ctagtgaagg aaacactcca ttaacacgta   7080
```

```
tgcctgtcag caccacaatg gtggccagtt ttgaaacaag cacactttct acaactcctg   7140
ctgacaccag cacacctgtg actacttatt ctcaagccgg ttcatctcct acaactgctg   7200
acgatactag catgccaacc tcaacttata gtgaaggaag cactccacta acaagtgtgc   7260
ctgtcagcac catgccggtg gtcagttctg aggctagcac ccattccaca actcctgttg   7320
acaccagcac acctgtcacc acttctactg aagccagttc atctcctaca actgctgaag   7380
gtaccagcat accaacctca cctcctagtg aaggaaccac tccgttagca agtatgcctg   7440
tcagcaccac gccggtggtc agttctgagg ctggcaccct ttccacaact cctgttgaca   7500
ccagcacacc tatgaccact tctactgaag ccagttcatc tcctacaact gctgaagata   7560
tcgtcgtgcc aatctcaact gctagtgaag gaagtactct attaacaagt atacctgtca   7620
gcaccacgcc agtggccagt cctgaggcta gcaccctttc aacaactcct gttgactcca   7680
acagtcctgt ggtcacttct actgaaatca gttcatctgc tacatccgct gaaggtacca   7740
gcatgcctac ctcaacttat agtgaaggaa gcactccatt aagaagtatg cctgtcagca   7800
ccaagccgtt ggccagttct gaggctagca ctctttcaac aactcctgtt gacaccagca   7860
tacctgtcac cacttctact gaaaccagtt catctcctac aactgcaaaa gataccagca   7920
tgccaatctc aactcctagt gaagtaagta cttcattaac aagtatactt gtcagcacca   7980
tgccagtggc cagttctgag gctagcaccc tttcaacaac tcctgttgac accaggacac   8040
ttgtgaccac ttccactgga accagttcat ctcctacaac tgctgaaggt agcagcatgc   8100
caacctcaac tcctggtgaa agaagcactc cattaacaaa tatacttgtc agcaccacgc   8160
tgttggccaa ttctgaggct agcacccttt caacaactcc tgttgacacc agcacacctg   8220
tcaccacttc tgctgaagcc agttcttctc ctacaactgc tgaaggtacc agcatgcgaa   8280
tctcaactcc tagtgatgga agtactccat taacaagtat acttgtcagc accctgccag   8340
tggccagttc tgaggctagc accgtttcaa caactgctgt tgacaccagc atacctgtca   8400
ccacttctac tgaagccagt tcctctccta caactgctga agttaccagc atgccaacct   8460
caactcctag tgaaacaagt actccattaa ctagtatgcc tgtcaaccac acgccagtgg   8520
ccagttctga ggctggcacc ctttcaacaa ctcctgttga caccagcaca cctgtgacca   8580
cttctactaa agccagttca tctcctacaa ctgctgaagg tatcgtcgtg ccaatctcaa   8640
ctgctagtga aggaagtact ctattaacaa gtatacctgt cagcaccacg ccggtggcca   8700
gttctgaggc tagcaccctt tcaacaactc ctgttgatac cagcatacct gtcaccactt   8760
ctactgaagg cagttcttct cctacaactg ctgaaggtac cagcatgcca atctcaactc   8820
ctagtgaagt aagtactcca ttaacaagta tacttgtcag caccgtgcca gtggccggtt   8880
ctgaggctag caccctttca acaactcctg ttgacaccag gacacctgtc accacttctg   8940
ctgaagctag ttcttctcct acaactgctg aaggtaccag catgccaatc tcaactcctg   9000
gcgaaagaag aactccatta acaagtatgt ctgtcagcac catgccggtg gccagttctg   9060
aggctagcac cctttcaaga actcctgctg acaccagcac acctgtgacc acttctactg   9120
aagccagttc ctctcctaca actgctgaag gtaccggcat accaatctca actcctagtg   9180
aaggaagtac tccattaaca agtatacctg tcagcaccac gccagtggcc attcctgagg   9240
ctagcaccct ttcaacaact cctgttgact ccaacagtcc tgtggtcact tctactgaag   9300
tcagttcatc tcctacacct gctgaaggta ccagcatgcc aatctcaact tatagtgaag   9360
gaagcactcc attaacaggt gtgcctgtca gcaccacacc ggtgaccagt tctgcaatca   9420
gcaccctttc aacaactcct gttgacacca gcacacctgt gaccacttct actgaagccc   9480
```

```
attcatctcc tacaacttct gaaggtacca gcatgccaac ctcaactcct agtgaaggaa   9540
gtactccatt aacatatatg cctgtcagca ccatgctggt agtcagttct gaggatagca   9600
ccctttcagc aactcctgtt gacaccagca cacctgtgac cacttctact gaagccactt   9660
catctacaac tgctgaaggt accagcattc caacctcaac tcctagtgaa ggaatgactc   9720
cattaactag tgtacctgtc agcaacacgc cggtggccag ttctgaggct agcatccttt   9780
caacaactcc tgttgactcc aacactcctt tgaccacttc tactgaagcc agttcatctc   9840
ctcccactgc tgaaggtacc agcatgccaa cctcaactcc tagtgaagga agcactccat   9900
taacaagtat gcctgtcagc accacaacgg tggccagttc tgaaacgagc accctttcaa   9960
caactcctgc tgacaccagc acacctgtga ccacttattc tcaagccagt tcatctcctc  10020
caattgctga cggtactagc atgccaacct caacttatag tgaaggaagc actccactaa  10080
caaatatgtc tttcagcacc acgccagtgg tcagttctga ggctagcacc ctttccacaa  10140
ctcctgttga caccagcaca cctgtcacca cttctactga agccagttta tctcctacaa  10200
ctgctgaagg taccagcata ccaacctcaa gtcctagtga aggaaccact ccattagcaa  10260
gtatgcctgt cagcaccacg ccggtggtca gttctgaggt taacaccctt tcaacaactc  10320
ctgtggactc caacactctg gtgaccactt ctactgaagc cagttcatct cctacaatcg  10380
ctgaaggtac cagcttgcca acctcaacta ctagtgaagg aagcactcca ttatcaatta  10440
tgcctctcag taccacgccg gtggccagtt ctgaggctag caccctttca acaactcctg  10500
ttgacaccag cacacctgtg accacttctt ctccaaccaa ttcatctcct acaactgctg  10560
aagttaccag catgccaaca tcaactgctg gtgaaggaag cactccatta acaaatatgc  10620
ctgtcagcac cacaccggtg gccagttctg aggctagcac cctttcaaca actcctgttg  10680
actccaacac ttttgttacc agttctagtc aagccagttc atctccagca actcttcagg  10740
tcaccactat gcgtatgtct actccaagtg aaggaagctc ttcattaaca actatgctcc  10800
tcagcagcac atatgtgacc agttctgagg ctagcacacc ttccactcct tctgttgaca  10860
gaagcacacc tgtgaccact tctactcaga gcaattctac tcctacacct cctgaagtta  10920
tcaccctgcc aatgtcaact cctagtgaag taagcactcc attaaccatt atgcctgtca  10980
gcaccacatc ggtgaccatt tctgaggctg gcacagcttc aacacttcct gttgacacca  11040
gcacacctgt gatcacttct acccaagtca gttcatctcc tgtgactcct gaaggtacca  11100
ccatgccaat ctggacgcct agtgaaggaa gcactccatt aacaactatg cctgtcagca  11160
ccacacgtgt gaccagctct gagggtagca ccctttcaac accttctgtt gtcaccagca  11220
cacctgtgac cacttctact gaagccattt catcttctgc aactcttgac agcaccacca  11280
tgtctgtgtc aatgcccatg gaaataagca cccttgggac cactattctt gtcagtacca  11340
cacctgttac gaggtttcct gagagtagca ccccttccat accatctgtt tacaccagca  11400
tgtctatgac cactgcctct gaaggcagtt catctcctac aactcttgaa ggcaccacca  11460
ccatgcctat gtcaactacg agtgaaagaa gcactttatt gacaactgtc ctcatcagcc  11520
ctatatctgt gatgagtcct tctgaggcca gcacactttc aacacctcct ggtgatacca  11580
gcacaccttt gctcacctct accaaagccg gttcattctc catacctgct gaagtcacta  11640
ccatacgtat ttcaattacc agtgaaagaa gcactccatt aacaactctc cttgtcagca  11700
ccacacttcc aactagcttt cctggggcca gcatagcttc gacacctcct cttgacacaa  11760
gcacaacttt taccccttct actgacactg cctcaactcc cacaattcct gtagccacca  11820
```

```
ccatatctgt atcagtgatc acagaaggaa gcacacctgg gacaaccatt tttattccca  11880
gcactcctgt caccagttct actgctgatg tctttcctgc aacaactggt gctgtatcta  11940
cccctgtgat aacttccact gaactaaaca caccatcaac ctccagtagt agtaccacca  12000
catctttttc aactactaag gaatttacaa cacccgcaat gactactgca gctcccctca  12060
catatgtgac catgtctact gcccccagca cacccagaac aaccagcaga ggctgcacta  12120
cttctgcatc aacgctttct gcaaccagta cacctcacac ctctacttct gtcaccaccc  12180
gtcctgtgac cccttcatca gaatccagca ggccgtcaac aattacttct cacaccatcc  12240
cacctacatt tcctcctgct cactccagta cacctccaac aacctctgcc tcctccacga  12300
ctgtgaaccc tgaggctgtc accaccatga ccaccaggac aaaacccagc acacggacca  12360
cttccttccc cacggtgacc accaccgctg tccccacgaa tactacaatt aagagcaacc  12420
ccacctcaac tcctactgtg ccaagaacca caacatgctt tggagatggg tgccagaata  12480
cggcctctcg ctgcaagaat ggaggcacct gggatgggct caagtgccag tgtcccaacc  12540
tctattatgg ggagttgtgt gaggaggtgg tcagcagcat tgacataggg ccaccggaga  12600
ctatctctgc ccaaatggaa ctgactgtga cagtgaccag tgtgaagttc accgaagagc  12660
taaaaaacca ctcttcccag gaattccagg agttcaaaca gacattcacg gaacagatga  12720
atattgtgta ttccgggatc cctgagtatg tcggggtgaa catcacaaag ctacgtcttg  12780
gcagtgtggt ggtggagcat gacgtcctcc taagaaccaa gtacacacca gaatacaaga  12840
cagtattgga caatgccacc gaagtagtga aagagaaaat cacaaaagtg accacacagc  12900
aaataatgat taatgatatt tgctcagaca tgatgtgttt caacaccact ggcacccaag  12960
tgcaaaacat tacggtgacc cagtacgacc ctgaagagga ctgccggaag atggccaagg  13020
aatatggaga ctacttcgta gtggagtacc gggaccagaa gccatactgc atcagcccct  13080
gtgagcctgg cttcagtgtc tccaagaact gtaacctcgg caagtgccag atgtctctaa  13140
gtggacctca gtgcctctgc gtgaccacgg aaactcactg gtacagtggg gagacctgta  13200
accagggcac ccagaagagt ctggtgtacg gcctcgtggg ggcaggggtc gtgctgatgc  13260
tgatcatcct ggtagctctc ctgatgctcg ttttccgctc caagagagag gtgaaacggc  13320
aaaagtacag attgtctcag ttatacaagt ggcaagaaga ggacagtgga ccagctcctg  13380
ggaccttcca aaacattggc tttgacatct gccaagatga tgattccatc cacctggagt  13440
ccatctatag taatttccag ccctccttga gacacataga ccctgaaaca aagatccgaa  13500
ttcagaggcc tcaggtaatg acgacatcat tttaaggcat ggagctgaga agtctgggag  13560
tgaggagatc ccagtccggc taagcttggt ggagcatttt cccattgaga gccttccatg  13620
ggaactcaat gttcccattg taagtacagg aaacaagccc tgtacttacc aaggagaaag  13680
aggagagaca gcagtgctgg gagattctca aatagaaacc cgtggacgct ccaatgggct  13740
tgtcatgata tcaggctagg ctttcctgct catttttcaa agacgctcca gatttgaggg  13800
tactctgact gcaacatctt tcaccccatt gatcgccagg attgatttgg ttgatctggc  13860
tgagcaggcg ggtgtccccg tcctccctca ctgccccata tgtgtccctc ctaaagctgc  13920
atgctcagtt gaagaggacg agaggacgac cttctctgat agaggaggac cacgcttcag  13980
tcaaaggcat acaagtatct atctggactt ccctgctagc acttccaaac aagctcagag  14040
atgttcctcc cctcatctgc ccgggttcag taccatggac agcgccctcg acccgctgtt  14100
tacaaccatg acccctggga cactggactg catgcacttt acatatcaca aaatgctctc  14160
ataagaatta ttgcatacca tcttcatgaa aaacacctgt atttaaatat agagcattta  14220
```

```
ccttttggta tataagattg tgggtatttt ttaagttctt attgttatga gttctgattt  14280

tttccttagt aaatattata atatatattt gtagtaacta aaaataataa agcaatttta  14340

ttacaatttt aaaaaaaaaa                                              14360
```

<210> SEQ ID NO 8
<211> LENGTH: 632
<212> TYPE: DNA
<213> ORGANISM: Human

<400> SEQUENCE: 8

```
cccagaatgt tgacagtcgc tctcctagcc cttctctgtg cctcagcctc tggcaatgcc     60

attcaggcca ggtcttcctc ctatagtgga gagtatggaa gtggtggtgg aaagcgattc    120

tctcattctg gcaaccagtt ggacggcccc atcaccgccc tccgggtccg agtcaacaca    180

tactacatcg taggtcttca ggtgcgctat ggcaaggtgt ggagcgacta tgtgggtggt    240

cgcaacggag acctggagga gatctttctg caccctgggg aatcagtgat ccaggtttct    300

gggaagtaca agtggtacct gaagaagctg gtatttgtga cagacaaggg ccgctatctg    360

tcttttggga aagacagtgg cacaagtttc aatgccgtcc ccttgcaccc caacaccgtg    420

ctccgcttca tcagtggccg gtctggttct ctcatcgatg ccattggcct gcactgggat    480

gtttacccca ctagctgcag cagatgctga gcctcctctc cttggcaggg gcactgtgat    540

gaggagtaag aactccctta tcactaaccc ccatccaaat ggctcaataa aaaaatatgg    600

ttaaggctaa aaaaaaaaaa aaaaaaaaaa aa                                  632
```

<210> SEQ ID NO 9
<211> LENGTH: 6207
<212> TYPE: PRT
<213> ORGANISM: Human

<400> SEQUENCE: 9

```
Met Ser Val Gly Arg Arg Lys Leu Ala Leu Leu Trp Ala Leu Ala Leu
1               5                   10                  15

Ala Leu Ala Cys Thr Arg His Thr Gly His Ala Gln Asp Gly Ser Ser
            20                  25                  30

Glu Ser Ser Tyr Lys His His Pro Ala Leu Ser Pro Ile Ala Arg Gly
        35                  40                  45

Pro Ser Gly Val Pro Leu Arg Gly Ala Thr Val Phe Pro Ser Leu Arg
    50                  55                  60

Thr Ile Pro Val Val Arg Ala Ser Asn Pro Ala His Asn Gly Arg Val
65                  70                  75                  80

Cys Ser Thr Trp Gly Ser Phe His Tyr Lys Thr Phe Asp Gly Asp Val
                85                  90                  95

Phe Arg Phe Pro Gly Leu Cys Asn Tyr Val Phe Ser Glu His Cys Gly
            100                 105                 110

Ala Ala Tyr Glu Asp Phe Asn Ile Gln Leu Arg Arg Ser Gln Glu Ser
        115                 120                 125

Ala Ala Pro Thr Leu Ser Arg Val Leu Met Lys Val Asp Gly Val Val
    130                 135                 140

Ile Gln Leu Thr Lys Gly Ser Val Leu Val Asn Gly His Pro Val Leu
145                 150                 155                 160

Leu Pro Phe Ser Gln Ser Gly Val Leu Ile Gln Gln Ser Ser Ser Tyr
                165                 170                 175

Thr Lys Val Glu Ala Arg Leu Gly Leu Val Leu Met Trp Asn His Asp
```

-continued

```
        180                 185                 190

Asp Ser Leu Leu Leu Glu Leu Asp Thr Lys Tyr Ala Asn Lys Thr Cys
    195                 200                 205

Gly Leu Cys Gly Asp Phe Asn Gly Met Pro Val Val Ser Glu Leu Leu
    210                 215                 220

Ser His Asn Thr Lys Leu Thr Pro Met Glu Phe Gly Asn Leu Gln Lys
225                 230                 235                 240

Met Asp Asp Pro Thr Glu Gln Cys Gln Asp Pro Val Pro Glu Pro Pro
                245                 250                 255

Arg Asn Cys Ser Thr Gly Phe Gly Ile Cys Glu Glu Leu Leu His Gly
            260                 265                 270

Gln Leu Phe Ser Gly Cys Val Ala Leu Val Asp Val Gly Ser Tyr Leu
        275                 280                 285

Glu Ala Cys Arg Gln Asp Leu Cys Phe Cys Glu Asp Thr Asp Leu Leu
    290                 295                 300

Ser Cys Val Cys His Thr Leu Ala Glu Tyr Ser Arg Gln Cys Thr His
305                 310                 315                 320

Ala Gly Gly Leu Pro Gln Asp Trp Arg Gly Pro Asp Phe Cys Pro Gln
                325                 330                 335

Lys Cys Pro Asn Asn Met Gln Tyr His Glu Cys Arg Ser Pro Cys Ala
            340                 345                 350

Asp Thr Cys Ser Asn Gln Glu His Ser Arg Ala Cys Glu Asp His Cys
        355                 360                 365

Val Ala Gly Cys Phe Cys Pro Glu Gly Thr Val Leu Asp Asp Ile Gly
    370                 375                 380

Gln Thr Gly Cys Val Pro Val Ser Lys Cys Ala Cys Val Tyr Asn Gly
385                 390                 395                 400

Ala Ala Tyr Ala Pro Gly Ala Thr Tyr Ser Thr Asp Cys Thr Asn Cys
                405                 410                 415

Thr Cys Ser Gly Gly Arg Trp Ser Cys Gln Glu Val Pro Cys Pro Gly
            420                 425                 430

Thr Cys Ser Val Leu Gly Gly Ala His Phe Ser Thr Phe Asp Gly Lys
        435                 440                 445

Gln Tyr Thr Val His Gly Asp Cys Ser Tyr Val Leu Thr Lys Pro Cys
    450                 455                 460

Asp Ser Ser Ala Phe Thr Val Leu Ala Glu Leu Arg Arg Cys Gly Leu
465                 470                 475                 480

Thr Asp Ser Glu Thr Cys Leu Lys Ser Val Thr Leu Ser Leu Asp Gly
                485                 490                 495

Ala Gln Thr Val Val Val Ile Lys Ala Ser Gly Glu Val Phe Leu Asn
            500                 505                 510

Gln Ile Tyr Thr Gln Leu Pro Ile Ser Ala Ala Asn Val Thr Ile Phe
        515                 520                 525

Arg Pro Ser Thr Phe Phe Ile Ile Ala Gln Thr Ser Leu Gly Leu Gln
    530                 535                 540

Leu Asn Leu Gln Leu Val Pro Thr Met Gln Leu Phe Met Gln Leu Ala
545                 550                 555                 560

Pro Lys Leu Arg Gly Gln Thr Cys Gly Leu Cys Gly Asn Phe Asn Ser
                565                 570                 575

Ile Gln Ala Asp Asp Phe Arg Thr Leu Ser Gly Val Val Glu Ala Thr
            580                 585                 590

Ala Ala Ala Phe Phe Asn Thr Phe Lys Thr Gln Ala Ala Cys Pro Asn
        595                 600                 605
```

```
Ile Arg Asn Ser Phe Glu Asp Pro Cys Ser Leu Ser Val Glu Asn Ala
    610                 615                 620

Pro Arg Met Gly Ala Pro Ser Ala Cys Arg Thr Leu Val Leu Ala Leu
625                 630                 635                 640

Ala Ala Met Leu Val Val Pro Gln Ala Glu Thr Gln Gly Pro Val Glu
                645                 650                 655

Pro Ser Trp Glu Asn Ala Gly His Thr Met Asp Gly Gly Ala Pro Thr
            660                 665                 670

Ser Ser Pro Thr Arg Arg Val Ser Phe Val Pro Pro Val Thr Val Phe
        675                 680                 685

Pro Ser Leu Ser Arg Lys Gln Met Leu Pro Leu Pro Ala Gly Lys Gly
    690                 695                 700

Val Phe Ala Ser Pro Lys Gly Gly Gly Pro Asp Leu Gly Val Gln Leu
705                 710                 715                 720

Pro Pro Ala Leu Asn Pro Ala His Asn Gly Arg Val Cys Ser Thr Trp
                725                 730                 735

Gly Asp Phe His Tyr Lys Thr Phe Asp Gly Asp Val Phe Arg Phe Pro
            740                 745                 750

Gly Leu Cys Asn Tyr Val Phe Ser Glu His Cys Arg Ala Ala Tyr Glu
        755                 760                 765

Asp Phe Asn Val Gln Leu Arg Arg Gly Leu Val Gly Ser Arg Pro Val
    770                 775                 780

Val Thr Arg Val Val Ile Lys Ala Gln Gly Leu Val Leu Glu Ala Ser
785                 790                 795                 800

Asn Gly Ser Val Leu Ile Asn Gly Gln Arg Glu Glu Leu Pro Tyr Ser
                805                 810                 815

Arg Thr Gly Leu Leu Val Glu Gln Ser Gly Asp Tyr Ile Lys Val Ser
            820                 825                 830

Ile Arg Leu Val Leu Thr Phe Leu Trp Asn Gly Glu Asp Ser Ala Leu
        835                 840                 845

Leu Glu Leu Asp Pro Lys Tyr Ala Asn Gln Thr Cys Gly Leu Cys Gly
    850                 855                 860

Asp Phe Asn Gly Leu Pro Ala Phe Asn Glu Phe Tyr Ala His Asn Ala
865                 870                 875                 880

Arg Leu Thr Pro Leu Gln Phe Gly Asn Leu Gln Lys Leu Asp Gly Pro
                885                 890                 895

Thr Glu Gln Cys Pro Asp Pro Leu Pro Leu Pro Ala Gly Asn Cys Thr
            900                 905                 910

Asp Glu Glu Gly Ile Cys His Arg Thr Leu Leu Gly Pro Ala Phe Ala
        915                 920                 925

Glu Cys His Ala Leu Val Asp Ser Thr Ala Tyr Leu Ala Ala Cys Ala
    930                 935                 940

Gln Asp Leu Cys Arg Cys Pro Thr Cys Pro Cys Ala Thr Phe Val Glu
945                 950                 955                 960

Tyr Ser Arg Gln Cys Ala His Ala Gly Gly Gln Pro Arg Asn Trp Arg
                965                 970                 975

Cys Pro Glu Leu Cys Pro Arg Thr Cys Pro Leu Asn Met Gln His Gln
            980                 985                 990

Glu Cys Gly Ser Pro Cys Thr Asp  Thr Cys Ser Asn Pro  Gln Arg Ala
        995                 1000                1005

Gln Leu  Cys Glu Asp His Cys  Val Asp Gly Cys Phe  Cys Pro Pro
    1010                1015                1020
```

```
Gly Arg  Ser Cys Thr Val Leu  Asp Asp Ile Thr His  Ser Gly Cys
    1025                 1030                 1035

Leu Pro  Leu Gly Gln Cys Pro  Cys Thr His Gly Gly  Arg Thr Tyr
    1040                 1045                 1050

Ser Pro  Gly Thr Ser Phe Asn  Thr Thr Cys Ser Ser  Cys Thr Cys
    1055                 1060                 1065

Ser Gly  Gly Leu Trp Gln Cys  Gln Asp Leu Pro Cys  Pro Gly Thr
    1070                 1075                 1080

Cys Ser  Val Gln Gly Gly Ala  His Ile Ser Thr Tyr  Asp Glu Lys
    1085                 1090                 1095

Leu Tyr  Asp Leu His Gly Asp  Cys Ser Tyr Val Leu  Ser Lys Lys
    1100                 1105                 1110

Cys Ala  Asp Ser Ser Phe Thr  Val Leu Ala Glu Leu  Arg Lys Cys
    1115                 1120                 1125

Gly Leu  Thr Asp Asn Glu Asn  Cys Leu Lys Ala Val  Thr Leu Ser
    1130                 1135                 1140

Leu Asp  Gly Gly Asp Thr Ala  Ile Arg Val Gln Ala  Asp Gly Gly
    1145                 1150                 1155

Val Phe  Leu Asn Ser Ile Tyr  Thr Gln Leu Pro Leu  Ser Ala Ala
    1160                 1165                 1170

Asn Ile  Thr Leu Phe Thr Pro  Ser Ser Phe Phe Ile  Val Val Gln
    1175                 1180                 1185

Thr Gly  Leu Gly Leu Gln Leu  Leu Val Gln Leu Val  Pro Leu Met
    1190                 1195                 1200

Gln Val  Phe Val Arg Leu Asp  Pro Ala His Gln Gly  Gln Met Cys
    1205                 1210                 1215

Gly Leu  Cys Gly Asn Phe Asn  Gln Asn Gln Ala Asp  Asp Phe Thr
    1220                 1225                 1230

Ala Leu  Ser Gly Val Val Glu  Ala Thr Gly Ala Ala  Phe Ala Asn
    1235                 1240                 1245

Thr Trp  Lys Ala Gln Ala Ala  Cys Ala Asn Ala Arg  Asn Ser Phe
    1250                 1255                 1260

Glu Asp  Pro Cys Ser Leu Ser  Val Glu Asn Glu Asn  Tyr Ala Arg
    1265                 1270                 1275

His Trp  Cys Ser Arg Leu Thr  Asp Pro Asn Ser Ala  Phe Ser Arg
    1280                 1285                 1290

Cys His  Ser Ile Ile Asn Pro  Lys Pro Phe His Ser  Asn Cys Met
    1295                 1300                 1305

Phe Asp  Thr Cys Asn Cys Glu  Arg Ser Glu Asp Cys  Leu Cys Ala
    1310                 1315                 1320

Ala Leu  Ser Ser Tyr Val His  Ala Cys Ala Ala Lys  Gly Val Gln
    1325                 1330                 1335

Leu Ser  Asp Trp Arg Asp Gly  Val Cys Thr Lys Tyr  Met Gln Asn
    1340                 1345                 1350

Cys Pro  Lys Ser Gln Arg Tyr  Ala Tyr Val Val Asp  Ala Cys Gln
    1355                 1360                 1365

Pro Thr  Cys Arg Gly Leu Ser  Glu Ala Asp Val Thr  Cys Ser Val
    1370                 1375                 1380

Ser Phe  Val Pro Val Asp Gly  Cys Thr Cys Pro Ala  Gly Thr Phe
    1385                 1390                 1395

Leu Asn  Asp Ala Gly Ala Cys  Val Pro Ala Gln Glu  Cys Pro Cys
    1400                 1405                 1410

Tyr Ala  His Gly Thr Val Leu  Ala Pro Gly Glu Val  Val His Asp
```

-continued

```
    1415                1420                1425

Glu Gly  Ala Val Cys Ser Cys  Thr Gly Gly Lys Leu  Ser Cys Leu
    1430                1435                1440

Gly Ala  Ser Leu Gln Lys Ser  Thr Gly Cys Ala Ala  Pro Met Val
    1445                1450                1455

Tyr Leu  Asp Cys Ser Asn Ser  Ser Ala Gly Thr Pro  Gly Ala Glu
    1460                1465                1470

Cys Leu  Arg Ser Cys His Thr  Leu Asp Val Gly Cys  Phe Ser Thr
    1475                1480                1485

His Cys  Val Ser Gly Cys Val  Cys Pro Pro Gly Leu  Val Ser Asp
    1490                1495                1500

Gly Ser  Gly Gly Cys Ile Ala  Glu Glu Asp Cys Pro  Cys Val His
    1505                1510                1515

Asn Glu  Ala Thr Tyr Lys Pro  Gly Glu Thr Ile Arg  Val Asp Cys
    1520                1525                1530

Asn Thr  Cys Thr Cys Arg Asn  Arg Arg Trp Glu Cys  Ser His Arg
    1535                1540                1545

Leu Cys  Leu Gly Thr Cys Val  Ala Tyr Gly Asp Gly  His Phe Ile
    1550                1555                1560

Thr Phe  Asp Gly Asp Arg Tyr  Ser Phe Glu Gly Ser  Cys Glu Tyr
    1565                1570                1575

Ile Leu  Ala Gln Asp Tyr Cys  Gly Asp Asn Thr Thr  His Gly Thr
    1580                1585                1590

Phe Arg  Ile Val Thr Glu Asn  Ile Pro Cys Gly Thr  Thr Gly Thr
    1595                1600                1605

Thr Cys  Ser Lys Ala Ile Lys  Leu Phe Val Glu Val  Arg Thr Ala
    1610                1615                1620

Pro Ala  Val Ser Thr Pro Asp  Pro Ala Ala Asn Glu  Pro Ala Pro
    1625                1630                1635

Arg Glu  Ala Ser Val Gly Phe  Arg Gln Arg Leu Pro  Pro Leu Gln
    1640                1645                1650

Ser Tyr  Glu Leu Ile Leu Gln  Glu Gly Thr Phe Lys  Ala Val Ala
    1655                1660                1665

Arg Gly  Pro Gly Gly Asp Pro  Pro Tyr Lys Ile Arg  Tyr Met Gly
    1670                1675                1680

Ile Phe  Leu Val Ile Glu Thr  His Gly Met Ala Val  Ser Trp Asp
    1685                1690                1695

Arg Lys  Thr Ser Val Phe Ile  Arg Leu His Gln Asp  Tyr Lys Gly
    1700                1705                1710

Arg Val  Cys Gly Leu Cys Gly  Asn Phe Asp Asp Asn  Ala Ile Asn
    1715                1720                1725

Asp Phe  Ala Thr Arg Ser Arg  Ser Val Val Gly Asp  Ala Leu Glu
    1730                1735                1740

Phe Gly  Asn Ser Trp Lys Leu  Ser Pro Ser Cys Pro  Asp Ala Leu
    1745                1750                1755

Ala Pro  Lys Asp Pro Cys Thr  Ala Asn Pro Phe Arg  Lys Ser Trp
    1760                1765                1770

Ala Gln  Lys Gln Cys Ser Ile  Leu His Gly Pro Thr  Phe Ala Ala
    1775                1780                1785

Cys Arg  Ser Gln Val Asp Ser  Thr Lys Tyr Tyr Glu  Ala Cys Val
    1790                1795                1800

Asn Asp  Ala Cys Ala Cys Asp  Ser Gly Gly Asp Cys  Glu Cys Phe
    1805                1810                1815
```

```
Cys Thr  Ala Val Ala Ala Tyr  Ala Gln Ala Cys His  Asp Ala Gly
    1820                 1825                 1830

Leu Cys  Val Ser Trp Arg Thr  Pro Asp Thr Cys Pro  Leu Phe Cys
    1835                 1840                 1845

Asp Phe  Tyr Asn Pro His Gly  Gly Cys Glu Trp His  Tyr Gln Pro
    1850                 1855                 1860

Cys Gly  Ala Pro Cys Leu Lys  Thr Cys Arg Asn Pro  Ser Gly His
    1865                 1870                 1875

Cys Leu  Val Asp Leu Pro Gly  Leu Glu Gly Cys Tyr  Pro Lys Cys
    1880                 1885                 1890

Pro Pro  Ser Gln Pro Phe Phe  Asn Glu Asp Gln Met  Lys Cys Val
    1895                 1900                 1905

Ala Gln  Cys Gly Cys Tyr Asp  Lys Asp Gly Asn Tyr  Tyr Asp Val
    1910                 1915                 1920

Gly Ala  Arg Val Pro Thr Ala  Glu Asn Cys Gln Ser  Cys Asn Cys
    1925                 1930                 1935

Thr Pro  Ser Gly Ile Gln Cys  Ala His Ser Leu Glu  Ala Cys Thr
    1940                 1945                 1950

Cys Thr  Tyr Glu Asp Arg Thr  Tyr Ser Tyr Gln Asp  Val Ile Tyr
    1955                 1960                 1965

Asn Thr  Thr Asp Gly Leu Gly  Ala Cys Leu Ile Ala  Ile Cys Gly
    1970                 1975                 1980

Ser Asn  Gly Thr Ile Ile Arg  Lys Ala Val Ala Cys  Pro Gly Thr
    1985                 1990                 1995

Pro Ala  Thr Thr Pro Phe Thr  Phe Thr Thr Ala Trp  Val Pro His
    2000                 2005                 2010

Ser Thr  Thr Ser Pro Ala Leu  Pro Val Ser Thr Val  Cys Val Arg
    2015                 2020                 2025

Glu Val  Cys Arg Trp Ser Ser  Trp Tyr Asn Gly His  Arg Pro Glu
    2030                 2035                 2040

Pro Gly  Leu Gly Gly Gly Asp  Phe Glu Thr Phe Glu  Asn Leu Arg
    2045                 2050                 2055

Gln Arg  Gly Tyr Gln Val Cys  Pro Val Leu Ala Asp  Ile Glu Cys
    2060                 2065                 2070

Arg Ala  Ala Gln Leu Pro Asp  Met Pro Leu Glu Glu  Leu Gly Gln
    2075                 2080                 2085

Gln Val  Asp Cys Asp Arg Met  Arg Gly Leu Met Cys  Ala Asn Ser
    2090                 2095                 2100

Gln Gln  Ser Pro Pro Leu Cys  His Asp Tyr Glu Leu  Arg Val Leu
    2105                 2110                 2115

Cys Cys  Glu Tyr Val Pro Cys  Gly Pro Ser Pro Ala  Pro Gly Thr
    2120                 2125                 2130

Ser Pro  Gln Pro Ser Leu Ser  Ala Ser Thr Glu Pro  Ala Val Pro
    2135                 2140                 2145

Thr Pro  Thr Gln Thr Thr Ala  Thr Glu Lys Thr Thr  Leu Trp Val
    2150                 2155                 2160

Thr Pro  Ser Ile Arg Ser Thr  Ala Ala Leu Thr Ser  Gln Thr Gly
    2165                 2170                 2175

Ser Ser  Ser Gly Pro Val Thr  Val Thr Pro Ser Ala  Pro Gly Thr
    2180                 2185                 2190

Thr Thr  Cys Gln Pro Arg Cys  Gln Trp Thr Glu Trp  Phe Asp Glu
    2195                 2200                 2205
```

```
Asp Tyr  Pro Lys Ser Glu Gln  Leu Gly Gly Asp Val  Glu Ser Tyr
    2210                 2215                 2220

Asp Lys  Ile Arg Ala Ala Gly  Gly His Leu Cys Gln  Gln Pro Lys
    2225                 2230                 2235

Asp Ile  Glu Cys Gln Ala Glu  Ser Phe Pro Asn Trp  Thr Leu Ala
    2240                 2245                 2250

Gln Val  Gly Gln Lys Val His  Cys Asp Val His Phe  Gly Leu Val
    2255                 2260                 2265

Cys Arg  Asn Trp Glu Gln Glu  Gly Val Phe Lys Met  Cys Tyr Asn
    2270                 2275                 2280

Tyr Arg  Ile Arg Val Leu Cys  Cys Ser Asp Asp His  Cys Arg Gly
    2285                 2290                 2295

Arg Ala  Thr Thr Pro Pro Pro  Thr Thr Glu Leu Glu  Thr Ala Thr
    2300                 2305                 2310

Thr Thr  Thr Thr Gln Ala Leu  Phe Ser Thr Pro Gln  Pro Thr Ser
    2315                 2320                 2325

Ser Pro  Gly Leu Thr Arg Ala  Pro Pro Ala Ser Thr  Thr Ala Val
    2330                 2335                 2340

Pro Thr  Leu Ser Glu Gly Leu  Thr Ser Pro Arg Tyr  Thr Ser Thr
    2345                 2350                 2355

Leu Gly  Thr Ala Thr Thr Gly  Gly Pro Thr Thr Pro  Ala Gly Ser
    2360                 2365                 2370

Thr Glu  Pro Thr Val Pro Gly  Val Ala Thr Ser Thr  Leu Pro Thr
    2375                 2380                 2385

Arg Ser  Ala Leu Pro Gly Thr  Thr Gly Ser Leu Gly  Thr Trp Arg
    2390                 2395                 2400

Pro Ser  Gln Pro Pro Thr Leu  Ala Pro Thr Thr Met  Ala Thr Ser
    2405                 2410                 2415

Arg Ala  Arg Pro Thr Gly Thr  Ala Ser Thr Ala Ser  Lys Glu Pro
    2420                 2425                 2430

Leu Thr  Thr Ser Leu Ala Pro  Thr Leu Thr Ser Glu  Leu Ser Thr
    2435                 2440                 2445

Ser Gln  Ala Glu Thr Ser Thr  Pro Arg Thr Glu Thr  Thr Met Ser
    2450                 2455                 2460

Pro Leu  Thr Asn Thr Thr Thr  Ser Gln Gly Thr Thr  Arg Cys Gln
    2465                 2470                 2475

Pro Lys  Cys Glu Trp Thr Glu  Trp Phe Asp Val Asp  Phe Pro Thr
    2480                 2485                 2490

Ser Gly  Val Ala Gly Gly Asp  Met Glu Thr Phe Glu  Asn Ile Arg
    2495                 2500                 2505

Ala Ala  Gly Gly Lys Met Cys  Trp Ala Pro Lys Ser  Ile Glu Cys
    2510                 2515                 2520

Arg Ala  Glu Asn Tyr Pro Glu  Val Ser Ile Asp Gln  Val Gly Gln
    2525                 2530                 2535

Val Leu  Thr Cys Ser Leu Glu  Thr Gly Leu Thr Cys  Lys Asn Glu
    2540                 2545                 2550

Asp Gln  Thr Gly Arg Phe Asn  Met Cys Phe Asn Tyr  Asn Val Arg
    2555                 2560                 2565

Val Leu  Cys Cys Asp Asp Tyr  Ser His Cys Pro Ser  Thr Pro Ala
    2570                 2575                 2580

Thr Ser  Ser Thr Ala Thr Pro  Ser Ser Thr Pro Gly  Thr Thr Trp
    2585                 2590                 2595

Ile Leu  Thr Lys Pro Thr Thr  Thr Ala Thr Thr Thr  Ala Ser Thr
```

```
    2600                2605                2610

Gly Ser  Thr Ala Thr Pro Thr  Ser Thr Leu Arg Thr  Ala Pro Pro
    2615                2620                2625

Pro Lys  Val Leu Thr Thr Thr  Ala Thr Thr Pro Thr  Val Thr Ser
    2630                2635                2640

Ser Lys  Ala Thr Pro Ser Ser  Ser Pro Gly Thr Ala  Thr Ala Leu
    2645                2650                2655

Pro Ala  Leu Arg Ser Thr Ala  Thr Thr Pro Thr Ala  Thr Ser Val
    2660                2665                2670

Thr Pro  Ile Pro Ser Ser Ser  Leu Gly Thr Thr Trp  Thr Arg Leu
    2675                2680                2685

Ser Gln  Thr Thr Thr Pro Thr  Ala Thr Met Ser Thr  Ala Thr Pro
    2690                2695                2700

Ser Ser  Thr Pro Glu Thr Ala  His Thr Ser Thr Val  Leu Thr Ala
    2705                2710                2715

Thr Ala  Thr Thr Thr Gly Ala  Thr Gly Ser Val Ala  Thr Pro Ser
    2720                2725                2730

Ser Thr  Pro Gly Thr Ala His  Thr Thr Lys Val Pro  Thr Thr Thr
    2735                2740                2745

Thr Thr  Gly Phe Thr Ala Thr  Pro Ser Ser Ser Pro  Gly Thr Ala
    2750                2755                2760

Leu Thr  Pro Pro Val Trp Ile  Ser Thr Thr Thr Thr  Pro Thr Thr
    2765                2770                2775

Arg Gly  Ser Thr Val Thr Pro  Ser Ser Ile Pro Gly  Thr Thr His
    2780                2785                2790

Thr Ala  Thr Val Leu Thr Thr  Thr Thr Thr Thr Val  Ala Thr Gly
    2795                2800                2805

Ser Met  Ala Thr Pro Ser Ser  Ser Thr Gln Thr Ser  Gly Thr Thr
    2810                2815                2820

His Thr  Pro Pro Val Pro Asn  Thr Met Ala Thr Thr  His Gly Arg
    2825                2830                2835

Ser Leu  Pro Pro Ser Ser Pro  His Thr Val Arg Thr  Ala Trp Thr
    2840                2845                2850

Ser Ala  Thr Ser Gly Ile Leu  Gly Thr Thr His Ile  Thr Glu Pro
    2855                2860                2865

Ser Thr  Val Thr Ser His Thr  Leu Ala Ala Thr Thr  Gly Thr Thr
    2870                2875                2880

Gln His  Ser Thr Pro Ala Leu  Ser Ser Pro His Pro  Ser Ser Arg
    2885                2890                2895

Thr Thr  Glu Ser Pro Pro Ser  Pro Gly Thr Thr Thr  Pro Gly His
    2900                2905                2910

Thr Thr  Ala Thr Ser Arg Thr  Thr Ala Thr Ala Thr  Pro Ser Lys
    2915                2920                2925

Thr Arg  Thr Ser Thr Leu Leu  Pro Ser Ser Pro Thr  Ser Ala Pro
    2930                2935                2940

Ile Thr  Thr Val Val Thr Met  Gly Cys Glu Pro Gln  Cys Ala Trp
    2945                2950                2955

Ser Glu  Trp Leu Asp Tyr Ser  Tyr Pro Met Pro Gly  Pro Ser Gly
    2960                2965                2970

Gly Asp  Phe Asp Thr Tyr Ser  Asn Ile Arg Ala Ala  Gly Gly Ala
    2975                2980                2985

Val Cys  Glu Gln Pro Leu Gly  Leu Glu Cys Arg Ala  Gln Ala Gln
    2990                2995                3000
```

```
Pro Gly  Val Pro Leu Arg Glu  Leu Gly Gln Val Val  Glu Cys Ser
    3005                 3010                 3015

Leu Asp  Phe Gly Leu Val Cys  Arg Asn Arg Glu Gln  Val Gly Lys
    3020                 3025                 3030

Phe Lys  Met Cys Phe Asn Tyr  Glu Ile Arg Val Phe  Cys Cys Asn
    3035                 3040                 3045

Tyr Gly  His Cys Pro Ser Thr  Pro Ala Thr Ser Ser  Thr Ala Met
    3050                 3055                 3060

Pro Ser  Ser Thr Pro Gly Thr  Thr Trp Ile Leu Thr  Glu Leu Thr
    3065                 3070                 3075

Thr Thr  Ala Thr Thr Thr Glu  Ser Thr Gly Ser Thr  Ala Thr Pro
    3080                 3085                 3090

Ser Ser  Thr Pro Gly Thr Thr  Trp Ile Leu Thr Glu  Pro Ser Thr
    3095                 3100                 3105

Thr Ala  Thr Val Thr Val Pro  Thr Gly Ser Thr Ala  Thr Ala Ser
    3110                 3115                 3120

Ser Thr  Gln Ala Thr Ala Gly  Thr Pro His Val Ser  Thr Thr Ala
    3125                 3130                 3135

Thr Thr  Pro Thr Val Thr Ser  Ser Lys Ala Thr Pro  Phe Ser Ser
    3140                 3145                 3150

Pro Gly  Thr Ala Thr Ala Leu  Pro Ala Leu Arg Ser  Thr Ala Thr
    3155                 3160                 3165

Thr Pro  Thr Ala Thr Ser Phe  Thr Ala Ile Pro Ser  Ser Ser Leu
    3170                 3175                 3180

Gly Thr  Thr Trp Thr Arg Leu  Ser Gln Thr Thr Thr  Pro Thr Ala
    3185                 3190                 3195

Thr Met  Ser Thr Ala Thr Pro  Ser Ser Thr Pro Glu  Thr Val His
    3200                 3205                 3210

Thr Ser  Thr Val Leu Thr Thr  Thr Ala Thr Thr Thr  Gly Ala Thr
    3215                 3220                 3225

Gly Ser  Val Ala Thr Pro Ser  Ser Thr Pro Gly Thr  Ala His Thr
    3230                 3235                 3240

Thr Lys  Val Leu Thr Thr Thr  Thr Thr Gly Phe Thr  Ala Thr Pro
    3245                 3250                 3255

Ser Ser  Ser Pro Gly Thr Ala  Arg Thr Leu Pro Val  Trp Ile Ser
    3260                 3265                 3270

Thr Thr  Thr Thr Pro Thr Thr  Arg Gly Ser Thr Val  Thr Pro Ser
    3275                 3280                 3285

Ser Ile  Pro Gly Thr Thr His  Thr Pro Thr Val Leu  Thr Thr Thr
    3290                 3295                 3300

Thr Thr  Thr Val Ala Thr Gly  Ser Met Ala Thr Pro  Ser Ser Ser
    3305                 3310                 3315

Thr Gln  Thr Ser Gly Thr Thr  His Thr Pro Pro Val  Pro Asn Thr
    3320                 3325                 3330

Thr Ala  Thr Thr His Gly Arg  Ser Leu Ser Pro Ser  Ser Pro His
    3335                 3340                 3345

Thr Val  Arg Thr Ala Trp Thr  Ser Ala Thr Ser Gly  Thr Leu Gly
    3350                 3355                 3360

Thr Thr  His Ile Thr Glu Pro  Ser Thr Gly Thr Ser  His Thr Pro
    3365                 3370                 3375

Ala Ala  Thr Thr Gly Thr Thr  Gln His Ser Thr Pro  Ala Leu Ser
    3380                 3385                 3390
```

```
Ser Pro  His Pro Ser Ser Arg  Thr Thr Glu Ser Pro  Pro Ser Pro
    3395                 3400                 3405

Gly Thr  Thr Thr Pro Gly His  Thr Arg Ala Thr Ser  Arg Thr Thr
    3410                 3415                 3420

Ala Thr  Ala Thr Pro Ser Lys  Thr Arg Thr Ser Thr  Leu Leu Pro
    3425                 3430                 3435

Ser Ser  Pro Thr Ser Ala Pro  Ile Thr Thr Val Val  Thr Met Gly
    3440                 3445                 3450

Cys Glu  Pro Gln Cys Ala Trp  Ser Glu Trp Leu Asp  Tyr Ser Tyr
    3455                 3460                 3465

Pro Met  Pro Gly Pro Ser Gly  Gly Asp Phe Asp Thr  Tyr Ser Asn
    3470                 3475                 3480

Ile Arg  Ala Ala Gly Gly Ala  Val Cys Glu Gln Pro  Leu Gly Leu
    3485                 3490                 3495

Glu Cys  Arg Ala Gln Ala Gln  Pro Gly Val Pro Leu  Arg Glu Leu
    3500                 3505                 3510

Gly Gln  Val Val Glu Cys Ser  Leu Asp Phe Gly Leu  Val Cys Arg
    3515                 3520                 3525

Asn Arg  Glu Gln Val Gly Lys  Phe Lys Met Cys Phe  Asn Tyr Glu
    3530                 3535                 3540

Ile Arg  Val Phe Cys Cys Asn  Tyr Gly His Cys Pro  Ser Thr Pro
    3545                 3550                 3555

Ala Thr  Ser Ser Thr Ala Thr  Pro Ser Ser Thr Pro  Gly Thr Thr
    3560                 3565                 3570

Trp Ile  Leu Thr Glu Gln Thr  Thr Ala Ala Thr Thr  Thr Ala Thr
    3575                 3580                 3585

Thr Gly  Ser Thr Ala Ile Pro  Ser Ser Thr Pro Gly  Thr Ala Pro
    3590                 3595                 3600

Pro Pro  Lys Val Leu Thr Ser  Thr Ala Thr Thr Pro  Thr Ala Thr
    3605                 3610                 3615

Ser Ser  Lys Ala Thr Ser Ser  Ser Ser Pro Arg Thr  Ala Thr Thr
    3620                 3625                 3630

Leu Pro  Val Leu Thr Ser Thr  Ala Thr Lys Ser Thr  Ala Thr Ser
    3635                 3640                 3645

Phe Thr  Pro Ile Pro Ser Phe  Thr Leu Gly Thr Thr  Gly Thr Leu
    3650                 3655                 3660

Pro Glu  Gln Thr Thr Thr Pro  Met Ala Thr Met Ser  Thr Ile His
    3665                 3670                 3675

Pro Ser  Ser Thr Pro Glu Thr  Thr His Thr Ser Thr  Val Leu Thr
    3680                 3685                 3690

Thr Lys  Ala Thr Thr Thr Arg  Ala Thr Ser Ser Met  Ser Thr Pro
    3695                 3700                 3705

Ser Ser  Thr Pro Gly Thr Thr  Trp Ile Leu Thr Glu  Leu Thr Thr
    3710                 3715                 3720

Ala Ala  Thr Thr Thr Ala Ala  Thr Gly Pro Thr Ala  Thr Pro Ser
    3725                 3730                 3735

Ser Thr  Pro Gly Thr Thr Trp  Ile Leu Thr Glu Pro  Ser Thr Thr
    3740                 3745                 3750

Ala Thr  Val Thr Val Pro Thr  Gly Ser Thr Ala Thr  Ala Ser Ser
    3755                 3760                 3765

Thr Arg  Ala Thr Ala Gly Thr  Leu Lys Val Leu Thr  Ser Thr Ala
    3770                 3775                 3780

Thr Thr  Pro Thr Val Ile Ser  Ser Arg Ala Thr Pro  Ser Ser Ser
```

```
    3785                3790                3795

Pro Gly  Thr Ala Thr Ala Leu  Pro Ala Leu Arg Ser  Thr Ala Thr
    3800                3805                3810

Thr Pro  Thr Ala Thr Ser Val  Thr Ala Ile Pro Ser  Ser Ser Leu
    3815                3820                3825

Gly Thr  Ala Trp Thr Arg Leu  Ser Gln Thr Thr Thr  Pro Thr Ala
    3830                3835                3840

Thr Met  Ser Thr Ala Thr Pro  Ser Ser Thr Pro Glu  Thr Val His
    3845                3850                3855

Thr Ser  Thr Val Leu Thr Thr  Thr Thr Thr Thr Thr  Arg Ala Thr
    3860                3865                3870

Gly Ser  Val Ala Thr Pro Ser  Ser Thr Pro Gly Thr  Ala His Thr
    3875                3880                3885

Thr Lys  Val Pro Thr Thr Thr  Thr Thr Gly Phe Thr  Ala Thr Pro
    3890                3895                3900

Ser Ser  Ser Pro Gly Thr Ala  Leu Thr Pro Pro Val  Trp Ile Ser
    3905                3910                3915

Thr Thr  Thr Thr Pro Thr Thr  Arg Gly Ser Thr Val  Thr Pro Ser
    3920                3925                3930

Ser Ile  Pro Gly Thr Thr His  Thr Ala Thr Val Leu  Thr Thr Thr
    3935                3940                3945

Thr Thr  Thr Val Ala Thr Gly  Ser Met Ala Thr Pro  Ser Ser Ser
    3950                3955                3960

Thr Gln  Thr Ser Gly Thr Thr  His Thr Pro Pro Val  Pro Asn Thr
    3965                3970                3975

Thr Ala  Thr Thr His Gly Arg  Ser Leu Pro Pro Ser  Ser Pro His
    3980                3985                3990

Thr Val  Arg Thr Ala Trp Thr  Ser Ala Thr Ser Gly  Ile Leu Gly
    3995                4000                4005

Thr Thr  His Ile Thr Glu Pro  Ser Thr Val Thr Ser  His Thr Pro
    4010                4015                4020

Ala Ala  Thr Thr Ser Thr Thr  Gln His Ser Thr Pro  Ala Leu Ser
    4025                4030                4035

Ser Pro  His Pro Ser Ser Arg  Thr Thr Glu Ser Pro  Pro Ser Pro
    4040                4045                4050

Gly Thr  Thr Thr Pro Gly His  Thr Arg Gly Thr Ser  Arg Thr Thr
    4055                4060                4065

Ala Thr  Ala Thr Pro Ser Lys  Thr Arg Thr Ser Thr  Leu Leu Pro
    4070                4075                4080

Ser Ser  Pro Thr Ser Ala Pro  Ile Thr Thr Val Val  Thr Thr Gly
    4085                4090                4095

Cys Glu  Pro Gln Cys Ala Trp  Ser Glu Trp Leu Asp  Tyr Ser Tyr
    4100                4105                4110

Pro Met  Pro Gly Pro Ser Gly  Gly Asp Phe Asp Thr  Tyr Ser Asn
    4115                4120                4125

Ile Arg  Ala Ala Gly Gly Ala  Val Cys Glu Gln Pro  Leu Gly Leu
    4130                4135                4140

Glu Cys  Arg Ala Gln Ala Gln  Pro Gly Val Pro Leu  Arg Glu Leu
    4145                4150                4155

Gly Gln  Val Val Glu Cys Ser  Leu Asp Phe Gly Leu  Val Cys Arg
    4160                4165                4170

Asn Arg  Glu Gln Val Gly Lys  Phe Lys Met Cys Phe  Asn Tyr Glu
    4175                4180                4185
```

```
Ile Arg  Val Phe Cys Cys Asn  Tyr Gly His Cys Pro  Ser Thr Pro
    4190                 4195                 4200

Ala Thr  Ser Ser Thr Ala Thr  Pro Ser Ser Thr Pro  Gly Thr Thr
    4205                 4210                 4215

Trp Ile  Leu Thr Lys Leu Thr  Thr Thr Ala Thr Thr  Thr Glu Ser
    4220                 4225                 4230

Thr Gly  Ser Thr Ala Thr Pro  Ser Ser Thr Pro Gly  Thr Thr Trp
    4235                 4240                 4245

Ile Leu  Thr Glu Pro Ser Thr  Thr Ala Thr Val Thr  Val Pro Thr
    4250                 4255                 4260

Gly Ser  Thr Ala Thr Ala Ser  Ser Thr Gln Ala Thr  Ala Gly Thr
    4265                 4270                 4275

Pro His  Val Ser Thr Thr Ala  Thr Thr Pro Thr Val  Thr Ser Ser
    4280                 4285                 4290

Lys Ala  Thr Pro Phe Ser Ser  Pro Gly Thr Ala Thr  Ala Leu Pro
    4295                 4300                 4305

Ala Leu  Arg Ser Thr Ala Thr  Thr Pro Thr Ala Thr  Ser Phe Thr
    4310                 4315                 4320

Ala Ile  Pro Ser Ser Ser Leu  Gly Thr Thr Trp Thr  Arg Leu Ser
    4325                 4330                 4335

Gln Thr  Thr Thr Pro Thr Ala  Thr Met Ser Thr Ala  Thr Pro Ser
    4340                 4345                 4350

Ser Thr  Pro Glu Thr Ala His  Thr Ser Thr Val Leu  Thr Thr Thr
    4355                 4360                 4365

Ala Thr  Thr Thr Arg Ala Thr  Gly Ser Val Ala Thr  Pro Ser Ser
    4370                 4375                 4380

Thr Pro  Gly Thr Ala His Thr  Thr Lys Val Pro Thr  Thr Thr Thr
    4385                 4390                 4395

Thr Gly  Phe Thr Val Thr Pro  Ser Ser Ser Pro Gly  Thr Ala Arg
    4400                 4405                 4410

Thr Pro  Pro Val Trp Ile Ser  Thr Thr Thr Thr Pro  Thr Thr Ser
    4415                 4420                 4425

Gly Ser  Thr Val Thr Pro Ser  Ser Val Pro Gly Thr  Thr His Thr
    4430                 4435                 4440

Pro Thr  Val Leu Thr Thr Thr  Thr Thr Thr Val Ala  Thr Gly Ser
    4445                 4450                 4455

Met Ala  Thr Pro Ser Ser Ser  Thr Gln Thr Ser Gly  Thr Thr His
    4460                 4465                 4470

Thr Pro  Pro Val Pro Asn Thr  Thr Ala Thr Thr His  Gly Arg Ser
    4475                 4480                 4485

Leu Ser  Pro Ser Ser Pro His  Thr Val Arg Thr Ala  Trp Thr Ser
    4490                 4495                 4500

Ala Thr  Ser Gly Thr Leu Gly  Thr Thr His Ile Thr  Glu Pro Ser
    4505                 4510                 4515

Thr Gly  Thr Ser His Thr Pro  Ala Ala Thr Thr Gly  Thr Thr Gln
    4520                 4525                 4530

His Ser  Thr Pro Ala Leu Ser  Ser Pro His Pro Ser  Ser Arg Thr
    4535                 4540                 4545

Thr Glu  Ser Pro Pro Ser Pro  Gly Thr Thr Thr Pro  Gly His Thr
    4550                 4555                 4560

Thr Ala  Thr Ser Arg Thr Thr  Ala Thr Ala Thr Pro  Ser Lys Thr
    4565                 4570                 4575
```

```
Arg Thr  Ser Thr Leu Leu Pro  Ser Ser Pro Thr Ser  Ala Pro Ile
    4580                 4585                 4590

Thr Thr  Val Val Thr Thr Gly  Cys Glu Pro Gln Cys  Ala Trp Ser
    4595                 4600                 4605

Glu Trp  Leu Asp Tyr Ser Tyr  Pro Met Pro Gly Pro  Ser Gly Gly
    4610                 4615                 4620

Asp Phe  Asp Thr Tyr Ser Asn  Ile Arg Ala Ala Gly  Gly Ala Val
    4625                 4630                 4635

Cys Glu  Gln Pro Leu Gly Leu  Glu Cys Arg Ala Gln  Ala Gln Pro
    4640                 4645                 4650

Gly Val  Pro Leu Gly Glu Leu  Gly Gln Val Val Glu  Cys Ser Leu
    4655                 4660                 4665

Asp Phe  Gly Leu Val Cys Arg  Asn Arg Glu Gln Val  Gly Lys Phe
    4670                 4675                 4680

Lys Met  Cys Phe Asn Tyr Glu  Ile Arg Val Phe Cys  Cys Asn Tyr
    4685                 4690                 4695

Gly His  Cys Pro Ser Thr Pro  Ala Thr Ser Ser Thr  Ala Met Pro
    4700                 4705                 4710

Ser Ser  Thr Pro Gly Thr Thr  Trp Ile Leu Thr Glu  Leu Thr Thr
    4715                 4720                 4725

Thr Ala  Thr Thr Thr Ala Ser  Thr Gly Ser Thr Ala  Thr Pro Ser
    4730                 4735                 4740

Ser Thr  Pro Gly Thr Ala Pro  Pro Pro Lys Val Leu  Thr Ser Pro
    4745                 4750                 4755

Ala Thr  Thr Pro Thr Ala Thr  Ser Ser Lys Ala Thr  Ser Ser Ser
    4760                 4765                 4770

Ser Pro  Arg Thr Ala Thr Thr  Leu Pro Val Leu Thr  Ser Thr Ala
    4775                 4780                 4785

Thr Lys  Ser Thr Ala Thr Ser  Val Thr Pro Ile Pro  Ser Ser Thr
    4790                 4795                 4800

Leu Gly  Thr Thr Gly Thr Leu  Pro Glu Gln Thr Thr  Thr Pro Val
    4805                 4810                 4815

Ala Thr  Met Ser Thr Ile His  Pro Ser Ser Thr Pro  Glu Thr Thr
    4820                 4825                 4830

His Thr  Ser Thr Val Leu Thr  Thr Lys Ala Thr Thr  Thr Arg Ala
    4835                 4840                 4845

Thr Ser  Ser Thr Ser Thr Pro  Ser Ser Thr Pro Gly  Thr Thr Trp
    4850                 4855                 4860

Ile Leu  Thr Glu Leu Thr Thr  Ala Ala Thr Thr Thr  Ala Ala Thr
    4865                 4870                 4875

Gly Pro  Thr Ala Thr Pro Ser  Ser Thr Pro Gly Thr  Thr Trp Ile
    4880                 4885                 4890

Leu Thr  Glu Leu Thr Thr Thr  Ala Thr Thr Thr Ala  Ser Thr Gly
    4895                 4900                 4905

Ser Thr  Ala Thr Pro Ser Ser  Thr Pro Gly Thr Thr  Trp Ile Leu
    4910                 4915                 4920

Thr Glu  Pro Ser Thr Thr Ala  Thr Val Thr Val Pro  Thr Gly Ser
    4925                 4930                 4935

Thr Ala  Thr Ala Ser Ser Thr  Gln Ala Thr Ala Gly  Thr Pro His
    4940                 4945                 4950

Val Ser  Thr Thr Ala Thr Thr  Pro Thr Val Thr Ser  Ser Lys Ala
    4955                 4960                 4965

Thr Pro  Ser Ser Ser Pro Gly  Thr Ala Thr Ala Leu  Pro Ala Leu
```

```
    4970                4975                4980

Arg Ser  Thr Ala Thr Thr Pro  Thr Ala Thr Ser Phe  Thr Ala Ile
    4985                4990                4995

Pro Ser  Ser Ser Leu Gly Thr  Thr Trp Thr Arg Leu  Ser Gln Thr
    5000                5005                5010

Thr Thr  Pro Thr Ala Thr Met  Ser Thr Ala Thr Pro  Ser Ser Thr
    5015                5020                5025

Pro Glu  Thr Val His Thr Ser  Thr Val Leu Thr Ala  Thr Ala Thr
    5030                5035                5040

Thr Thr  Gly Ala Thr Gly Ser  Val Ala Thr Pro Ser  Ser Thr Pro
    5045                5050                5055

Gly Thr  Ala His Thr Thr Lys  Val Pro Thr Thr Thr  Thr Thr Gly
    5060                5065                5070

Phe Thr  Ala Thr Pro Ser Ser  Ser Pro Gly Thr Ala  Leu Thr Pro
    5075                5080                5085

Pro Thr  Thr Thr Pro Met Ser  Thr Met Ser Thr Ile  His Thr Ser
    5090                5095                5100

Ser Thr  Pro Glu Thr Thr His  Thr Ser Thr Val Leu  Thr Thr Thr
    5105                5110                5115

Ala Thr  Met Thr Arg Ala Thr  Asn Ser Thr Ala Thr  Pro Ser Ser
    5120                5125                5130

Thr Leu  Gly Thr Thr Arg Ile  Leu Thr Glu Leu Thr  Thr Thr Ala
    5135                5140                5145

Thr Thr  Thr Ala Ala Thr Gly  Ser Thr Ala Thr Leu  Ser Ser Thr
    5150                5155                5160

Pro Gly  Thr Thr Trp Ile Leu  Thr Glu Pro Ser Thr  Ile Ala Thr
    5165                5170                5175

Val Met  Val Pro Thr Gly Ser  Thr Ala Thr Ala Ser  Ser Thr Leu
    5180                5185                5190

Gly Thr  Ala His Thr Pro Lys  Val Val Thr Thr Met  Ala Thr Met
    5195                5200                5205

Pro Thr  Ala Thr Ala Ser Thr  Val Pro Ser Ser Ser  Thr Val Gly
    5210                5215                5220

Thr Thr  Arg Thr Pro Ala Val  Leu Pro Ser Ser Leu  Pro Thr Phe
    5225                5230                5235

Ser Val  Ser Thr Val Ser Ser  Ser Val Leu Thr Thr  Leu Arg Pro
    5240                5245                5250

Thr Gly  Phe Pro Ser Ser His  Phe Ser Thr Pro Cys  Phe Cys Arg
    5255                5260                5265

Ala Phe  Gly Gln Phe Phe Ser  Pro Gly Glu Val Ile  Tyr Asn Lys
    5270                5275                5280

Thr Asp  Arg Ala Gly Cys His  Phe Tyr Ala Val Cys  Asn Gln His
    5285                5290                5295

Cys Asp  Ile Asp Arg Phe Gln  Gly Ala Cys Pro Thr  Ser Pro Pro
    5300                5305                5310

Pro Val  Ser Ser Ala Pro Leu  Ser Ser Pro Ser Pro  Ala Pro Gly
    5315                5320                5325

Cys Asp  Asn Ala Ile Pro Leu  Arg Gln Val Asn Glu  Thr Trp Thr
    5330                5335                5340

Leu Glu  Asn Cys Thr Val Ala  Arg Cys Val Gly Asp  Asn Arg Val
    5345                5350                5355

Val Leu  Leu Asp Pro Lys Pro  Val Ala Asn Val Thr  Cys Val Asn
    5360                5365                5370
```

```
Lys His Leu Pro Ile Lys Val Ser Asp Pro Ser Gln Pro Cys Asp
    5375                5380                5385

Phe His Tyr Glu Cys Glu Cys Glu Cys Val Gly Gly Arg Gly Ile
    5390                5395                5400

Thr Pro Gly Ala Gly Ile Cys Ser Met Trp Gly Gly Ser His Tyr
    5405                5410                5415

Ser Thr Phe Asp Gly Thr Ser Tyr Thr Phe Arg Gly Asn Cys Thr
    5420                5425                5430

Tyr Val Leu Met Arg Glu Ile His Ala Arg Phe Gly Asn Leu Ser
    5435                5440                5445

Leu Tyr Leu Asp Asn His Tyr Cys Thr Ala Ser Ala Thr Ala Ala
    5450                5455                5460

Ala Ala Ala Ala Arg Cys Pro Arg Ala Leu Ser Ile His Tyr Lys
    5465                5470                5475

Ser Met Asp Ile Val Leu Thr Val Thr Met Val His Gly Lys Glu
    5480                5485                5490

Glu Gly Leu Ile Leu Phe Asp Gln Ile Pro Val Ser Ser Gly Phe
    5495                5500                5505

Ser Lys Asn Gly Val Leu Val Ser Val Leu Gly Thr Thr Thr Met
    5510                5515                5520

Arg Val Asp Ile Pro Ala Leu Gly Val Ser Val Thr Phe Asn Gly
    5525                5530                5535

Gln Val Phe Gln Ala Arg Leu Pro Tyr Ser Leu Phe His Asn Asn
    5540                5545                5550

Thr Glu Gly Gln Cys Gly Thr Cys Thr Asn Asn Gln Arg Asp Asp
    5555                5560                5565

Cys Leu Gln Arg Asp Gly Thr Thr Ala Ala Ser Cys Lys Asp Met
    5570                5575                5580

Ala Lys Thr Trp Leu Val Pro Asp Ser Arg Lys Asp Gly Cys Trp
    5585                5590                5595

Ala Pro Thr Gly Thr Pro Pro Thr Ala Ser Pro Ala Ala Pro Val
    5600                5605                5610

Ser Ser Thr Pro Thr Pro Thr Pro Cys Pro Pro Gln Pro Leu Cys
    5615                5620                5625

Asp Leu Met Leu Ser Gln Val Phe Ala Glu Cys His Asn Leu Val
    5630                5635                5640

Pro Pro Gly Pro Phe Phe Asn Ala Cys Ile Ser Asp His Cys Arg
    5645                5650                5655

Gly Arg Leu Glu Val Pro Cys Gln Ser Leu Glu Ala Tyr Ala Glu
    5660                5665                5670

Leu Cys Arg Ala Arg Gly Val Cys Ser Asp Trp Arg Gly Ala Thr
    5675                5680                5685

Gly Gly Leu Cys Asp Leu Thr Cys Pro Pro Thr Lys Val Tyr Lys
    5690                5695                5700

Pro Cys Gly Pro Ile Gln Pro Ala Thr Cys Asn Ser Arg Asn Gln
    5705                5710                5715

Ser Pro Gln Leu Glu Gly Met Ala Glu Gly Cys Phe Cys Pro Glu
    5720                5725                5730

Asp Gln Ile Leu Phe Asn Ala His Met Gly Ile Cys Val Gln Ala
    5735                5740                5745

Cys Pro Cys Val Gly Pro Asp Gly Phe Pro Lys Phe Pro Gly Glu
    5750                5755                5760
```

```
Arg Trp  Val Ser Asn Cys Gln  Ser Cys Val Cys Asp  Glu Gly Ser
    5765                 5770                 5775

Val Ser  Val Gln Cys Lys Pro  Leu Pro Cys Asp Ala  Gln Gly Gln
    5780                 5785                 5790

Pro Pro  Pro Cys Asn Arg Pro  Gly Phe Val Thr Val  Thr Arg Pro
    5795                 5800                 5805

Arg Ala  Glu Asn Pro Cys Cys  Pro Glu Thr Val Cys  Val Cys Asn
    5810                 5815                 5820

Thr Thr  Thr Cys Pro Gln Ser  Leu Pro Val Cys Pro  Pro Gly Gln
    5825                 5830                 5835

Glu Ser  Ile Cys Thr Gln Glu  Glu Gly Asp Cys Cys  Pro Thr Phe
    5840                 5845                 5850

Arg Cys  Arg Pro Gln Leu Cys  Ser Tyr Asn Gly Thr  Phe Tyr Gly
    5855                 5860                 5865

Val Gly  Ala Thr Phe Pro Gly  Ala Leu Pro Cys His  Met Cys Thr
    5870                 5875                 5880

Cys Leu  Ser Gly Asp Thr Gln  Asp Pro Thr Val Gln  Cys Gln Glu
    5885                 5890                 5895

Asp Ala  Cys Asn Asn Thr Thr  Cys Pro Gln Gly Phe  Glu Tyr Lys
    5900                 5905                 5910

Arg Val  Ala Gly Gln Cys Cys  Gly Glu Cys Val Gln  Thr Ala Cys
    5915                 5920                 5925

Leu Thr  Pro Asp Gly Gln Pro  Val Gln Leu Asn Glu  Thr Trp Val
    5930                 5935                 5940

Asn Ser  His Val Asp Asn Cys  Thr Val Tyr Leu Cys  Glu Ala Glu
    5945                 5950                 5955

Gly Gly  Val His Leu Leu Thr  Pro Gln Pro Ala Ser  Cys Pro Asp
    5960                 5965                 5970

Val Ser  Ser Cys Arg Gly Ser  Leu Arg Lys Thr Gly  Cys Cys Tyr
    5975                 5980                 5985

Ser Cys  Glu Glu Asp Ser Cys  Gln Val Arg Ile Asn  Thr Thr Ile
    5990                 5995                 6000

Leu Trp  His Gln Gly Cys Glu  Thr Glu Val Asn Ile  Thr Phe Cys
    6005                 6010                 6015

Glu Gly  Ser Cys Pro Gly Ala  Ser Lys Tyr Ser Ala  Glu Ala Gln
    6020                 6025                 6030

Ala Met  Gln His Gln Cys Thr  Cys Cys Gln Glu Arg  Arg Val His
    6035                 6040                 6045

Glu Glu  Thr Val Pro Leu His  Cys Pro Asn Gly Ser  Ala Ile Leu
    6050                 6055                 6060

His Thr  Tyr Thr His Ala Val  Gln Val Leu Cys Gly  Leu Leu Ala
    6065                 6070                 6075

Trp Gly  Leu Gln Ala Gly Gly  His Ile Arg Gly Ala  Val Gln Asp
    6080                 6085                 6090

Pro Gln  Gln Pro Leu Lys Asp  Gln Glu Ala Ser Gly  Lys Ala Arg
    6095                 6100                 6105

Gln Gly  Gly Gly Tyr Arg Gln  Thr Val Ala Trp Gly  Asp Lys Ser
    6110                 6115                 6120

Asn Ala  Arg Ala Trp Leu Gln  Lys Pro Val Val Trp  Val Gln Ser
    6125                 6130                 6135

Gly Ala  Phe Pro Thr Pro Gly  Pro Ala Ser Ala Leu  Cys Pro Trp
    6140                 6145                 6150

Lys Met  Gly Ile Gln Pro Glu  Thr Thr Lys Gln Leu  Arg Asp Ala
```

```
    6155                6160                6165

Asn Ile  Leu Lys Glu Ser Lys  Arg Ser Ile Ser Arg  Glu Arg Gln
    6170                6175                6180

Arg Gln  Cys Ala Gln Ala Ile  Arg Phe Asn Arg Gly  Phe Gly Gly
    6185                6190                6195

Gln Ile  Trp Lys Ser Gln Arg  Phe Phe
    6200                6205


<210> SEQ ID NO 10
<211> LENGTH: 4493
<212> TYPE: PRT
<213> ORGANISM: Human

<400> SEQUENCE: 10

Met Pro Arg Pro Gly Thr Met Ala Leu Cys Leu Leu Thr Leu Val Leu
1               5                   10                  15

Ser Leu Leu Pro Pro Gln Ala Ala Ala Glu Gln Asp Leu Ser Val Asn
            20                  25                  30

Arg Ala Val Trp Asp Gly Gly Gly Cys Ile Ser Gln Gly Asp Val Leu
        35                  40                  45

Asn Arg Gln Cys Gln Gln Leu Ser Gln His Val Arg Thr Gly Ser Ala
    50                  55                  60

Ala Asn Thr Ala Thr Gly Thr Thr Ser Thr Asn Val Val Glu Pro Arg
65                  70                  75                  80

Met Tyr Leu Ser Cys Ser Thr Asn Pro Glu Met Thr Ser Ile Glu Ser
                85                  90                  95

Ser Val Thr Ser Asp Thr Pro Gly Val Ser Ser Thr Arg Met Thr Pro
            100                 105                 110

Thr Glu Ser Arg Thr Thr Ser Glu Ser Thr Ser Asp Ser Thr Thr Leu
        115                 120                 125

Phe Pro Ser Ser Thr Glu Asp Thr Ser Ser Pro Thr Thr Pro Glu Gly
    130                 135                 140

Thr Asp Val Pro Met Ser Thr Pro Ser Glu Glu Ser Ile Ser Ser Thr
145                 150                 155                 160

Met Ala Phe Val Ser Thr Ala Pro Leu Pro Ser Phe Glu Ala Tyr Thr
                165                 170                 175

Ser Leu Thr Tyr Lys Val Asp Met Ser Thr Pro Leu Thr Thr Ser Thr
            180                 185                 190

Gln Ala Ser Ser Ser Pro Thr Thr Pro Glu Ser Thr Thr Ile Pro Lys
        195                 200                 205

Ser Thr Asn Ser Glu Gly Ser Thr Pro Leu Thr Ser Met Pro Ala Ser
    210                 215                 220

Thr Met Lys Val Ala Ser Ser Glu Ala Ile Thr Leu Leu Thr Thr Pro
225                 230                 235                 240

Val Glu Ile Ser Thr Pro Val Thr Ile Ser Ala Gln Ala Ser Ser Ser
                245                 250                 255

Pro Thr Thr Ala Glu Gly Pro Ser Leu Ser Asn Ser Ala Pro Ser Gly
            260                 265                 270

Gly Ser Thr Pro Leu Thr Arg Met Pro Leu Ser Val Met Leu Val Val
        275                 280                 285

Ser Ser Glu Ala Ser Thr Leu Ser Thr Thr Pro Ala Ala Thr Asn Ile
    290                 295                 300

Pro Val Ile Thr Ser Thr Glu Ala Ser Ser Ser Pro Thr Thr Ala Glu
305                 310                 315                 320
```

```
Gly Thr Ser Ile Pro Thr Ser Thr Tyr Thr Glu Gly Ser Thr Pro Leu
                325                 330                 335

Thr Ser Thr Pro Ala Ser Thr Met Pro Val Ala Thr Ser Glu Met Ser
            340                 345                 350

Thr Leu Ser Ile Thr Pro Val Asp Thr Ser Thr Leu Val Thr Thr Ser
        355                 360                 365

Thr Glu Pro Ser Ser Leu Pro Thr Thr Ala Glu Ala Thr Ser Met Leu
    370                 375                 380

Thr Ser Thr Leu Ser Glu Gly Ser Thr Pro Leu Thr Asn Met Pro Val
385                 390                 395                 400

Ser Thr Ile Leu Val Ala Ser Ser Glu Ala Ser Thr Thr Ser Thr Ile
                405                 410                 415

Pro Val Asp Ser Lys Thr Phe Val Thr Thr Ala Ser Glu Ala Ser Ser
            420                 425                 430

Ser Pro Thr Thr Ala Glu Asp Thr Ser Ile Ala Thr Ser Thr Pro Ser
        435                 440                 445

Glu Gly Ser Thr Pro Leu Thr Ser Met Pro Val Ser Thr Thr Pro Val
    450                 455                 460

Ala Ser Ser Glu Ala Ser Asn Leu Ser Thr Thr Pro Val Asp Ser Lys
465                 470                 475                 480

Thr Gln Val Thr Thr Ser Thr Glu Ala Ser Ser Ser Pro Pro Thr Ala
                485                 490                 495

Glu Val Asn Ser Met Pro Thr Ser Thr Pro Ser Glu Gly Ser Thr Pro
            500                 505                 510

Leu Thr Ser Met Ser Val Ser Thr Met Pro Val Ala Ser Ser Glu Ala
        515                 520                 525

Ser Thr Leu Ser Thr Thr Pro Val Asp Thr Ser Thr Pro Val Thr Thr
    530                 535                 540

Ser Ser Glu Ala Ser Ser Ser Ser Thr Thr Pro Glu Gly Thr Ser Ile
545                 550                 555                 560

Pro Thr Ser Thr Pro Ser Glu Gly Ser Thr Pro Leu Thr Asn Met Pro
                565                 570                 575

Val Ser Thr Arg Leu Val Val Ser Ser Glu Ala Ser Thr Thr Ser Thr
            580                 585                 590

Thr Pro Ala Asp Ser Asn Thr Phe Val Thr Thr Ser Ser Glu Ala Ser
        595                 600                 605

Ser Ser Ser Thr Thr Ala Glu Gly Thr Ser Met Pro Thr Ser Thr Tyr
    610                 615                 620

Ser Glu Arg Gly Thr Thr Ile Thr Ser Met Ser Val Ser Thr Thr Leu
625                 630                 635                 640

Val Ala Ser Ser Glu Ala Ser Thr Leu Ser Thr Thr Pro Val Asp Ser
                645                 650                 655

Asn Thr Pro Val Thr Thr Ser Thr Glu Ala Thr Ser Ser Ser Thr Thr
            660                 665                 670

Ala Glu Gly Thr Ser Met Pro Thr Ser Thr Tyr Thr Glu Gly Ser Thr
        675                 680                 685

Pro Leu Thr Ser Met Pro Val Asn Thr Thr Leu Val Ala Ser Ser Glu
    690                 695                 700

Ala Ser Thr Leu Ser Thr Thr Pro Val Asp Thr Ser Thr Pro Val Thr
705                 710                 715                 720

Thr Ser Thr Glu Ala Ser Ser Ser Pro Thr Thr Ala Asp Gly Ala Ser
                725                 730                 735

Met Pro Thr Ser Thr Pro Ser Glu Gly Ser Thr Pro Leu Thr Ser Met
```

```
            740                 745                 750

Pro Val Ser Lys Thr Leu Leu Thr Ser Ser Glu Ala Ser Thr Leu Ser
        755                 760                 765

Thr Thr Pro Leu Asp Thr Ser Thr His Ile Thr Thr Ser Thr Glu Ala
    770                 775                 780

Ser Cys Ser Pro Thr Thr Thr Glu Gly Thr Ser Met Pro Ile Ser Thr
785                 790                 795                 800

Pro Ser Glu Gly Ser Pro Leu Leu Thr Ser Ile Pro Val Ser Ile Thr
                805                 810                 815

Pro Val Thr Ser Pro Glu Ala Ser Thr Leu Ser Thr Thr Pro Val Asp
            820                 825                 830

Ser Asn Ser Pro Val Thr Thr Ser Thr Glu Val Ser Ser Ser Pro Thr
        835                 840                 845

Pro Ala Glu Gly Thr Ser Met Pro Thr Ser Thr Tyr Ser Glu Gly Arg
    850                 855                 860

Thr Pro Leu Thr Ser Met Pro Val Ser Thr Thr Leu Val Ala Thr Ser
865                 870                 875                 880

Ala Ile Ser Thr Leu Ser Thr Thr Pro Val Asp Thr Ser Thr Pro Val
                885                 890                 895

Thr Asn Ser Thr Glu Ala Arg Ser Ser Pro Thr Thr Ser Glu Gly Thr
            900                 905                 910

Ser Met Pro Thr Ser Thr Pro Gly Glu Gly Ser Thr Pro Leu Thr Ser
        915                 920                 925

Met Pro Asp Ser Thr Thr Pro Val Val Ser Ser Glu Ala Arg Thr Leu
    930                 935                 940

Ser Ala Thr Pro Val Asp Thr Ser Thr Pro Val Thr Thr Ser Thr Glu
945                 950                 955                 960

Ala Thr Ser Ser Pro Thr Thr Ala Glu Gly Thr Ser Ile Pro Thr Ser
                965                 970                 975

Thr Pro Ser Glu Gly Thr Thr Pro Leu Thr Ser Thr Pro Val Ser His
            980                 985                 990

Thr Leu Val Ala Asn Ser Glu Ala  Ser Thr Leu Ser Thr  Thr Pro Val
        995                 1000                1005

Asp Ser  Asn Thr Pro Leu Thr  Thr Ser Thr Glu Ala  Ser Ser Pro
    1010                1015                1020

Pro Pro  Thr Ala Glu Gly Thr  Ser Met Pro Thr Ser  Thr Pro Ser
    1025                1030                1035

Glu Gly  Ser Thr Pro Leu Thr  Arg Met Pro Val Ser  Thr Thr Met
    1040                1045                1050

Val Ala  Ser Ser Glu Thr Ser  Thr Leu Ser Thr Thr  Pro Ala Asp
    1055                1060                1065

Thr Ser  Thr Pro Val Thr Thr  Tyr Ser Gln Ala Ser  Ser Ser Ser
    1070                1075                1080

Thr Thr  Ala Asp Gly Thr Ser  Met Pro Thr Ser Thr  Tyr Ser Glu
    1085                1090                1095

Gly Ser  Thr Pro Leu Thr Ser  Val Pro Val Ser Thr  Arg Leu Val
    1100                1105                1110

Val Ser  Ser Glu Ala Ser Thr  Leu Ser Thr Thr Pro  Val Asp Thr
    1115                1120                1125

Ser Ile  Pro Val Thr Thr Ser  Thr Glu Ala Ser Ser  Ser Pro Thr
    1130                1135                1140

Thr Ala  Glu Gly Thr Ser Ile  Pro Thr Ser Pro Pro  Ser Glu Gly
    1145                1150                1155
```

```
Thr Thr  Pro Leu Ala Ser Met  Pro Val Ser Thr Thr  Leu Val Val
    1160                 1165                 1170

Ser Ser  Glu Ala Asn Thr Leu  Ser Thr Thr Pro Val  Asp Ser Lys
    1175                 1180                 1185

Thr Gln  Val Ala Thr Ser Thr  Glu Ala Ser Ser Pro  Pro Pro Thr
    1190                 1195                 1200

Ala Glu  Val Thr Ser Met Pro  Thr Ser Thr Pro Gly  Glu Arg Ser
    1205                 1210                 1215

Thr Pro  Leu Thr Ser Met Pro  Val Arg His Thr Pro  Val Ala Ser
    1220                 1225                 1230

Ser Glu  Ala Ser Thr Leu Ser  Thr Ser Pro Val Asp  Thr Ser Thr
    1235                 1240                 1245

Pro Val  Thr Thr Ser Ala Glu  Thr Ser Ser Ser Pro  Thr Thr Ala
    1250                 1255                 1260

Glu Gly  Thr Ser Leu Pro Thr  Ser Thr Thr Ser Glu  Gly Ser Thr
    1265                 1270                 1275

Leu Leu  Thr Ser Ile Pro Val  Ser Thr Thr Leu Val  Thr Ser Pro
    1280                 1285                 1290

Glu Ala  Ser Thr Leu Leu Thr  Thr Pro Val Asp Thr  Lys Gly Pro
    1295                 1300                 1305

Val Val  Thr Ser Asn Glu Val  Ser Ser Ser Pro Thr  Pro Ala Glu
    1310                 1315                 1320

Gly Thr  Ser Met Pro Thr Ser  Thr Tyr Ser Glu Gly  Arg Thr Pro
    1325                 1330                 1335

Leu Thr  Ser Ile Pro Val Asn  Thr Thr Leu Val Ala  Ser Ser Ala
    1340                 1345                 1350

Ile Ser  Ile Leu Ser Thr Thr  Pro Val Asp Asn Ser  Thr Pro Val
    1355                 1360                 1365

Thr Thr  Ser Thr Glu Ala Cys  Ser Ser Pro Thr Thr  Ser Glu Gly
    1370                 1375                 1380

Thr Ser  Met Pro Asn Ser Asn  Pro Ser Glu Gly Thr  Thr Pro Leu
    1385                 1390                 1395

Thr Ser  Ile Pro Val Ser Thr  Thr Pro Val Val Ser  Ser Glu Ala
    1400                 1405                 1410

Ser Thr  Leu Ser Ala Thr Pro  Val Asp Thr Ser Thr  Pro Gly Thr
    1415                 1420                 1425

Thr Ser  Ala Glu Ala Thr Ser  Ser Pro Thr Thr Ala  Glu Gly Ile
    1430                 1435                 1440

Ser Ile  Pro Thr Ser Thr Pro  Ser Glu Gly Lys Thr  Pro Leu Lys
    1445                 1450                 1455

Ser Ile  Pro Val Ser Asn Thr  Pro Val Ala Asn Ser  Glu Ala Ser
    1460                 1465                 1470

Thr Leu  Ser Thr Thr Pro Val  Asp Ser Asn Ser Pro  Val Val Thr
    1475                 1480                 1485

Ser Thr  Ala Val Ser Ser Ser  Pro Thr Pro Ala Glu  Gly Thr Ser
    1490                 1495                 1500

Ile Ala  Ile Ser Thr Pro Ser  Glu Gly Ser Thr Ala  Leu Thr Ser
    1505                 1510                 1515

Ile Pro  Val Ser Thr Thr Thr  Val Ala Ser Ser Glu  Ile Asn Ser
    1520                 1525                 1530

Leu Ser  Thr Thr Pro Ala Val  Thr Ser Thr Pro Val  Thr Thr Tyr
    1535                 1540                 1545
```

```
Ser Gln Ala Ser Ser Ser Pro Thr Thr Ala Asp Gly Thr Ser Met
    1550                1555                1560

Gln Thr Ser Thr Tyr Ser Glu Gly Ser Thr Pro Leu Thr Ser Leu
    1565                1570                1575

Pro Val Ser Thr Met Leu Val Val Ser Ser Glu Ala Asn Thr Leu
    1580                1585                1590

Ser Thr Thr Pro Ile Asp Ser Lys Thr Gln Val Thr Ala Ser Thr
    1595                1600                1605

Glu Ala Ser Ser Ser Thr Thr Ala Glu Gly Ser Ser Met Thr Ile
    1610                1615                1620

Ser Thr Pro Ser Glu Gly Ser Pro Leu Leu Thr Ser Ile Pro Val
    1625                1630                1635

Ser Thr Thr Pro Val Ala Ser Pro Glu Ala Ser Thr Leu Ser Thr
    1640                1645                1650

Thr Pro Val Asp Ser Asn Ser Pro Val Ile Thr Ser Thr Glu Val
    1655                1660                1665

Ser Ser Ser Pro Thr Pro Ala Glu Gly Thr Ser Met Pro Thr Ser
    1670                1675                1680

Thr Tyr Thr Glu Gly Arg Thr Pro Leu Thr Ser Ile Thr Val Arg
    1685                1690                1695

Thr Thr Pro Val Ala Ser Ser Ala Ile Ser Thr Leu Ser Thr Thr
    1700                1705                1710

Pro Val Asp Asn Ser Thr Pro Val Thr Thr Ser Thr Glu Ala Arg
    1715                1720                1725

Ser Ser Pro Thr Thr Ser Glu Gly Thr Ser Met Pro Asn Ser Thr
    1730                1735                1740

Pro Ser Glu Gly Thr Thr Pro Leu Thr Ser Ile Pro Val Ser Thr
    1745                1750                1755

Thr Pro Val Leu Ser Ser Glu Ala Ser Thr Leu Ser Ala Thr Pro
    1760                1765                1770

Ile Asp Thr Ser Thr Pro Val Thr Thr Ser Thr Glu Ala Thr Ser
    1775                1780                1785

Ser Pro Thr Thr Ala Glu Gly Thr Ser Ile Pro Thr Ser Thr Leu
    1790                1795                1800

Ser Glu Gly Met Thr Pro Leu Thr Ser Thr Pro Val Ser His Thr
    1805                1810                1815

Leu Val Ala Asn Ser Glu Ala Ser Thr Leu Ser Thr Thr Pro Val
    1820                1825                1830

Asp Ser Asn Ser Pro Val Val Thr Ser Thr Ala Val Ser Ser Ser
    1835                1840                1845

Pro Thr Pro Ala Glu Gly Thr Ser Ile Ala Thr Ser Thr Pro Ser
    1850                1855                1860

Glu Gly Ser Thr Ala Leu Thr Ser Ile Pro Val Ser Thr Thr Thr
    1865                1870                1875

Val Ala Ser Ser Glu Thr Asn Thr Leu Ser Thr Thr Pro Ala Val
    1880                1885                1890

Thr Ser Thr Pro Val Thr Thr Tyr Ala Gln Val Ser Ser Ser Pro
    1895                1900                1905

Thr Thr Ala Asp Gly Ser Ser Met Pro Thr Ser Thr Pro Arg Glu
    1910                1915                1920

Gly Arg Pro Pro Leu Thr Ser Ile Pro Val Ser Thr Thr Thr Val
    1925                1930                1935

Ala Ser Ser Glu Ile Asn Thr Leu Ser Thr Thr Leu Ala Asp Thr
```

```
    1940                1945                1950

Arg Thr  Pro Val Thr Thr Tyr  Ser Gln Ala Ser Ser  Ser Pro Thr
    1955                1960                1965

Thr Ala  Asp Gly Thr Ser Met  Pro Thr Pro Ala Tyr  Ser Glu Gly
    1970                1975                1980

Ser Thr  Pro Leu Thr Ser Met  Pro Leu Ser Thr Thr  Leu Val Val
    1985                1990                1995

Ser Ser  Glu Ala Ser Thr Leu  Ser Thr Thr Pro Val  Asp Thr Ser
    2000                2005                2010

Thr Pro  Ala Thr Thr Ser Thr  Glu Gly Ser Ser Ser  Pro Thr Thr
    2015                2020                2025

Ala Gly  Gly Thr Ser Ile Gln  Thr Ser Thr Pro Ser  Glu Arg Thr
    2030                2035                2040

Thr Pro  Leu Ala Gly Met Pro  Val Ser Thr Thr Leu  Val Val Ser
    2045                2050                2055

Ser Glu  Gly Asn Thr Leu Ser  Thr Thr Pro Val Asp  Ser Lys Thr
    2060                2065                2070

Gln Val  Thr Asn Ser Thr Glu  Ala Ser Ser Ser Ala  Thr Ala Glu
    2075                2080                2085

Gly Ser  Ser Met Thr Ile Ser  Ala Pro Ser Glu Gly  Ser Pro Leu
    2090                2095                2100

Leu Thr  Ser Ile Pro Leu Ser  Thr Thr Pro Val Ala  Ser Pro Glu
    2105                2110                2115

Ala Ser  Thr Leu Ser Thr Thr  Pro Val Asp Ser Asn  Ser Pro Val
    2120                2125                2130

Ile Thr  Ser Thr Glu Val Ser  Ser Ser Pro Ile Pro  Thr Glu Gly
    2135                2140                2145

Thr Ser  Met Gln Thr Ser Thr  Tyr Ser Asp Arg Arg  Thr Pro Leu
    2150                2155                2160

Thr Ser  Met Pro Val Ser Thr  Thr Val Val Ala Ser  Ser Ala Ile
    2165                2170                2175

Ser Thr  Leu Ser Thr Thr Pro  Val Asp Thr Ser Thr  Pro Val Thr
    2180                2185                2190

Asn Ser  Thr Glu Ala Arg Ser  Ser Pro Thr Thr Ser  Glu Gly Thr
    2195                2200                2205

Ser Met  Pro Thr Ser Thr Pro  Ser Glu Gly Ser Thr  Pro Phe Thr
    2210                2215                2220

Ser Met  Pro Val Ser Thr Met  Pro Val Val Thr Ser  Glu Ala Ser
    2225                2230                2235

Thr Leu  Ser Ala Thr Pro Val  Asp Thr Ser Thr Pro  Val Thr Thr
    2240                2245                2250

Ser Thr  Glu Ala Thr Ser Ser  Pro Thr Thr Ala Glu  Gly Thr Ser
    2255                2260                2265

Ile Pro  Thr Ser Thr Leu Ser  Glu Gly Thr Thr Pro  Leu Thr Ser
    2270                2275                2280

Ile Pro  Val Ser His Thr Leu  Val Ala Asn Ser Glu  Val Ser Thr
    2285                2290                2295

Leu Ser  Thr Thr Pro Val Asp  Ser Asn Thr Pro Phe  Thr Thr Ser
    2300                2305                2310

Thr Glu  Ala Ser Ser Pro Pro  Pro Thr Ala Glu Gly  Thr Ser Met
    2315                2320                2325

Pro Thr  Ser Thr Ser Ser Glu  Gly Asn Thr Pro Leu  Thr Arg Met
    2330                2335                2340
```

```
Pro Val Ser Thr Thr Met Val Ala Ser Phe Glu Thr Ser Thr Leu
    2345                2350                2355

Ser Thr Thr Pro Ala Asp Thr Ser Thr Pro Val Thr Thr Tyr Ser
    2360                2365                2370

Gln Ala Gly Ser Ser Pro Thr Thr Ala Asp Asp Thr Ser Met Pro
    2375                2380                2385

Thr Ser Thr Tyr Ser Glu Gly Ser Thr Pro Leu Thr Ser Val Pro
    2390                2395                2400

Val Ser Thr Met Pro Val Val Ser Ser Glu Ala Ser Thr His Ser
    2405                2410                2415

Thr Thr Pro Val Asp Thr Ser Thr Pro Val Thr Thr Ser Thr Glu
    2420                2425                2430

Ala Ser Ser Ser Pro Thr Thr Ala Glu Gly Thr Ser Ile Pro Thr
    2435                2440                2445

Ser Pro Pro Ser Glu Gly Thr Thr Pro Leu Ala Ser Met Pro Val
    2450                2455                2460

Ser Thr Thr Pro Val Val Ser Ser Glu Ala Gly Thr Leu Ser Thr
    2465                2470                2475

Thr Pro Val Asp Thr Ser Thr Pro Met Thr Thr Ser Thr Glu Ala
    2480                2485                2490

Ser Ser Ser Pro Thr Thr Ala Glu Asp Ile Val Val Pro Ile Ser
    2495                2500                2505

Thr Ala Ser Glu Gly Ser Thr Leu Leu Thr Ser Ile Pro Val Ser
    2510                2515                2520

Thr Thr Pro Val Ala Ser Pro Glu Ala Ser Thr Leu Ser Thr Thr
    2525                2530                2535

Pro Val Asp Ser Asn Ser Pro Val Val Thr Ser Thr Glu Ile Ser
    2540                2545                2550

Ser Ser Ala Thr Ser Ala Glu Gly Thr Ser Met Pro Thr Ser Thr
    2555                2560                2565

Tyr Ser Glu Gly Ser Thr Pro Leu Arg Ser Met Pro Val Ser Thr
    2570                2575                2580

Lys Pro Leu Ala Ser Ser Glu Ala Ser Thr Leu Ser Thr Thr Pro
    2585                2590                2595

Val Asp Thr Ser Ile Pro Val Thr Thr Ser Thr Glu Thr Ser Ser
    2600                2605                2610

Ser Pro Thr Thr Ala Lys Asp Thr Ser Met Pro Ile Ser Thr Pro
    2615                2620                2625

Ser Glu Val Ser Thr Ser Leu Thr Ser Ile Leu Val Ser Thr Met
    2630                2635                2640

Pro Val Ala Ser Ser Glu Ala Ser Thr Leu Ser Thr Thr Pro Val
    2645                2650                2655

Asp Thr Arg Thr Leu Val Thr Thr Ser Thr Gly Thr Ser Ser Ser
    2660                2665                2670

Pro Thr Thr Ala Glu Gly Ser Ser Met Pro Thr Ser Thr Pro Gly
    2675                2680                2685

Glu Arg Ser Thr Pro Leu Thr Asn Ile Leu Val Ser Thr Thr Leu
    2690                2695                2700

Leu Ala Asn Ser Glu Ala Ser Thr Leu Ser Thr Thr Pro Val Asp
    2705                2710                2715

Thr Ser Thr Pro Val Thr Thr Ser Ala Glu Ala Ser Ser Ser Pro
    2720                2725                2730
```

```
Thr Thr  Ala Glu Gly Thr Ser  Met Arg Ile Ser Thr  Pro Ser Asp
    2735                 2740                 2745

Gly Ser  Thr Pro Leu Thr Ser  Ile Leu Val Ser Thr  Leu Pro Val
    2750                 2755                 2760

Ala Ser  Ser Glu Ala Ser Thr  Val Ser Thr Thr Ala  Val Asp Thr
    2765                 2770                 2775

Ser Ile  Pro Val Thr Thr Ser  Thr Glu Ala Ser Ser  Ser Pro Thr
    2780                 2785                 2790

Thr Ala  Glu Val Thr Ser Met  Pro Thr Ser Thr Pro  Ser Glu Thr
    2795                 2800                 2805

Ser Thr  Pro Leu Thr Ser Met  Pro Val Asn His Thr  Pro Val Ala
    2810                 2815                 2820

Ser Ser  Glu Ala Gly Thr Leu  Ser Thr Thr Pro Val  Asp Thr Ser
    2825                 2830                 2835

Thr Pro  Val Thr Thr Ser Thr  Lys Ala Ser Ser Ser  Pro Thr Thr
    2840                 2845                 2850

Ala Glu  Gly Ile Val Val Pro  Ile Ser Thr Ala Ser  Glu Gly Ser
    2855                 2860                 2865

Thr Leu  Leu Thr Ser Ile Pro  Val Ser Thr Thr Pro  Val Ala Ser
    2870                 2875                 2880

Ser Glu  Ala Ser Thr Leu Ser  Thr Thr Pro Val Asp  Thr Ser Ile
    2885                 2890                 2895

Pro Val  Thr Thr Ser Thr Glu  Gly Ser Ser Ser Pro  Thr Thr Ala
    2900                 2905                 2910

Glu Gly  Thr Ser Met Pro Ile  Ser Thr Pro Ser Glu  Val Ser Thr
    2915                 2920                 2925

Pro Leu  Thr Ser Ile Leu Val  Ser Thr Val Pro Val  Ala Gly Ser
    2930                 2935                 2940

Glu Ala  Ser Thr Leu Ser Thr  Thr Pro Val Asp Thr  Arg Thr Pro
    2945                 2950                 2955

Val Thr  Thr Ser Ala Glu Ala  Ser Ser Ser Pro Thr  Thr Ala Glu
    2960                 2965                 2970

Gly Thr  Ser Met Pro Ile Ser  Thr Pro Gly Glu Arg  Arg Thr Pro
    2975                 2980                 2985

Leu Thr  Ser Met Ser Val Ser  Thr Met Pro Val Ala  Ser Ser Glu
    2990                 2995                 3000

Ala Ser  Thr Leu Ser Arg Thr  Pro Ala Asp Thr Ser  Thr Pro Val
    3005                 3010                 3015

Thr Thr  Ser Thr Glu Ala Ser  Ser Ser Pro Thr Thr  Ala Glu Gly
    3020                 3025                 3030

Thr Gly  Ile Pro Ile Ser Thr  Pro Ser Glu Gly Ser  Thr Pro Leu
    3035                 3040                 3045

Thr Ser  Ile Pro Val Ser Thr  Thr Pro Val Ala Ile  Pro Glu Ala
    3050                 3055                 3060

Ser Thr  Leu Ser Thr Thr Pro  Val Asp Ser Asn Ser  Pro Val Val
    3065                 3070                 3075

Thr Ser  Thr Glu Val Ser Ser  Ser Pro Thr Pro Ala  Glu Gly Thr
    3080                 3085                 3090

Ser Met  Pro Ile Ser Thr Tyr  Ser Glu Gly Ser Thr  Pro Leu Thr
    3095                 3100                 3105

Gly Val  Pro Val Ser Thr Thr  Pro Val Thr Ser Ser  Ala Ile Ser
    3110                 3115                 3120

Thr Leu  Ser Thr Thr Pro Val  Asp Thr Ser Thr Pro  Val Thr Thr
```

```
    3125                3130                3135

Ser Thr  Glu Ala His Ser Ser  Pro Thr Thr Ser Glu  Gly Thr Ser
    3140                3145                3150

Met Pro  Thr Ser Thr Pro Ser  Glu Gly Ser Thr Pro  Leu Thr Tyr
    3155                3160                3165

Met Pro  Val Ser Thr Met Leu  Val Val Ser Ser Glu  Asp Ser Thr
    3170                3175                3180

Leu Ser  Ala Thr Pro Val Asp  Thr Ser Thr Pro Val  Thr Thr Ser
    3185                3190                3195

Thr Glu  Ala Thr Ser Ser Thr  Thr Ala Glu Gly Thr  Ser Ile Pro
    3200                3205                3210

Thr Ser  Thr Pro Ser Glu Gly  Met Thr Pro Leu Thr  Ser Val Pro
    3215                3220                3225

Val Ser  Asn Thr Pro Val Ala  Ser Ser Glu Ala Ser  Ile Leu Ser
    3230                3235                3240

Thr Thr  Pro Val Asp Ser Asn  Thr Pro Leu Thr Thr  Ser Thr Glu
    3245                3250                3255

Ala Ser  Ser Ser Pro Pro Thr  Ala Glu Gly Thr Ser  Met Pro Thr
    3260                3265                3270

Ser Thr  Pro Ser Glu Gly Ser  Thr Pro Leu Thr Ser  Met Pro Val
    3275                3280                3285

Ser Thr  Thr Thr Val Ala Ser  Ser Glu Thr Ser Thr  Leu Ser Thr
    3290                3295                3300

Thr Pro  Ala Asp Thr Ser Thr  Pro Val Thr Thr Tyr  Ser Gln Ala
    3305                3310                3315

Ser Ser  Ser Pro Pro Ile Ala  Asp Gly Thr Ser Met  Pro Thr Ser
    3320                3325                3330

Thr Tyr  Ser Glu Gly Ser Thr  Pro Leu Thr Asn Met  Ser Phe Ser
    3335                3340                3345

Thr Thr  Pro Val Val Ser Ser  Glu Ala Ser Thr Leu  Ser Thr Thr
    3350                3355                3360

Pro Val  Asp Thr Ser Thr Pro  Val Thr Thr Ser Thr  Glu Ala Ser
    3365                3370                3375

Leu Ser  Pro Thr Thr Ala Glu  Gly Thr Ser Ile Pro  Thr Ser Ser
    3380                3385                3390

Pro Ser  Glu Gly Thr Thr Pro  Leu Ala Ser Met Pro  Val Ser Thr
    3395                3400                3405

Thr Pro  Val Val Ser Ser Glu  Val Asn Thr Leu Ser  Thr Thr Pro
    3410                3415                3420

Val Asp  Ser Asn Thr Leu Val  Thr Thr Ser Thr Glu  Ala Ser Ser
    3425                3430                3435

Ser Pro  Thr Ile Ala Glu Gly  Thr Ser Leu Pro Thr  Ser Thr Thr
    3440                3445                3450

Ser Glu  Gly Ser Thr Pro Leu  Ser Ile Met Pro Leu  Ser Thr Thr
    3455                3460                3465

Pro Val  Ala Ser Ser Glu Ala  Ser Thr Leu Ser Thr  Thr Pro Val
    3470                3475                3480

Asp Thr  Ser Thr Pro Val Thr  Thr Ser Ser Pro Thr  Asn Ser Ser
    3485                3490                3495

Pro Thr  Thr Ala Glu Val Thr  Ser Met Pro Thr Ser  Thr Ala Gly
    3500                3505                3510

Glu Gly  Ser Thr Pro Leu Thr  Asn Met Pro Val Ser  Thr Thr Pro
    3515                3520                3525
```

```
Val Ala Ser Ser Glu Ala Ser Thr Leu Ser Thr Thr Pro Val Asp
    3530                3535                3540

Ser Asn Thr Phe Val Thr Ser Ser Ser Gln Ala Ser Ser Ser Pro
    3545                3550                3555

Ala Thr Leu Gln Val Thr Thr Met Arg Met Ser Thr Pro Ser Glu
    3560                3565                3570

Gly Ser Ser Ser Leu Thr Thr Met Leu Leu Ser Ser Thr Tyr Val
    3575                3580                3585

Thr Ser Ser Glu Ala Ser Thr Pro Ser Thr Pro Ser Val Asp Arg
    3590                3595                3600

Ser Thr Pro Val Thr Thr Ser Thr Gln Ser Asn Ser Thr Pro Thr
    3605                3610                3615

Pro Pro Glu Val Ile Thr Leu Pro Met Ser Thr Pro Ser Glu Val
    3620                3625                3630

Ser Thr Pro Leu Thr Ile Met Pro Val Ser Thr Thr Ser Val Thr
    3635                3640                3645

Ile Ser Glu Ala Gly Thr Ala Ser Thr Leu Pro Val Asp Thr Ser
    3650                3655                3660

Thr Pro Val Ile Thr Ser Thr Gln Val Ser Ser Ser Pro Val Thr
    3665                3670                3675

Pro Glu Gly Thr Thr Met Pro Ile Trp Thr Pro Ser Glu Gly Ser
    3680                3685                3690

Thr Pro Leu Thr Thr Met Pro Val Ser Thr Thr Arg Val Thr Ser
    3695                3700                3705

Ser Glu Gly Ser Thr Leu Ser Thr Pro Ser Val Val Thr Ser Thr
    3710                3715                3720

Pro Val Thr Thr Ser Thr Glu Ala Ile Ser Ser Ser Ala Thr Leu
    3725                3730                3735

Asp Ser Thr Thr Met Ser Val Ser Met Pro Met Glu Ile Ser Thr
    3740                3745                3750

Leu Gly Thr Thr Ile Leu Val Ser Thr Thr Pro Val Thr Arg Phe
    3755                3760                3765

Pro Glu Ser Ser Thr Pro Ser Ile Pro Ser Val Tyr Thr Ser Met
    3770                3775                3780

Ser Met Thr Thr Ala Ser Glu Gly Ser Ser Ser Pro Thr Thr Leu
    3785                3790                3795

Glu Gly Thr Thr Thr Met Pro Met Ser Thr Thr Ser Glu Arg Ser
    3800                3805                3810

Thr Leu Leu Thr Thr Val Leu Ile Ser Pro Ile Ser Val Met Ser
    3815                3820                3825

Pro Ser Glu Ala Ser Thr Leu Ser Thr Pro Pro Gly Asp Thr Ser
    3830                3835                3840

Thr Pro Leu Leu Thr Ser Thr Lys Ala Gly Ser Phe Ser Ile Pro
    3845                3850                3855

Ala Glu Val Thr Thr Ile Arg Ile Ser Ile Thr Ser Glu Arg Ser
    3860                3865                3870

Thr Pro Leu Thr Thr Leu Leu Val Ser Thr Thr Leu Pro Thr Ser
    3875                3880                3885

Phe Pro Gly Ala Ser Ile Ala Ser Thr Pro Pro Leu Asp Thr Ser
    3890                3895                3900

Thr Thr Phe Thr Pro Ser Thr Asp Thr Ala Ser Thr Pro Thr Ile
    3905                3910                3915
```

```
Pro Val  Ala Thr Thr Ile Ser  Val Ser Val Ile Thr  Glu Gly Ser
    3920                3925                3930

Thr Pro  Gly Thr Thr Ile Phe  Ile Pro Ser Thr Pro  Val Thr Ser
    3935                3940                3945

Ser Thr  Ala Asp Val Phe Pro  Ala Thr Thr Gly Ala  Val Ser Thr
    3950                3955                3960

Pro Val  Ile Thr Ser Thr Glu  Leu Asn Thr Pro Ser  Thr Ser Ser
    3965                3970                3975

Ser Ser  Thr Thr Thr Ser Phe  Ser Thr Thr Lys Glu  Phe Thr Thr
    3980                3985                3990

Pro Ala  Met Thr Thr Ala Ala  Pro Leu Thr Tyr Val  Thr Met Ser
    3995                4000                4005

Thr Ala  Pro Ser Thr Pro Arg  Thr Thr Ser Arg Gly  Cys Thr Thr
    4010                4015                4020

Ser Ala  Ser Thr Leu Ser Ala  Thr Ser Thr Pro His  Thr Ser Thr
    4025                4030                4035

Ser Val  Thr Thr Arg Pro Val  Thr Pro Ser Ser Glu  Ser Ser Arg
    4040                4045                4050

Pro Ser  Thr Ile Thr Ser His  Thr Ile Pro Pro Thr  Phe Pro Pro
    4055                4060                4065

Ala His  Ser Ser Thr Pro Pro  Thr Thr Ser Ala Ser  Ser Thr Thr
    4070                4075                4080

Val Asn  Pro Glu Ala Val Thr  Thr Met Thr Thr Arg  Thr Lys Pro
    4085                4090                4095

Ser Thr  Arg Thr Thr Ser Phe  Pro Thr Val Thr Thr  Thr Ala Val
    4100                4105                4110

Pro Thr  Asn Thr Thr Ile Lys  Ser Asn Pro Thr Ser  Thr Pro Thr
    4115                4120                4125

Val Pro  Arg Thr Thr Thr Cys  Phe Gly Asp Gly Cys  Gln Asn Thr
    4130                4135                4140

Ala Ser  Arg Cys Lys Asn Gly  Gly Thr Trp Asp Gly  Leu Lys Cys
    4145                4150                4155

Gln Cys  Pro Asn Leu Tyr Tyr  Gly Glu Leu Cys Glu  Glu Val Val
    4160                4165                4170

Ser Ser  Ile Asp Ile Gly Pro  Pro Glu Thr Ile Ser  Ala Gln Met
    4175                4180                4185

Glu Leu  Thr Val Thr Val Thr  Ser Val Lys Phe Thr  Glu Glu Leu
    4190                4195                4200

Lys Asn  His Ser Ser Gln Glu  Phe Gln Glu Phe Lys  Gln Thr Phe
    4205                4210                4215

Thr Glu  Gln Met Asn Ile Val  Tyr Ser Gly Ile Pro  Glu Tyr Val
    4220                4225                4230

Gly Val  Asn Ile Thr Lys Leu  Arg Leu Gly Ser Val  Val Val Glu
    4235                4240                4245

His Asp  Val Leu Leu Arg Thr  Lys Tyr Thr Pro Glu  Tyr Lys Thr
    4250                4255                4260

Val Leu  Asp Asn Ala Thr Glu  Val Val Lys Glu Lys  Ile Thr Lys
    4265                4270                4275

Val Thr  Thr Gln Gln Ile Met  Ile Asn Asp Ile Cys  Ser Asp Met
    4280                4285                4290

Met Cys  Phe Asn Thr Thr Gly  Thr Gln Val Gln Asn  Ile Thr Val
    4295                4300                4305

Thr Gln  Tyr Asp Pro Glu Glu  Asp Cys Arg Lys Met  Ala Lys Glu
```

```
    4310                4315                4320

Tyr Gly  Asp Tyr Phe Val Val  Glu Tyr Arg Asp Gln  Lys Pro Tyr
    4325                4330                4335

Cys Ile  Ser Pro Cys Glu Pro  Gly Phe Ser Val Ser  Lys Asn Cys
    4340                4345                4350

Asn Leu  Gly Lys Cys Gln Met  Ser Leu Ser Gly Pro  Gln Cys Leu
    4355                4360                4365

Cys Val  Thr Thr Glu Thr His  Trp Tyr Ser Gly Glu  Thr Cys Asn
    4370                4375                4380

Gln Gly  Thr Gln Lys Ser Leu  Val Tyr Gly Leu Val  Gly Ala Gly
    4385                4390                4395

Val Val  Leu Met Leu Ile Ile  Leu Val Ala Leu Leu  Met Leu Val
    4400                4405                4410

Phe Arg  Ser Lys Arg Glu Val  Lys Arg Gln Lys Tyr  Arg Leu Ser
    4415                4420                4425

Gln Leu  Tyr Lys Trp Gln Glu  Glu Asp Ser Gly Pro  Ala Pro Gly
    4430                4435                4440

Thr Phe  Gln Asn Ile Gly Phe  Asp Ile Cys Gln Asp  Asp Asp Ser
    4445                4450                4455

Ile His  Leu Glu Ser Ile Tyr  Ser Asn Phe Gln Pro  Ser Leu Arg
    4460                4465                4470

His Ile  Asp Pro Glu Thr Lys  Ile Arg Ile Gln Arg  Pro Gln Val
    4475                4480                4485

Met Thr  Thr Ser Phe
    4490


<210> SEQ ID NO 11
<211> LENGTH: 167
<212> TYPE: PRT
<213> ORGANISM: Human

<400> SEQUENCE: 11

Met Leu Thr Val Ala Leu Leu Ala Leu Leu Cys Ala Ser Ala Ser Gly
1               5                   10                  15

Asn Ala Ile Gln Ala Arg Ser Ser Ser Tyr Ser Gly Glu Tyr Gly Ser
            20                  25                  30

Gly Gly Gly Lys Arg Phe Ser His Ser Gly Asn Gln Leu Asp Gly Pro
        35                  40                  45

Ile Thr Ala Leu Arg Val Arg Val Asn Thr Tyr Tyr Ile Val Gly Leu
    50                  55                  60

Gln Val Arg Tyr Gly Lys Val Trp Ser Asp Tyr Val Gly Gly Arg Asn
65                  70                  75                  80

Gly Asp Leu Glu Glu Ile Phe Leu His Pro Gly Glu Ser Val Ile Gln
                85                  90                  95

Val Ser Gly Lys Tyr Lys Trp Tyr Leu Lys Lys Leu Val Phe Val Thr
            100                 105                 110

Asp Lys Gly Arg Tyr Leu Ser Phe Gly Lys Asp Ser Gly Thr Ser Phe
        115                 120                 125

Asn Ala Val Pro Leu His Pro Asn Thr Val Leu Arg Phe Ile Ser Gly
    130                 135                 140

Arg Ser Gly Ser Leu Ile Asp Ala Ile Gly Leu His Trp Asp Val Tyr
145                 150                 155                 160

Pro Thr Ser Cys Ser Arg Cys
                165
```

MARKERS FOR DETECTION OF GASTRIC CANCER

CLAIM OF PRIORITY

This application is a United States National Phase Application filed under 35 U.S.C. §371 claiming priority to International Application No. PCT/NZ2010/000089, filed 14 May 2010, which claims priority to New Zealand Provisional Application No. 577,012, filed 15 May 2009. Each of these applications is herein fully incorporated by reference, as if separately so incorporated.

FIELD OF THE INVENTION

This invention relates to detection of cancer. Specifically, this invention relates to the use of genetic and/or protein markers for detection of cancer, and more particularly to the use of genetic and/or protein markers for detection of gastric cancer.

BACKGROUND

Survival of cancer patients is greatly enhanced when the cancer is detected and treated early. In the case of gastric cancer, patients diagnosed with early stage disease have 5-year survival rates of 90%, compared to approximately 10% for patients diagnosed with advanced disease. However, the vast majority of gastric cancer patients currently present with advanced disease. Therefore, developments that lead to early diagnosis of gastric cancer can lead to an improved prognosis for the patients.

Identification of specific cancer-associated markers in biological samples, including body fluids, for example, blood, urine, peritoneal washes and stool extracts can provide a valuable approach for the early diagnosis of cancer, leading to early treatment and improved prognosis. Specific cancer markers also can provide a means for monitoring disease progression, enabling the efficacy of surgical, radiotherapeutic and chemotherapeutic treatments to be tracked. However, for a number of major cancers, the available markers suffer from insufficient sensitivity and specificity. For example, the most frequently used markers for gastric cancer, ca19-9, ca72-4 and carcino-embryonic antigen (CEA) detect only about 15-50% of gastric tumors of any stage, declining to approximately 2-11% for early stage disease. Thus, there is a very high frequency of false negative tests that can lead patients and health care practitioners to believe that no disease exists, whereas in fact, the patient may have severe cancer that needs immediate attention. Moreover, these markers can give false positive signals in up to ⅓ of individuals affected by benign gastric disease.

SUMMARY OF THE INVENTION

Aspects of this invention provide methods, compositions and devices that can provide for detection of early stage cancer, and decrease the frequency of false positives and false negative test results.

In certain embodiments, molecular analyses can be used to identify genes that are highly expressed in gastric tumor tissue, but not necessarily over-expressed compared to non-malignant gastric tissue. Such analyses include microarray and quantitative polymerase chain reaction (qPCR) methods. Cancer genes, RNAs and proteins encoded by those genes are herein termed gastric tumor markers (GTM). It is to be understood that the term GTM does not require that the marker be specific only for gastric tumors. Rather, expression of GTM can be increased in other types of tumors, including malignant or non-malignant tumors, including gastric, bladder, colorectal, pancreatic, ovarian, skin (e.g., melanomas), liver, esophageal, endometrial and brain cancers, among others. It should be understood, however that the term GTM does not include the prior art markers, such as CA19-9, CA72-4, pepsinogen and CEA, or any other markers that have been previously identified as being indicative of gastric tumors. Some GTM are secreted or escape from tumors at sufficient levels to be diagnostic of gastric cancer with a high degree of reliability, and in other cases, measurement of two or more GTM can provide reliable diagnosis of gastric cancer.

Proteins that are secreted by or cleaved from the cell, either alone or in combination with each other, have utility as serum or body fluid markers for the diagnosis of gastric cancer or as markers for monitoring the progression of established disease. Detection of protein markers can be carried out using methods known in the art, and include the use of monoclonal antibodies, polyclonal antisera and the like.

Specifically the present invention provides for a method for detecting gastric cancer, comprising:

(i) providing a biological sample; and (ii) detecting the levels of human zymogen granule protein 16 ("ZG16") in said sample.

In one aspect, and over expression of ZG16 in a patient is indicative of the patient having gastric cancer.

The further GTM family member according to the present invention may be selected from the group consisting of mucin 5AC ("MUC5AC"), or mucin 17 ("MUC17"). The method may involve the detection of ZG16 and MUC5AC, ZG16 and MUC17, or Z316 and MUC5AC and MUC17.

The further GTM family member may also comprise one or more further GTM family member, for example anyone of MUC5AC, MUC17, ZG16, carboxypeptidase N, polypeptide 2, 83 kDa chain (CPN2), matrix metalloproteinase 12 (MMP12), inhibin ("INHBA"), insulin-like growth factor 7 ("IGFBP7"), gamma-glutamyl hydrolase ("GGH"), leucine proline enriched proteoglycan ("LEPRE1"), cystatin S ("CST4"), secreted frizzled-related protein 4 ("SFRP4"), asporin ("ASPN"), cell growth regulator with EF hand domain 1 ("CGREF1"), kallikrein 10 (KLK10), tissue inhibitor of metalloproteinase 1 ("TIMP1"), secreted acidic cysteine-rich protein ("SPARC"), transforming growth factor, 13-induced ("TGFBI"), EGF-containing fibulin-like extracellular matrix protein 2 ("EFEMP2"), lumican ("LUM"), stannin ("SNN"), secreted phosphoprotein 1 ("SPP1"), chondroitin sulfate proteoglycan 2 ("CSPG2"), N-acylsphingosine amidohydrolase ("ASAH1"), serine protease 11 ("PRSS11"), secreted frizzled-related protein 2 ("SFRP2"), phospholipase A2, group XIIB ("PLA2G12B"), spondin 2, extracellular matrix protein ("SPON2"), olfactomedin 1 ("OLFM1"), thrombospondin repeat containing 1 ("TSRC1"), thrombospondin 2 ("THBS2"), adlican, cystatin SA ("CST2"), cystatin SN ("CST1"), lysyl oxidase-like enzyme 2 ("LOXL2"), thyroglobulin ("TG"), transforming growth factor beta1 ("TGFB1"), serine or cysteine proteinase inhibitor Clade H, member 1 ("SERPINH1"), serine or cysteine proteinase inhibitor Clade B, member 5 ("SERPINB5"), matrix metalloproteinase 2 ("MMP2"), proprotein convertase subtilisin/kexin type 5 ("PCSK5"), hyaluronan glycoprotein link protein 4 ("HAPLN4"), CA19-9, CA72-4, pepsinogen, CEA, MUC5AC and MUC17.

One example of a combination GTM markers according to the present invention is MUC5AC, MUC17, ZG16, cystatin SN, serpinH1 and serpinB5

Any suitable method for detecting the level of the GTM can be used, and may include detecting the levels of a GTM mRNA, GTM cDNA, using an oligonucleotide complementary to at least a portion of said GTM cDNA, using qRT-PCR method using a forward primer and a reverse primer, detecting the levels of a GTM protein, detecting the levels of a GTM peptide, for example using an antibody directed against said GTM. Any suitable antibody can be used, and may be a monoclonal antibody or a polyclonal antiserum. The method may be carried out using a sandwich-type immunoassay method, or using an antibody chip.

The present invention also provides for a device for detecting a GTM, comprising: a substrate having a GTM capture reagent thereon; and a detector associated with said substrate, said detector capable of detecting a GTM associated with said capture reagent.

The GTM capture reagent may be an oligonucleotide or an antibody specific for either a GTM oligonucleotide, a GTM protein or a GTM peptide.

A further aspect of the present invention is a kit for detecting cancer, comprising:

a substrate having a GTM capture reagent thereon;

a means for visualizing a complex of said GTM capture agent and a GTM; reagents; and instructions for use, wherein said GTM comprises human zymogen granule protein 16 ("ZG16").

The GTM capture reagent is a GTM-specific oligonucleotide or a GTM-specific antibody selective for a GTM oligonucleotide, a GTM protein or a GTM peptide.

The present invention also provides for a method for detecting gastric cancer, comprising the steps of:

providing a test sample from a patient at risk of having gastric cancer; measuring the presence of a GTM protein in said test sample; and comparing the amount of GTM present in said test sample with a value obtained from a control sample from a subject not having gastric cancer, wherein said GTM comprises human zymogen granule protein 16 ("ZG16").

In a yet further aspect the invention provides for a method for screening for gastric cancer, comprising the steps of: providing a test sample from a test subject;

measuring the presence of a GTM in said test sample; and comparing the amount of GTM present in said test sample with a value obtained from a control sample from a subject not having gastric cancer, wherein said GTM comprises human zymogen granule protein 16 ("ZG16").

The GTM may be a GTM protein or peptide, or an oligonucleotide specific for a GTM. The oligonucleotide may be DNA or RNA.

According the method, the step of measuring may use an ELISA assay.

The test sample may be obtained from plasma, tissue, urine, gastric fluid, serum and stool.

BRIEF DESCRIPTION OF THE FIGURES

This invention is described with reference to specific embodiments thereof and with reference to the figures, in which:

FIG. 1 depicts a table of microarray analysis showing genes with high relative expression in tumor tissue. Signal intensity for each gene in both tumor tissue and non-malignant tissue was ranked. The table shows GTMs with a higher ranking than the existing gastric cancer marker CEA (encoded by the gene CEACAM5).

FIG. 2 depicts a table showing the characteristics of serum samples used in antibody array analysis.

DETAILED DESCRIPTION

Definitions

Figure 3:
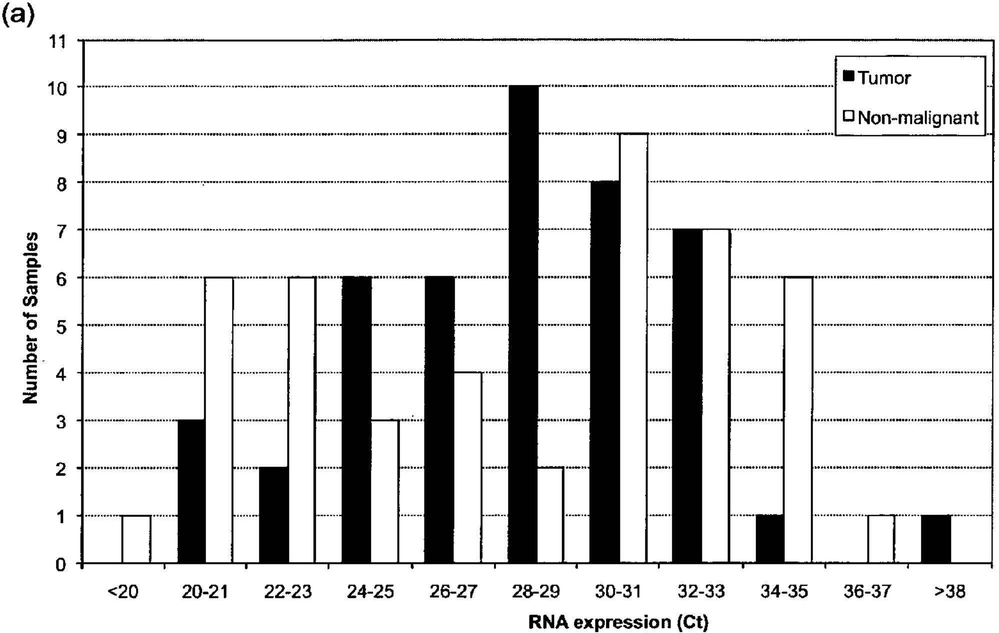
FIG. 3 depicts histograms showing the distribution of tumor and nonmalignant samples according to their level of expression of (a) ZG16 and (b) MUC17. The level of expression of the two genes was obtained using RT-qPCR.
Figure 3:
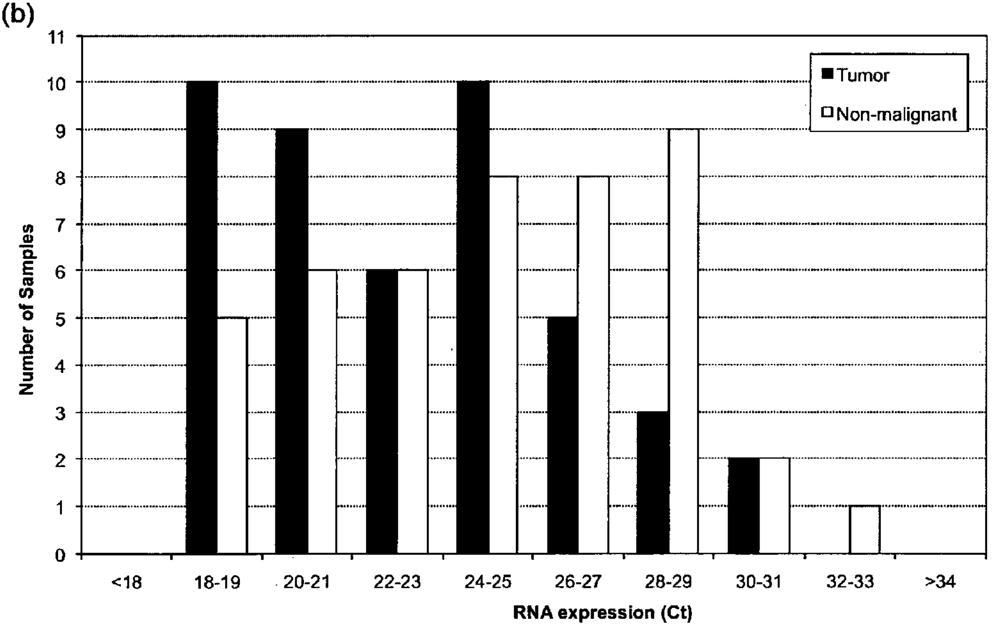
Figure 4:
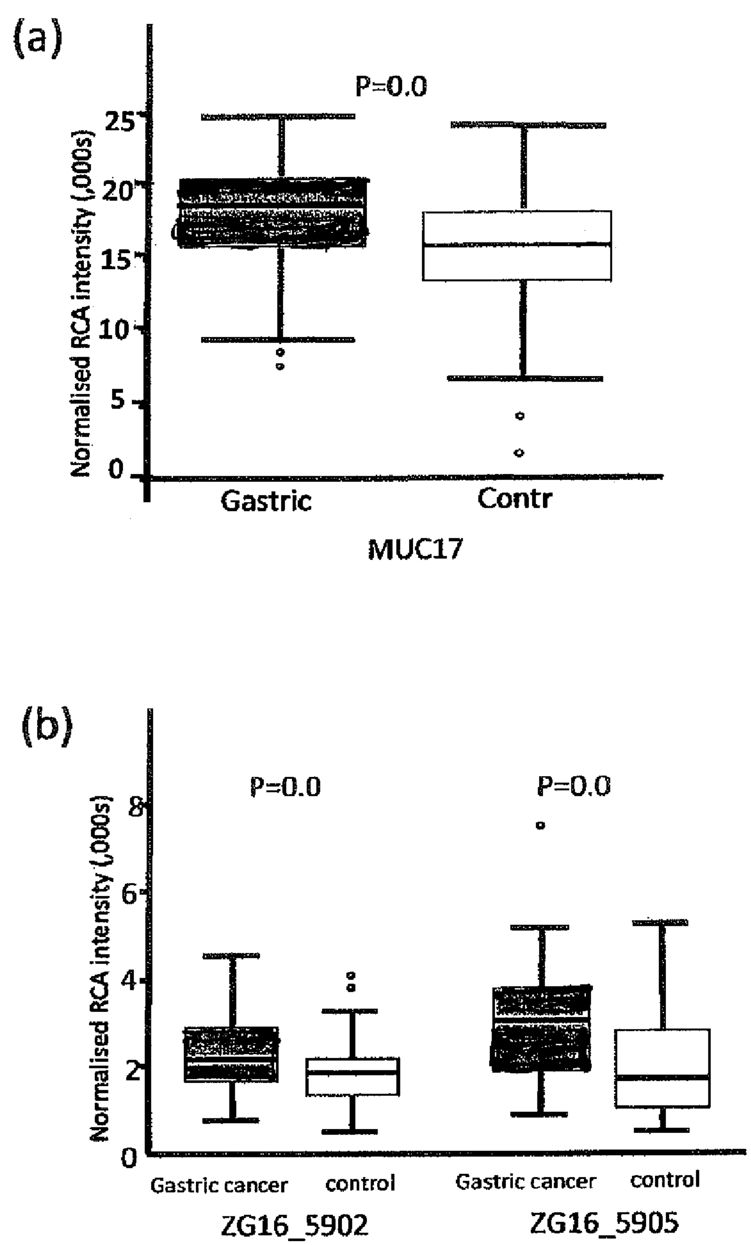
FIG. 4 depicts boxplots showing the detection of (a) MUC17 and (b) ZG16 in the serum of gastric cancer patients and controls using antibody arrays and RCA detection.

Before describing embodiments of the invention in detail, it will be useful to provide some definitions of terms as used herein.

The term "GTM" or "gastric tumor marker" or "GTM family member" means a gene, gene fragment, RNA, RNA fragment, protein or protein fragment related or other identifying molecule associated with gastric cancer. The GTMs disclosed as part of the present invention do not include molecules that are known in the prior art to be associated with gastric cancer, e.g. CA19-9, CA72-4, pepsinogen and CEA. However, the markers of the present invention can be used in novel and inventive combinations with previously disclosed GTMs.

The term "marker" refers to a molecule that is associated quantitatively or qualitatively with the presence of a biological phenomenon. Examples of "markers" include a polynucleotide, such as a gene or gene fragment, RNA or RNA fragment; or a gene product, including a polypeptide such as a peptide, oligopeptide, protein, or protein fragment; or any related metabolites, by products, or any other identifying molecules, such as antibodies or antibody fragments, whether related directly or indirectly to a mechanism underlying the phenomenon. The markers of the invention include the nucleotide sequences (e.g., GenBank sequences) as disclosed herein, in particular, the full-length sequences, any coding sequences, any fragments, or any complements thereof, and any measurable marker thereof as defined above.

As used herein "antibodies" and like terms refer to immunoglobulin molecules and immunologically active portions of immunoglobulin (Ig) molecules, i.e., molecules that contain an antigen binding site that specifically binds (immunoreacts with) an antigen. These include, but are not limited to, polyclonal, monoclonal, chimeric, single chain, Fc, Fab, Fab', and $Fab_2$ fragments, and a Fab expression library. Antibody molecules relate to any of the classes IgG, IgM, IgA, IgE, and IgD, which differ from one another by the nature of heavy chain present in the molecule. These include subclasses as well, such as IgGI, IgG2, and others. The light chain may be a kappa chain or a lambda chain. Reference herein to antibodies includes a reference to all classes, subclasses, and types. Also included are chimeric antibodies, for example, monoclonal antibodies or fragments thereof that are specific to more than one source, e.g., a mouse or human sequence. Further included are camelid antibodies, shark antibodies or nanobodies.

The terms "cancer" and "cancerous" refer to or describe the physiological condition in mammals that is typically characterized by abnormal or unregulated cell growth. Cancer and cancer pathology can be associated, for example, with metastasis, interference with the normal functioning of neighbouring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc. Specifically included are melanomas.

The term "tumour" refers to all neoplastic cell growth and proliferation, whether malignant or benign, and all pre-cancerous and cancerous cells and tissues.

The term "gastric cancer" refers to a tumor originating in the stomach. These tumors are able to metastasize to any organ.

The terms "differentially expressed," "differential expression," and like phrases, refer to a gene marker whose expression is activated to a higher or lower level in a subject (e.g., test sample) having a condition, specifically cancer, such as melanoma, relative to its expression in a control subject (e.g., reference sample). The terms also include markers whose expression is activated to a higher or lower level at different stages of the same condition; in diseases with a good or poor prognosis; or in cells with higher or lower levels of proliferation. A differentially expressed marker may be either activated or inhibited at the polynucleotide level or polypeptide level, or may be subject to alternative splicing to result in a different polypeptide product. Such differences may be evidenced by a change in mRNA levels, surface expression, secretion or other partitioning of a polypeptide, for example.

Differential expression may include a comparison of expression between two or more markers (e.g., genes or their gene products); or a comparison of the ratios of the expression between two or more markers (e.g., genes or their gene products); or a comparison of two differently processed products (e.g., transcripts or polypeptides) of the same marker, which differ between normal subjects and diseased subjects; or between various stages of the same disease; or between diseases having a good or poor prognosis; or between cells with higher and lower levels of proliferation; or between normal tissue and diseased tissue, specifically cancer, or melanoma. Differential expression includes both quantitative, as well as qualitative, differences in the temporal or cellular expression pattern in a gene or its expression products among, for example, normal and diseased cells, or among cells which have undergone different disease events or disease stages, or cells with different levels of proliferation.

The term "expression" includes production of polynucleotides and polypeptides, in particular, the production of RNA (e.g., mRNA) from a gene or portion of a gene, and includes the production of a polypeptide encoded by an RNA or gene or portion of a gene, and the appearance of a detectable material associated with expression. For example, the formation of a complex, for example, from a polypeptide-polypeptide interaction, polypeptide-nucleotide interaction, or the like, is included within the scope of the term "expression". Another example is the binding of a binding ligand, such as a hybridization probe or antibody, to a gene or other polynucleotide or oligonucleotide, a polypeptide or a protein fragment, and the visualization of the binding ligand. Thus, the intensity of a spot on a microarray, on a hybridization blot such as a Northern blot, or on an immunoblot such as a Western blot, or on a bead array, or by PCR analysis, is included within the term "expression" of the underlying biological molecule.

The terms "expression threshold," and "defined expression threshold" are used interchangeably and refer to the level of a marker in question outside which the polynucleotide or polypeptide serves as a predictive marker for patient survival. The threshold will be dependent on the predictive model established are derived experimentally from clinical studies such as those described in the Examples below. Depending on the prediction model used, the expression threshold may be set to achieve maximum sensitivity, or for maximum specificity; or for minimum error (maximum classification rate). For example a higher threshold may be set to achieve minimum errors, but this may result in a lower sensitivity. Therefore, for any given predictive model, clinical studies will be used to set an expression threshold that generally achieves the highest sensitivity while having a minimal error rate. The determination of the expression threshold for any situation is well within the knowledge of those skilled in the art.

The term "sensitivity" means the proportion of individuals with the disease who test (by the model) positive. Thus, increased sensitivity means fewer false negative test results.

The term "specificity" means the proportion of individuals without the disease who test (by the model) negative. Thus, increased specificity means fewer false positive test results.

The term "microarray" refers to an ordered or unordered arrangement of capture agents, preferably polynucleotides (e.g., probes) or polypeptides on a substrate. See, e.g., Microarray Analysis, M. Schena, John Wiley & Sons, 2002; Microarray Biochip Technology, M. Schena, ed., Eaton Publishing, 2000; Guide to Analysis of DNA Microarray. Data, S. Knudsen, John Wiley & Sons, 2004; and Protein Microarray Technology, D. Kambhampati, ed., John Wiley & Sons, 2004.

The term "oligonucleotide" refers to a polynucleotide, typically a probe or primer, including, without limitation, single-stranded deoxyribonucleotides, single- or double-stranded ribonucleotides, RNA: DNA hybrids, and double-stranded DNAs. Oligonucleotides, such as single-stranded DNA probe oligonucleotides, are often synthesized by chemical methods, for example using automated oligonucleotide synthesizers that are commercially available, or by a variety of other methods, including in vitro expression systems, recombinant techniques, and expression in cells and organisms.

The term "overexpression" or "overexpressed" refers to an expression level of a gene or marker in a patient that is above that seen in normal tissue. Expression may be considered to be overexpressed if it is 1.2, 1.3, 1.4, 1.5, 1.6, 1.7, 1.8, 1.9, 2, or greater then 2 times the expression in normal tissue.

The term "polynucleotide," when used in the singular or plural, generally refers to any polyribonucleotide or polydeoxribonucleotide, which may be unmodified RNA or DNA or modified RNA or DNA. This includes, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. Also included are triple-stranded regions comprising RNA or DNA or both RNA and DNA. Specifically included are mRNAs, cDNAs, and genomic DNAs, and any fragments thereof. The term includes DNAs and RNAs that contain one or more modified bases, such as tritiated bases, or unusual bases, such as inosine. The polynucleotides of the invention can encompass coding or non-coding sequences, or sense or antisense sequences. It will be understood that each reference to a "polynucleotide" or like term, herein, will include the full-length sequences as well as any fragments, derivatives, or variants thereof.

"Polypeptide," as used herein, refers to an oligopeptide, peptide, or protein sequence, or fragment thereof, and to naturally occurring, recombinant, synthetic, or semi-synthetic molecules. Where "polypeptide" is recited herein to refer to an amino acid sequence of a naturally occurring protein molecule, "polypeptide" and like terms, are not meant to limit the amino acid sequence to the complete, native amino acid sequence for the full-length molecule. It will be understood that each reference to a "polypeptide" or like term, herein, will include the full-length sequence, as well as any fragments, derivatives, or variants thereof.

The term "qPCR" or "QPCR" refers to quantitative polymerase chain reaction as described, for example, in PCR Technique: Quantitative PCR, J. W. Larrick, ed., Eaton Publishing, 1997, and A-Z of Quantitative PCR, S. Bustin, ed., IUL Press, 2004.

The term RCA is an abbreviation for rolling circle amplification. RCA is a technique which involves the repeated copying of a circular template to amplify a signal, in a linear manner.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridisable sequence, the higher the relative temperature which can be used. As a result, it follows that higher relative temperatures would tend to make the reaction conditions more stringent, while lower temperatures less so. Additional details and explanation of stringency of hybridization reactions, are found e.g., in Ausubel et al., Current Protocols in Molecular Biology, Wiley Interscience Publishers, (1995).

"Stringent conditions" or "high stringency conditions", as defined herein, typically: (1) employ low ionic strength and high temperature for washing, for example 0.015 M sodium chloride/0.0015 M sodium citrate/0.1% sodium dodecyl sulfate at 50° C.; (2) employ a denaturing agent during hybridization, such as formamide, for example, 50% (v/v) formamide with 0.1% bovine serum albumin/0.1% Fico11/0.1% polyvinylpyrrolidone/50 mM sodium phosphate, buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×, Denhardt's solution, sonicated salmon sperm DNA (50 ug/ml), 0.1% SDS, and 10% dextran sulfate at 42° C., with washes at 42° C. in 0.2×SSC (sodium chloride/sodium citrate) and 50% formamide at 55° C., followed by a high-stringency wash comprising 0.1×SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength, and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "MUC5AC" means mucin 5AC (Seq ID Nos 1 and 4), and includes the marker MUC5AC, including a polynucleotide, such as a gene or gene fragment, RNA or RNA fragment; or a gene product, including a polypeptide such as a peptide, oligopeptide, protein, or protein fragment; or any related metabolites, by products, or any other identifying molecules, such as antibodies or antibody fragments The term "MUC17" means human mucin 17, cell surface associated (Seq ID Nos 2 and 5), and includes the marker MUC17, including a polynucleotide, such as a gene or gene fragment, RNA or RNA fragment; or a gene product, including a polypeptide such as a peptide, oligopeptide, protein, or protein fragment; or any related metabolites, by products, or any other identifying molecules, such as antibodies or antibody fragments.

The term "ZG16" means human zymogen granule protein 16 (Seq ID Nos 3 and 6), and includes the marker ZG16, including a polynucleotide, such as a gene or gene fragment, RNA or RNA fragment; or a gene product, including a polypeptide such as a peptide, oligopeptide, protein, or protein fragment; or any related metabolites, by products, or any other identifying molecules, such as antibodies or antibody fragments.

The practice of the present invention will employ, unless otherwise indicated, conventional techniques of molecular biology (including recombinant techniques), microbiology, cell biology, and biochemistry, which are within the skill of the art. Such techniques are explained fully in the literature, such as, Molecular Cloning: A Laboratory Manual, 2nd edition, Sambrook et al., 1989; Oligonucleotide Synthesis, M J Gait, ed., 1984; Animal Cell Culture, R. I. Freshney, ed., 1987; Methods in Enzymology, Academic Press, Inc.; Handbook of Experimental Immunology, 4th edition, D. M. Weir & CC. Blackwell, eds., Blackwell Science Inc., 1987; Gene Transfer Vectors for Mammalian Cells, J. M. Miller & M. P. Cabs, eds., 1987; Current Protocols in Molecular Biology, P. M. Ausubel et al., eds., 1987; and PCR: The Polymerase Chain Reaction, Mullis et al., eds., 1994.

It is to be understood that the above terms may refer to protein, DNA sequence and/or RNA sequence. It is also to be understood that the above terms also refer to non-human proteins, DNA and/or RNA having homologous sequences as depicted herein.

DESCRIPTION OF EMBODIMENTS OF THE INVENTION

Typically, tumor markers are differentially expressed between tumor tissue and corresponding non-malignant tissue. This provides a means to distinguish between patients with and without cancer. However, it is probable that the anatomical structure and physiological characteristics of tumor tissues will lead to differences in the accumulation of markers in serum and other biological fluids even when those markers aren't over-expressed in tumor tissue. In particular, the abnormal polarity of tumor cells, the leaky vasculature and the high interstitial pressure of tumor tissue would be predicted to favour the efflux of specific markers out of tumor tissue compared to non-malignant tissue. Consequently, it is hypothesized that secreted proteins that are expressed at very high levels in gastric tumour tissue, but not necessarily over-expressed compared to non-malignant gastric tissue, would constitute useful gastric cancer markers.

Using a combination of microarray analysis and quantitative polymerase chain reaction (qPCR), novel markers for the detection of gastric cancer have been identified. This novel gastric tumor marker (GTM), provide further tools in the early detection of gastric cancer. Specifically, the invention comprises the novel GTMs: MUC5AC (Seq ID Nos 1 and 4), MUC17 (Seq ID Nos 2 and 5), and ZG16 (Seq ID Nos 3 and 6).

The novel GTMs can be used in isolation, or alternatively they can be combined together as signature (comprising two or more GTMs). A signature according to the present invention includes at least one of MUC5AC, MUG 17, and ZG16, and at least one further GTM, which can either be a GTM according to the present invention, or any other GTM, including known GTMs.

Known GTMs suitable for use in combination with the presently disclosed GTMs include carboxypeptidase N, polypeptide 2, 83 kDa chain (CPN2), matrix metalloproteinase 12 (MMP12), inhibin ("INHBA"), insulin-like growth factor 7 ("IGFBP7"), gamma-glutamyl hydrolase ("GGH"), leucine proline-enriched proteoglycan ("LEPREI"), cystatin S ("CST4"), secreted frizzled-related protein 4 ("SFRP4"), asporin ("ASPN"), cell growth regulator with EF hand domain 1 ("CGREF1"), kallikrein 10 (KLK10), tissue inhibitor of metalloproteinase 1 ("TIMP1"), secreted acidic cysteine-rich protein ("SPARC"), transforming growth factor, 13-induced ("TGFBI"), EGF-containing fibulin-like extracellular matrix protein 2 ("EFEMP2"), lumican ("LUM"), stannin ("SNN"), secreted phosphoprotein 1 ("SPP1"), chondroitin sulfate proteoglycan 2 ("CSPG2"), N-acylsphingosine amidohydrolase ("ASAH1"), serine protease 11 ("PRSS11"), secreted frizzled-related protein 2 ("SFRP2"), phospholipase A2, group XIIB ("PLA2G12B"), spondin 2, extracellular matrix protein ("SPON2"), olfactomedin 1 ("OLFM1"), thrombospondin repeat containing 1 ("TSRC1"), thrombospondin 2 ("THBS2"), adlican, cystatin SA ("CST2"), cystatin SN ("CSTI"), lysyl oxidase-like enzyme 2 ("LOXL2"), thyroglobulin ("TG"), transforming growth factor beta 1 ("TGFB1"), serine or cysteine proteinase inhibitor Clade H, member 1 ("SERPINH1"), serine or cysteine proteinase inhibitor Clade B, member 5 ("SERPINB5"), matrix metalloproteinase 2 ("MMP2"), proprotein convertase subtilisin/kexin type 5 ("PCSK5"), hyaluronan glycoprotein link protein 4 ("HAPLN4"), CA19-9, CA72-4, pepsinogen and CEA, or any other markers that have been previously identified as being indicative of gastric tumors.

By the term "reliability" we include the low incidence of false positives and/or false negatives. Thus, with higher reliability of a marker, fewer false positives and/or false negatives are associated with diagnoses made using that marker. Therefore, in certain embodiments, markers are provided that permit detection of gastric cancer with reliability greater than the reliability of prior art markers of about 50%. In other embodiments, markers are provided that have reliability greater than about 70%; in other embodiments, greater than about 73%, in still other embodiments, greater than about 80%, in yet further embodiments, greater than about 90%, in still others, greater than about 95%, in yet further embodiments greater than about 98%, and in certain embodiments, about 100% reliability.

General Approaches to Cancer Detection

General methodologies for determining expression levels are outlined below, although it will be appreciated that any method for determining expression levels would be suitable.

Quantitative PCR (VCR)

Quantitative PCR (qPCR) can be carried out on tumour samples, on serum and plasma using GTM specific primers and probes. In controlled reactions, the amount of product formed in a PCR reaction (Sambrook, J., E Fritsch, E. and T Maniatis, Molecular Cloning: A Laboratory Manual 3$^{rd}$. Cold Spring Harbor Laboratory Press: Cold Spring Harbor (2001)) correlates with the amount of starting template. Quantification of the PCR product can be carried out by stopping the PCR reaction when it is in log phase, before reagents become limiting. The PCR products are then electrophoresed in agarose or polyacrylamide gels, stained with ethidium bromide or a comparable DNA stain, and the intensity of staining measured by densitometry. Alternatively, the progression of a PCR reaction can be measured using PCR machines such as the Applied Biosystems' Prism 7000 or the Roche LightCycler which measure product accumulation in real-time. Real-time PCR measures either the fluorescence of DNA intercalating dyes such as Sybr Green into the synthesized PCR product, or the fluorescence released by a reporter molecule when cleaved from a quencher molecule; the reporter and quencher molecules are incorporated into an oligonucleotide probe which hybridizes to the target DNA molecule following DNA strand extension from the primer oligonucleotides. The oligonucleotide probe is displaced and degraded by the enzymatic action of the Taq polymerase in the next PCR cycle, releasing the reporter from the quencher molecule. In one variation, known as Scorpion®, the probe is covalently linked to the primer.

Reverse Transcription PCR (RT-PCR)

RT-PCR can be used to compare RNA levels in different sample populations, in normal and tumour tissues, with or without drug treatment, to characterize patterns of expression, to discriminate between closely related RNAs, and to analyze RNA structure.

For RT-PCR, the first step is the isolation of RNA from a target sample. The starting material is typically total RNA isolated from human tumours or tumour cell lines, and corresponding normal tissues or cell lines, respectively. RNA can be isolated from a variety of samples, such as tumour samples from breast, lung, colon (e.g., large bowel or small bowel), colorectal, gastric, esophageal, anal, rectal, prostate, brain, liver, kidney, pancreas, spleen, thymus, testis, ovary, uterus, bladder etc., tissues, from primary tumours, or tumour cell lines, and from pooled samples from healthy donors. If the source of RNA is a tumour, RNA can be extracted, for example, from frozen or archived paraffin-embedded and fixed (e.g., formalin-fixed) tissue samples.

The first step in gene expression profiling by RT-PCR is the reverse transcription of the RNA template into cDNA, followed by its exponential amplification in a PCR reaction. The two most commonly used reverse transcriptases are avian myeloblastosis virus reverse transcriptase (AMV-RT) and Moloney murine leukaemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3-5' proofreading endonuclease activity. Thus, TaqMan gPCR typically utilizes the 5' nuclease activity of Taq or Tth polymerase to hydrolyze a hybridization probe bound to its target amplicon, but any enzyme with equivalent 5' nuclease activity can be used.

Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan RT-PCR can be performed using commercially available equipment, such as, for example, ABI PRISM 7700 Sequence Detection System (Perkin-Elmer-Applied Biosystems, Foster City, Calif., USA), or Lightcycler (Roche. Molecular Biochemicals, Mannheim, Germany). In a preferred embodiment, the 5' nuclease procedure is run on a real-time quantitative PCR device such as the ABI PRISM 7700 Sequence Detection System. The system consists of a thermocycler, laser, charge-coupled device (CCD), camera, and computer. The system amplifies samples in a 96-well format on a thermocycler. During amplification, laser-induced fluorescent signal is collected in real-time through fibre optics cables for all 96 wells, and detected at the CCD. The system includes software for running the instrument and for analyzing the data.

5' nuclease assay data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle.

Real-Time Quantitative PCR (qRT-PCR)

A more recent variation of the RT-PCR technique is the real time quantitative PCR, which measures PCR product accumulation through a dual-labeled fluorigenic probe (i.e., TaqMan probe). Real time PCR is compatible both with quantitative competitive PCR and with quantitative comparative PCR. The former uses an internal competitor for each target sequence for normalization, while the latter uses a normalization gene contained within the sample, or a housekeeping gene for RT-PCR. Further details are provided, e.g., by Held et al., Genome Research 6: 986-994 (1996).

Expression levels can be determined using fixed, paraffin-embedded tissues as the RNA source. According to one aspect of the present invention, PCR primers are designed to flank intron sequences present in the gene to be amplified. In this embodiment, the first step in the primer/probe design is the delineation of intron sequences within the genes. This can be done by publicly available software, such as the DNA BLAT software developed by Kent, W. J., Genome Res: 12 (4): 656-64 (2002), or by the BLAST software including its variations. Subsequent steps follow well established methods of PCR primer and probe design.

In order to avoid non-specific signals, it is useful to mask repetitive sequences within the introns when designing the primers and probes. This can be easily accomplished by using the Repeat Masker program available on-line through the Baylor College of Medicine, which screens DNA sequences against a library of repetitive elements and returns a query sequence in which the repetitive elements are masked. The masked sequences can then be used to design primer and probe sequences using any commercially or otherwise publicly available primer/probe design packages, such as Primer Express (Applied Biosystems); MGB assay-by-design (Applied Biosystems); Primer3 (Steve Rozen and Helen J. Skaletsky (2000) Primer3 on the VIMNV for general users and for biologist programmers in: Krawetz 5, Misener S (eds) Bioinformatics Methods and Protocols: Methods in Molecular Biology. Humana Press, Totowa, N.J., pp 365-386).

The most important factors considered in PCR primer design include primer length, melting temperature (Tm), and G/C content, specificity, complementary primer sequences, and 3' end sequence. In general, optimal PCR primers are generally 1730 bases in length, and contain about 20-80%, such as, for example, about 50-60% G+C bases. Melting temperatures between 50 and 80° C., e.g., about 50 to 70° C., are typically preferred. For further guidelines for PCR primer and probe design see, e.g., Dieffenbach, C. W. et al., General Concepts for PCR Primer Design in: PCR Primer, A Laboratory Manual, Cold Spring Harbor Laboratory Press, New York, 1995, pp. 133-155; Innis and Gelfand, Optimization of PCRs in: PCR Protocols, A Guide to Methods and Applications, CRC Press, London, 1994, pp. 5-11; and Plasterer, T. N. Primerselect: Primer and probe design. Methods Mol. Biol. 70: 520-527 (1997), the entire disclosures of which are hereby expressly incorporated by reference.

Microarray Analysis

Differential expression can also be identified, or confirmed using the microarray technique. Thus, the expression profile of GTMs can be measured in either fresh or paraffin-embedded tumour tissue, using microarray technology. In this method, polynucleotide sequences of interest (including cDNAs and oligonucleotides) are plated, or arrayed, on a microchip substrate. The arrayed sequences (i.e., capture probes) are then hybridized with specific polynucleotides from cells or tissues of interest (i.e., targets). Just as in the RT-PCR method, the source of RNA typically is total RNA isolated from human tumours or tumour cell lines, and corresponding normal tissues or cell lines. Thus RNA can be isolated from a variety of primary tumours or tumour cell lines. If the source of RNA is a primary tumour, RNA can be extracted, for example, from frozen or archived formalin fixed paraffin-embedded (FFPE) tissue samples and fixed (e.g., formalin-fixed) tissue samples, which are routinely prepared and preserved in everyday clinical practice.

In a specific embodiment of the microarray technique, PCR amplified inserts of cDNA clones are applied to a substrate. The substrate can include up to 1, 2, 5, 10, 15, 20, 25, 30, 35, 40, 45, 50, or 75 nucleotide sequences. In other aspects, the substrate can include at least 10,000 nucleotide sequences. The microarrayed sequences, immobilized on the microchip, are suitable for hybridization under stringent conditions. As other embodiments, the targets for the microarrays can be at least 50, 100, 200, 400, 500, 1000, or 2000 bases in length; or 50-100, 100-200, 100-500, 100-1000, 100-2000, or 500-5000 bases in length. As further embodiments, the capture probes for the microarrays can be at least 10, 15, 20, 25, 50, 75, 80, or 100 bases in length; or 10-15, 10-20, 10-25, 10-50, 10-75, 10-80, or 20-80 bases in length.

Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual colour fluorescence, separately labeled cDNA probes generated from two sources of RNA are hybridized pairwise to the array. The relative abundance of the transcripts from the two sources corresponding to each specified gene is thus determined simultaneously.

The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., Proc. Natl. Acad. Sci. USA 93 (2): 106-149 (1996)). Microarray analysis can be performed by commercially available equipment, following manufacturer's protocols, such as by using the Affymetrix GenChip technology, Illumina microarray technology or Incyte's microarray technology. The development of microarray methods for large-scale analysis of gene expression makes it possible to search systematically for molecular markers of cancer classification and outcome prediction in a variety of tumour types.

RNA Isolation, Purification, and Amplification

General methods for mRNA extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker, Lab Invest. 56: A67 (1987), and De Sandres et al., BioTechniques 18: 42044 (1995). In particular, RNA isolation can be performed using purification kit, buffer set, and protease from commercial manufacturers, such as Qiagen, according to the manufacturer's instructions. For example, total RNA from cells in culture can be isolated using Qiagen RNeasy mini-columns. Other commercially available RNA isolation kits include MasterPure Complete DNA and RNA Purification Kit (EPICENTRE (D, Madison, Wis.), and Paraffin Block RNA Isolation Kit (Ambion, Inc.). Total RNA from tissue samples can be isolated using RNA Stat-60 (Tel-Test). RNA prepared from tumour can be isolated, for example, by cesium chloride density gradient centrifugation.

The steps of a representative protocol for profiling gene expression using fixed, paraffin-embedded tissues as the RNA source, including mRNA isolation, purification, primer extension and amplification are given in various published journal articles (for example: T. E. Godfrey et al. J. Molec. Diagnostics 2: 84-91 (2000); K. Specht et al., Am. J. Pathol. 158: 419-29 (2001)). Briefly, a representative process starts with cutting about 10 micron thick sections of paraffin-embedded tumour tissue samples. The RNA is then extracted, and protein and DNA are removed. After analysis of the RNA concentration, RNA repair and/or amplification steps may be included, if necessary, and RNA is reverse transcribed using gene specific promoters followed by RT-PCR. Finally, the data are analyzed to identify the best treatment option(s) available to the patient on the basis of the characteristic gene expression pattern identified in the tumour sample examined.

Immunohistochemistry and Proteomics

Immunohistochemistry methods are also suitable for detecting the expression levels of the proliferation markers of the present invention. Thus, antibodies or antisera, preferably polyclonal antisera, and most preferably monoclonal antibodies specific for each marker, are used to detect expression. The antibodies can be detected by direct labeling of the antibodies themselves, for example, with radioactive labels, fluorescent labels, hapten labels such as, biotin, or an enzyme such as horseradish peroxidase or alkaline phosphatase. Alternatively, unlabeled primary antibody is used in conjunction with a labeled secondary antibody, comprising antisera, polyclonal antisera or a monoclonal antibody specific for the primary antibody. Immunohistochemistry protocols and kits are well known in the art and are commercially available.

Proteomics can be used to analyze the polypeptides present in a sample (e.g., tissue, organism, or cell culture) at a certain point of time. In particular, proteomic techniques can be used to assess the global changes of polypeptide expression in a sample (also referred to as expression proteomics). Proteomic analysis typically includes: (1) separation of individual polypeptides in a sample by 2-D gel electrophoresis (2-D PAGE); (2) identification of the individual polypeptides recovered from the gel, e.g., by mass spectrometry or N-terminal sequencing, and (3) analysis of the data using bioinformatics. Proteomics methods are valuable supplements to other methods of gene expression profiling, and can be used, alone or in combination with other methods, to detect the products of the proliferation markers of the present invention.

Hybridization Methods Using Nucleic Acid Probes Selective for a Marker

These methods involve binding the nucleic acid probe to a support, and hybridizing under appropriate conditions with RNA or cDNA derived from the test sample (Sambrook, J., E Fritsch, E. and T Maniatis, Molecular Cloning: A Laboratory Manual 3$^{rd}$. Cold Spring Harbor Laboratory Press: Cold Spring Harbor (2001)). These methods can be applied to GTM derived from a tumour tissue or fluid sample. The RNA or cDNA preparations are typically labeled with a fluorescent or radioactive molecule to enable detection and quantification. In some applications, the hybridizing DNA can be tagged with a branched, fluorescently labeled structure to enhance signal intensity (Nolte, F. S., Branched DNA signal amplification for direct quantitation of nucleic acid sequences in clinical specimens. Adv. Clin. Chem. 33, 201-35 (1998)). Unhybridized label is removed by extensive washing in low salt solutions such as 0.1×SSC, 0.5% SDS before quantifying the amount of hybridization by fluorescence detection or densitometry of gel images. The supports can be solid, such as nylon or nitrocellulose membranes, or consist of microspheres or beads that are hybridized when in liquid suspension. To allow washing and purification, the beads may be magnetic (Haukanes, B-1 and Kvam, C. Application of magnetic beads in bioassays. Bio/Technology 11, 60-63 (1993)) or fluorescently-labeled to enable flow cytometry (see for example: Spiro, A., Lowe, M. and Brown, D., A Bead-Based Method for Multiplexed Identification and Quantitation of DNA Sequences Using Flow Cytometry. Appl. Env. Micro. 66, 4258-4265 (2000)).

A variation of hybridization technology is the QuantiGene Plexe assay (Genospectra, Fremont) which combines a fluorescent bead support with branched DNA signal amplification. Still another variation on hybridization technology is the Quantikine® mRNA assay (R&D Systems, Minneapolis). Methodology is as described in the manufacturer's instructions. Briefly the assay uses oligonucleotide hybridization probes conjugated to Digoxigenin. Hybridization is detected using anti-Digoxigenin antibodies coupled to alkaline phosphatase in colorometric assays.

Additional methods are well known in the art and need not be described further herein.

Enzyme-Linked Immunological Assays (ELISA)

Briefly, in sandwich ELISA assays, a polyclonal or monoclonal antibody against the GTM is bound to a solid support (Crowther, J. R. The ELISA guidebook. Humana Press: New Jersey (2000); Harlow, E. and Lane, D., Using antibodies: a laboratory manual. Cold Spring Harbor Laboratory Press: Cold Spring Harbor (1999)) or suspension beads. Other methods are known in the art and need not be described herein further. Monoclonal antibodies can be hybridoma-derived or selected from phage antibody libraries (Hust M. and Dubel S., Phage display vectors for the in vitro generation of human antibody fragments. Methods Mol Biol. 295:71-96 (2005)). Nonspecific binding sites are blocked with non-target protein preparations and detergents. The capture antibody is then incubated with a preparation of sample or tissue from the patient containing the GTM antigen. The mixture is washed before the antibody/antigen complex is incubated with a second antibody that detects the target GTM. The second antibody is typically conjugated to a fluorescent molecule or other reporter molecule that can either be detected in an enzymatic reaction or with a third antibody conjugated to a reporter (Crowther, Id.). Alternatively, in direct ELISAs, the preparation containing the GTM can be bound to the support or bead and the target antigen detected directly with an antibody-reporter conjugate (Crowther, Id.).

Methods for producing monoclonal antibodies and polyclonal antisera are well known in the art and need not be described herein further.

Immunodetection

The methods can also be used for immunodetection of marker family members in sera or plasma from gastric cancer patients taken before and after surgery to remove the tumour, immunodetection of marker family members in patients with other cancers, including but not limited to, colorectal, pancreatic, ovarian, melanoma, liver, oesophageal, stomach, endometrial, and brain and immunodetection of marker family members in urine and stool from gastric cancer patients.

GTMs can also be detected in tissues or samples using other standard immunodetection techniques such as immunoblotting or immunoprecipitation (Harlow, E. and Lane, D., Using antibodies: a laboratory manual. Cold Spring Harbor Laboratory Press: Cold Spring Harbor (1999)). In immunoblotting, protein preparations from tissue or fluid containing the GTM are electrophoresed through polyacrylamide gels under denaturing or non-denaturing conditions. The proteins are then transferred to a membrane support such as nylon. The GTM is then reacted directly or indirectly with monoclonal or polyclonal antibodies as described for immunohistochemistry. Alternatively, in some preparations, the proteins can be spotted directly onto membranes without prior electrophoretic separation. Signal can be quantified by densitometry.

In immunoprecipitation, a soluble preparation containing the GTM is incubated with a monoclonal or polyclonal antibody against the GTM. The reaction is then incubated with inert beads made of agarose or polyacrylamide with covalently attached protein A or protein G. The protein A or G beads specifically interact with the antibodies forming an immobilized complex of antibody-GTM-antigen bound to the bead. Following washing the bound GTM can be detected and quantified by immunoblotting or ELISA.

Threshold Determination

For tests using GTM, thresholds will be derived that will enable a sample to be called either positive or negative for gastric cancer. These thresholds will be determined by the analysis of cohorts of patients who are being investigated for the presence of gastric cancer. Thresholds may vary for different test applications; for example, thresholds for use of the test in population screening will be determined using cohorts of patients who are largely free of urological symptoms, and these thresholds may be different to those used in tests for patients who are under surveillance for gastric cancer recurrence. A threshold could be selected to provide a practical level of test specificity in the required clinical setting; that is, a specificity that allows reasonable sensitivity without excessive numbers of patients receiving false positive results. This specificity may be within the range of 80-90%. An alternative method to obtain a test threshold is to plot sensitivity against specificity for different test thresholds (ROC curves) then select the point of inflexion of the curve.

As an alternative to single thresholds, the test may use test intervals which provide different degrees of likelihood of presence of disease and which have different clinical consequences associated with them. For example, a test may have three intervals; one associated with a high (e.g. 90%) risk of the presence of gastric cancer, a second associated with a low risk of gastric cancer and a third regarded as being suspicious of disease. The "suspicious" interval could be associated with a recommendation for a repeat test in a defined period of time.

Antibodies to Gastric Cancer Markers

In additional aspects, this invention includes manufacture of antibodies against GTMs. Using methods described herein, novel GTMs can be identified using microarray and/or qRT-PCR methods. Once a putative marker is identified, it can be produced in sufficient amount to be suitable for eliciting an immunological response. In some cases, a full-length GTM can be used, and in others, a peptide fragment of a GTM may be sufficient as an immunogen. The immunogen can be injected into a suitable host (e.g., mouse, rabbit, etc) and if desired, an adjuvant, such as Freund's complete adjuvant or Freund's incomplete adjuvant can be injected to increase the immune response. It can be appreciated that making antibodies is routine in the immunological arts and need not be described herein further. As a result, one can produce antibodies, including monoclonal or phage-display antibodies, against GTMs identified using methods described herein.

In yet further embodiments, antibodies can be made against the protein or the protein core of the tumour markers identified herein or against an oligonucleotide sequence unique to a GTM. Although certain proteins can be glycosylated, variations in the pattern of glycosylation can, in certain circumstances, lead to mis-detection of forms of GTMs that lack usual glycosylation patterns. Thus, in certain aspects of this invention, GTM immunogens can include deglycosylated GTM or deglycosylated GTM fragments. Deglycosylation can be accomplished using one or more glycosidases known in the art. Alternatively, GTM cDNA can be expressed in glycosylation-deficient cell lines, such as prokaryotic cell lines, including *E. coli* and the like.

Vectors can be made having GTM-encoding oligonucleotides therein. Many such vectors can be based on standard vectors known in the art. Vectors can be used to transfect a variety of cell lines to produce GTM-producing cell lines, which can be used to produce desired quantities of GTM for development of specific antibodies or other reagents for detection of GTMs or for standardizing developed assays for GTMs.

Kits

Based on the discoveries of this invention, several types of test kits can be envisioned and produced. First, kits can be made that have a detection device pre-loaded with a detection molecule (or "capture reagent"). In embodiments for detection of GTM mRNA, such devices can comprise a substrate (e.g., glass, silicon, quartz, metal, etc) on which oligonucleotides as capture reagents that hybridize with the mRNA to be detected is bound. In some embodiments, direct detection of mRNA can be accomplished by hybridizing mRNA (labeled with cy3, cy5, radiolabel or other label) to the oligonucleotides on the substrate. In other embodiments, detection of mRNA can be accomplished by first making complementary DNA (cDNA) to the desired mRNA. Then, labeled cDNA can be hybridized to the oligonucleotides on the substrate and detected.

Antibodies can also be used in kits as capture reagents. In some embodiment's, a substrate (e.g., a multiwell plate) can have a specific GTM capture reagent attached thereto. In some embodiments, a kit can have a blocking reagent included. Blocking reagents can be used to reduce non-specific binding. For example, non-specific oligonucleotide binding can be reduced using excess DNA from any convenient source that does not contain GTM oligonucleotides, such as salmon sperm DNA. Non-specific antibody binding can be reduced using an excess of a blocking protein such as serum albumin. It can be appreciated that numerous methods for detecting oligonucleotides and proteins are known in the art, and any strategy that can specifically detect GTM associated molecules can be used and be considered within the scope of this invention.

Antibodies can also be used when bound to s a solid support, for example using an antibody chip, which would allow for the detection of multiple markers with a single chip.

In addition to a substrate, a test kit can comprise capture reagents (such as probes), washing solutions (e.g., SSC, other salts, buffers, detergents and the like), as well as detection moieties (e.g., cy3, cy5, radiolabels, and the like). Kits can also include instructions for use and a package.

Cancer markers can be detected in a sample using any suitable technique, and can include, but are not limited to, oligonucleotide probes, qPCR or antibodies raised against cancer markers.

It will be appreciated that the sample to be tested is not restricted to a sample of the tissue suspected of being a tumour. The marker may be secreted into the serum or other body fluid. Therefore, a sample can include any bodily sample, and includes biopsies, blood, serum, peritoneal washes, cerebrospinal fluid, urine and stool samples.

It will also be appreciate that the present invention is not restricted to the detection of cancer in humans, but is suitable for the detection of cancer in any animal, including, but not limited to dogs, cats, horses, cattle, sheep, deer, pigs and any other animal known to get cancer.

Tests for Gastric Cancer Markers in Body Fluids

In several embodiments, assays for GTM can be desirably carried out on samples obtained from blood, plasma, serum, peritoneal fluid obtained for example using peritoneal washes, or other body fluids, such as urine, lymph, cerebrospinal fluid, gastric fluid or stool samples.

In general, methods for assaying for oligonucleotides, proteins and peptides in these fluids are known in the art. Detection of oligonucleotides can be carried out using hybridization methods such as Northern blots, Southern blots or microarray methods, or qPCR. Methods for detecting proteins include such as enzyme linked immunosorbent assays (ELISA), protein chips having antibodies, suspension beads radioimmunoassay (RIA), Western blotting and lectin binding. However, for purposes of illustration, fluid levels of a GTM can be quantified using a sandwich-type enzyme-linked immunosorbent assay (ELISA). For plasma assays, a 5 uL aliquot of a properly diluted sample or serially diluted standard GTM and 75 uL of peroxidaseconjugated anti-human GTM antibody are added to wells of a microtiter plate. After a 30 minute incubation period at 30° C., the wells are washed with 0.05% Tween 20 in phosphate-buffered saline {PBS) to remove unbound antibody. Bound complexes of GTM and anti-GTM antibody are then incubated with o-phenylendiamine containing $H_2O_2$ for 15 minutes at 30° C. The reaction is stopped by adding 1 M $H_2SO_4$, and the absorbance at 492 nm is measured with a microtiter plate reader.

It can be appreciated that anti-GTM antibodies can be monoclonal antibodies or polyclonal antisera. It can also be appreciated that any other body fluid can be suitably studied.

It is not necessary for a marker to be secreted, in a physiological sense, to be useful. Rather, any mechanism by which a marker protein or gene enters the serum can be effective in producing a detectable, quantifiable level of the marker. Thus, normal secretion of soluble proteins from cells, sloughing of membrane proteins from plasma membranes, secretion of alternatively spliced forms of mRNA or proteins expressed therefrom, cell death (either apoptotic) can produce sufficient levels of the marker to be useful.

There is increasing support for the use of serum markers as tools to diagnose and/or evaluate efficacy of therapy for a variety of cancer types.

Yoshikawa et al., (Cancer Letters, 151: 81-86 (2000) describes tissue inhibitor of matrix metalloproteinase-1 in plasma of patients with gastric cancer.

Rudland et al., (Cancer Research 62: 3417-3427 (2002) describes osteopontin as a metastasis associated protein in human breast cancer.

Buckhaults et al, (Cancer Research 61:6996-7001 (2002) describes certain secreted and cell surface genes expressed in colorectal tumors.

Kim et al., (JAMA 287(13):1671-1679 (2002) describes osteopontin as a potential diagnostic biomarker for ovarian cancer.

Hotte et al., (A J. American Cancer Society 95(3):507-512 (2002) describes plasma osteopontin as a protein detectable in human body fluids and is associated with certain malignancies.

Martin et al, (Prostate Cancer Prostatic Dis. Mar. 9, 2004 (PMID: 15007379) (Abstract) described use of human kallikrein 2, prostate-specific antigen (PSA) and free PSA as markers for detection of prostate cancer.

Hall et al (Laryngoscope 113(1):77-81 (2003) (PMID: 12679418) (Abstract) described predictive value of serum thyroglobulin in thyroid cancer.

Mazzaferri et al., (J. Clin. Endocrinol. Metab. 88(4):1433-1441 (2003) (Abstract) describes thyroglobulin as a potential monitoring method for patients with thyroid carcinoma.

Whitley et al, (Dim Lab. Med. 24(1):29-47 (2004) (Abstract) describes thyroglobulin as a serum marker for thyroid carcinoma.

Kuo et al (Clin. Chim. Acta. 294(1-2):157-168 (2000) (Abstract) describes serum matrix metalloproteinase-2 and -9 in HCP- and HBV-infected patients.

Koopman et al., (Cancer Epidemiol. Biomarkers Prep 13(3): 487-491 (2004) (Abstract) describes osteopontin as a biomarker for pancreatic adenocarcinoma.

Pellegrini et al., (Cancer Immunol. Immunother. 49(7):388-394 (2000) (Abstract) describes measurement of soluble carcinoembryonic antigen and TIMP 1 as markers for preinvasive colorectal cancer.

Melle et al., (Clin. Chem. 53(4), 629-635 (2007) (Abstract) describes HSP27 as a serum marker for pancreatic adenocarcinoma.

Leman et al., (Urology, 69(4) 714-20 (2007) (Abstract) describes EPCA-2 as a serum marker for prostate cancer.

Tsigkou et al., (I Clin Endocrinol Metab, 92(7) 2526-31 (2007) (Abstract) describes total inhibin as a potential serum marker for ovarian cancer.

Marchi et al., (Cancer 112, 1313-1324 (2008) (Abstract) describes ProApolipoprotein AI as a serum marker of brain metastases in lung cancer patients.

Methods

The following general methods were used to evaluate the suitability of various approaches to molecular identification of markers associated with gastric tumors.

Tumor Collection

Gastric tumor samples and non-malignant gastric tissues were collected from surgical specimens resected at Seoul National University Hospital. Diagnosis of gastric cancer was made on the basis of symptoms, physical findings and histological examination of tissues.

RNA Extraction

In some embodiments, expression of genes associated with gastric tumors was analyzed by determining the levels of RNA in samples taken from tumors. Frozen surgical specimens were embedded in OCT medium. 60 micron sections were sliced from the tissue blocks using a microtome, homogenized in a TriReagent:water (3:1) mix, then chloroform extracted. Total RNA was then purified from the aqueous phase using the RNeasy™ procedure (Qiagen). In total, RNA from 58 gastric tumors and 58 non-malignant ("normal") gastric tissue samples were extracted and used in the microarray analysis described below. RNA was also extracted from 16 cancer cell lines and pooled to serve as a reference RNA.

Microarray Slide Preparation

Epoxy coated glass slides were obtained from MWG Biotech AG, Ebersberg, Germany) and were printed with –30,000 50mer oligonucleotides using a Gene Machines microarraying robot, according to the manufacturer's protocol.

RNA Labeling and Hybridization cDNA was transcribed from 10 ug total RNA using Superscript II reverse transcriptase (Invitrogen) in reactions containing 5-(3-aminoallyl)-2' deoxyuridine-5'-triphosphate. The reaction was then de-ionized in a Microcon column before being incubated with Cy3 or Cy5 in bicarbonate buffer for 1 hour at room temperature. Unincorporated dyes were removed using a Qiaquick column (Qiagen) and the sample concentrated to 15 ul in a SpeedVac. Cy3 and Cy5 labeled cDNAs were then mixed with Ambion ULTRAhyb buffer, denatured at 100° C. for 2 minutes and hybridized to the microarray slides in hybridization chambers at 42° C. for 16 hours. The slides were then washed and scanned twice in an Axon 4000A scanner at two power settings to yield primary fluorescence data on gene expression.

Normalization Procedure

To measure the expression of cancer genes in tumors and non-cancerous tissues, median fluorescence intensities detected by Genepix™ software were corrected by subtraction of the local background fluorescence intensities. Spots with a background corrected intensity of less than zero were excluded. To facilitate normalization, intensity ratios and overall spot intensities were log-transformed. Log-transformed intensity ratios were corrected for dye and spatial bias using local regression implemented in the LOCFIT™ package. Log-transformed intensity ratios were regressed simultaneously with respect to overall spot intensity and location. The residuals of the local regression provided the corrected log-fold changes. For quality control, ratios of each normalized microarray were plotted with respect to spot intensity and localization. The plots were subsequently visually inspected for possible remaining artifacts. Additionally, an analysis of variance (ANOVA) model was applied for the detection of pin-tip bias. All results and parameters of the normalization were inserted into a Postgres-database for statistical analysis.

Marker Selection

Microarray gene expression data for each of 29,718 genes was ranked according to the relative intensity of signal for each gene in both tumor and non-malignant tissue. Further analysis was limited to (i) genes encoding secreted proteins (ii) genes with an intensity rank in tumor tissue higher than that observed for the gene (CEACAM5) encoding the existing tumor marker CEA and (iii) genes with no significant expression in blood or vascular tissue, as determined by EST counts in the Unigene database (Wheeler D L et al 2003). Secreted proteins were predicted by identifying transcripts expected to contain an N-terminal signal peptide. Proteins with predicted transmembrane helices that were not in the first 20 N-terminal amino acids [Krogh A. et al 2001] were discarded. Further subcellular localization was predicted using TARGETP [Emanuelsson 0 et al 2000].

Reference numbers (MWG oligo #) for relevant oligonucleotides, and the NCBI mRNA and protein reference sequences of selected GTMs are shown in FIG. 1. FIG. 1 also shows the rank intensity of the selected GTMs in both tumor and nonmalignant tissue. Full DNA sequences of the GTM of this invention are shown herein below.

Quantitative Real-Time PCR

In other embodiments, real-time, or quantitative PCR (qPCR) can be used for absolute or relative quantitation of PCR template copy number. The primer set for MUC17 (Fwd: GAGGTGGTCAGCAGCATTGAC; SEQ ID NO.1; Rev: CCTGGGAAGAGTGGTTTTTAGC; SEQ ID NO.2) was designed using Primer Express V 2.0TM (Applied Biosystems) and amplified product detected using SYBR green labelling. ZG16 was represented by the Assay-on-Demand™ expression assay Hs.00380609_ml (Applied Biosystems) Amplification was carried out on an ABI Prism™ 7000 sequence detection system under standard cycling conditions.

Assays were performed over two 96 well plates with each RNA sample represented by a single cDNA. Up to 45 RNA samples from both gastric tumours and non-malignant gastric tissue was analysed. Each plate contained a reference cDNA standard curve, over a 625-fold concentration range, in duplicate. Analysis consisted of calculating the ΔCT (target gene CT–mean reference cDNA CT). ΔCT is directly proportional to the negative log 2 fold change. Log 2 fold changes relative to the median non-malignant log 2 fold change were then calculated (log 2 fold change–median normal log 2 fold change). These fold changes were then clustered into frequency classes and graphed.

Protein Expression and Antibody Generation

To validate ZG16 at the protein level it was necessary to generate new antibodies against the recombinant protein. The coding region 17-167 of ZG16 was PCR amplified from human cell line cDNA using the forward primer CACCAATGCCATTCAGGCCAGGT; SEQ ID NO.3 and the reverse primer TCAGCATCTGCTGCAGCTA; SEQ ID NO.4. The PCR product was gel purified and cloned into the "Gateway" entry vector "pENTR/dTOPO" from Invitrogen before being sequence to verify correct insert. Using the "Gateway" system ZG16 was then cloned from pENTR/dTOPO into the Invitrogen expression vector pDEST17 containing an N terminal 6×HIS tag. Expression of ZG16 was carried out in BL21-AI *E. coli* cells (Invitrogen), cells were grown at 37° C. on a shaker until they were in mid log phase ($OD_{600}$=0.5) whereby they were induced at a final concentration of 0.2% arabinose and grown for a further 3 hours at 37° C. on a shaker. Cells were harvested by centrifuging at 6000×g for 15 minutes and supernatant discarded. The cells were resuspended in PBS (pH7.0) and lysed by sonication using a Sonics Vibra cell at 60% power. Lysed cells were cleared by centrifuging at 12000×g for 10 minutes and the supernatant was discarded. Cell pellet was washed three times in PBS (pH7.0) buffer containing 0.5% Triton X-100 followed by one wash with PBS (pH7.0). Then, pellet was further washed once using 8M urea in PBS (pH7.0). Each wash step was clarified by centrifuging at 12000×g and supernatant was discarded. The pellet was then solubilised in solubilisation buffer containing 10 mM TRIS (pH18.0), 8M urea, 100 mM NaCl overnight at room temperature. Solubilisation buffer was further centrifuged at 12000×g, filtered through a 0.45 nm membrane and loaded onto a NiSepharose column pre-washed with washing buffer containing PBS (pH7.0), 8M Urea and 20 mM Imidazole. After loading, column was washed with 10 column volumes of washing buffer and solubilised proteins were eluted in washing buffer, supplemented with 500 mM Imidazole. Eluted proteins were desalted into PBS (pH7.0) and 8M urea buffer and then refolded by drop-wise dilution in refolding buffer containing 50 mM Sodium Acetate (pH 4.5), 0.1M NDSB-201, 10% Glycerol, 1 mM/0.1 mM GSH/GSSH. Refolding buffer was clarified by centrifugation at 12000×g and refolded protein was concentrated using Centriprep filters with nominal molecular cut-off of 10 KDa (Millipore). Refolded proteins were buffer exchanged into a buffer containing 100 mM sodium acetate (pH 5.0) supplemented with 10% glycerol using a G25 desalt column and aliquots were stored at −80° C. Coomassie stained 10% SDS PAGE gel and Western blot analysis collectively indicated the presence of a His-tagged protein of 18 KDa at up to 95% purity. The 18 KDa Coomassie stained band was excised and identified by MALDI-TOF/TOF MS/MS to contain ZG16.

Antibodies against ZG16 were obtained by panning a phage display antibody library with the purified ZG16 protein (Antibodies by Design; a division of Morphosys AG, Germany).

Antibody Arrays

Antibody arrays were used to validate the candidate markers. Serum samples were obtained from patients with gastric cancer, colorectal cancer (before and after surgery) and from surgical patients with non-malignant disease. Samples were made available by Dunedin Public Hospital, New. Zealand, and the Christchurch Cancer Society tissue bank, Christchurch, New Zealand. Antibodies against ZG16 and MUC17 that were obtained from either commercial sources or selected from phage libraries (Morphosys) were printed onto glass slides (Schott Nexterion Slide H) using the GeneMachines OmniGrid 100 array robot. Each array was circumscribed with a hydrophobic pen. Slides were then washed in 3×PBS-0.5% Tween 20 (3×PBS-T) before blocking with 50 mM ethanolamine in 50 mM sodium borate buffer, pH8.0 followed by caseinate blocking buffer (3×PBS-T, 1% sodium caseinate). Biotin-labelled serum samples were then added to the slides before incubation overnight at 4° C. Slides were then washed in 3×PBS-T before being air-dried. Bound antibody was then detected using rolling circle amplification (RCA), largely as previously described (Haab B B, Lizardi P M. RCA-enhanced protein detection arrays. Methods Mol Biol. 2006; 328:15-29). Briefly, the slides were incubated with anti-biotin antibodies that had been conjugated with an oligonucleotide primer (5'-CCT GGT GCT CAA ATT TCA GTT CTG C-3'; SEQ ID NO.5). A circular DNA template was then hybridised to the slides at 37° C. for 30 mins in a humidified sealed chamber, before the slides were washed in decreasing concentrations of PBS-T (3×PBS-0.05% Tween 20, 1×PBS-0.05% Tween 20 and 0.1×PBS-0.05% Tween 20) and dried. The template was then extended using phi29 at 30° C. for 3 hrs before the slides were washed and dried by centrifugation. The amplified template was then detected using homologous fluorescently labeled probes. Slides were scanned with an Axon 4000A scanner and signal measured with the GenePix Pro 6.1.0.4 software.

Cy5 fluorescence intensity was adjusted using quantile normalization, using the normalizeBetweenArrays function from the limma (Smith, 2005) package, for R (the R package for statistical computing (R Development Core). Quantile normalization adjusts the values of the intensities so that the distribution of intensities is the same for each block (each block corresponding to a separate sample), by setting the quantiles of the intensities from different blocks to the same value. The rank of each intensity value does not change during this procedure, only the relative magnitude of the intensities. The assumption is that the underlying probability distribution function describing the range of antigen concentrations is the same for all samples. This procedure improved the average correlation of signals between blocks across all samples and also when considering reference-only blocks, which indicates an improvement in the quality of the data. Genepix-flagged spots were removed before taking the median across replicates to obtain, normalized intensities for each antibody.

Thus, we have identified three genes and/or proteins that are useful for developing reagents, devices and kits for detecting and evaluating gastric cancer. One or more markers of gastric cancer can be used, either singly or in combination to provide a reliable molecular test for gastric cancer.

EXAMPLES

The examples described herein are for purposes of illustrating embodiments of the invention. Other embodiments, methods and types of analyses are within the scope of persons of ordinary skill in the molecular diagnostic arts and need not be described in detail hereon. Other embodiments within the scope of the art are considered to be part of this invention.

Example 1

Identification of Markers for Gastric Malignancy

Markers were selected using the gene expression data obtained from gastric tumors and non-malignant samples. The following criteria was used for marker selection: (i) the presence of a signal sequence characteristic of a secreted protein (ii) the microarray signal intensity ranking in tumor tissue and (iii) the levels of corresponding ESTs in blood or vascular tissues. The use of these criteria enabled the identification of secreted markers that are abundantly expressed in tumor tissue but likely to have a low background in serum, blood or plasma. FIG. 1 depicts a table that shows the three markers for gastric malignancy selected using the above criteria, MUC5AC, MUCI7 and ZG16. FIG. 1 includes the symbol for the gene ("symbol"), the MWG oligo number, the NCBI mRNA reference sequence number, the protein reference sequence number, the rank intensity of the gene on the arrays derived using tumor tissue, and the rank intensity of the gene on the arrays derived using nonmalignant tissue. All three GTMs had a higher expression (intensity) rank than CEACAM5, the gene that encodes the existing gastric cancer marker CEA. The lowest expressing rank possible was 29,718. Examination of the ranking also shows that the expression of these GTMs in tumor tissue was comparable to non-malignant tissue, indicating that the genes had not been strongly down-regulated during carcinogenesis. Unigene EST counts (Wheeler et al, 2003) for the three GTMs in blood and vascular tissue were all zero.

Example 2 qRT-PCR Analysis

The abundance and identity of the GTMs ZG16 and MUC17 was confirmed in tumor tissue using the more sensitive and accurate gene expression quantification technique, qPCR. Up to 45 gastric tumor samples and an equal number of nonmalignant gastric tissue samples from the same patients were analysed by RT-qPCR using the primers and probes described in the methods section. Expression of these genes was quantified using the number of PCR cycles required to reach a threshold level of product amplification (Ct).

qPCR analysis confirmed the array data: both markers were readily detected in tumor tissue by qPCR and there was no evidence for a significant decrease in expression in tumor tissue compared to non-malignant tissue. The abundance of these RNAs in tumor tissue compared to non-malignant tissue is illustrated by the histograms in FIG. 2*a-b*.

Example 3

Detection of Gastric Tumor Marker Proteins in Serum

In certain embodiments, detection of GTM proteins can be accomplished using antibodies directed against either the entire protein, a fragment of the protein (peptide) or the protein core. Methods for detecting and quantifying expression of proteins and peptides are known in the art and can include methods relying on specific antibodies raised against the protein or peptide. Monoclonal antibodies and polyclonal antisera can be made using methods that are well known in the art and need not be described herein further.

To detect the GTMs in serum, antibodies against the GTMs were printed onto glass slides using Gene Machine OmniGrid™ robotics. Each antibody was repeated 8 times on the array. Serum samples from 33 gastric cancer patients and 41 controls were then labeled with biotin before being incubated with the antibody slides. Bound proteins were detected with anti-biotin antibodies and the signal amplified using rolling circle amplification (RCA) and fluorescent labeling. The amount of bound protein was quantified using an Axon 4000a scanner and the Genepix 6.1.0.4 software. The characteristics of the patients are shown in FIG. 2.

The fluorescent signal from each antibody on the array was normalized and the median signal for the 8 replicates expressed in arbitrary fluorescent units. Box plots illustrating the data spread are shown in FIG. 3. The median signal for MUC 17 was 18,836AU for gastric cancer patients and 16,130 for the control group. These medians were significantly different (p=0.007). Significant differences between the medians were observed for two phage display ZG16 antibodies (5902 and 5905) obtained from MorphoSys. The median signal for ZG16_5902 in gastric cancer patient samples was 2139AU compared to 1837AU for controls; the median ZG16_5905 signal in patients was 3063AU compared to 1675AU for controls. The median signal between patients and controls for both ZG16_5902 and ZG16_5905 were significantly different (p=0.05 and p=0.005, respectively).

This data demonstrates that MUC17 and ZG16 are present at significantly higher levels in the serum of gastric cancer patients than controls. Further differentiation between patient and control groups will be achieved by refinement of the immunological testing procedure, the identification of antibodies with greater specificity for the target antigens and the use of combinations of markers.

Example 8

Cells Transfected with GTM-Containing Vectors

In still further embodiments, cells are provided that can express GTMs, GTM fragments or peptide markers. Both prokaryotic and eukaryotic cells can be so used. For example, *E. coli* (a prokaryotic cell) can be use to produce large quantities of GTMs lacking in mature glycosylation (if the particular GTM normally is glycosylated). COS cells, 293 cells and a variety of other eukaryotic cells can be used to produce GTMs that are glycosylated, or have proper folding and therefore, three-dimensional structure of the native form of the GTM protein. Methods for transfecting such cells are known in the art and need not be described further herein.

Example 9

Kits

Based on the discoveries of this invention, several types of test kits can be produced. First, kits can be made that have a detection device pre-loaded with a detection molecule (or "capture reagent"). In embodiments for detection of GTM mRNA, such devices can comprise a substrate (e.g., glass, silicon, quartz, metal, etc) on which oligonucleotides as capture reagents that hybridize with the mRNA to be detected. In some embodiments, direct detection of mRNA can be accomplished by hybridizing mRNA (labeled with cy3, cy5, radiolabel or other label) to the oligonucleotides on the substrate. In other embodiments, detection of mRNA can be accomplished by first making complementary DNA (cDNA) to the desired mRNA. Then, labeled cDNA can be hybridized to the oligonucleotides on the substrate and detected.

Regardless of the detection method employed, comparison of test GTM expression with a standard measure of expression is desirable. For example, RNA expression can be standardized to total cellular DNA, to expression of constitutively expressed RNAs (for example, ribosomal RNA) onto other relatively constant markers.

Antibodies can also be used in kits as capture reagents. In some embodiments, a substrate (e.g., a multiwell plate) can have a specific GTM capture reagent attached thereto. In some embodiments, a kit can have a blocking reagent included. Blocking reagents can be used to reduce non-specific binding. For example, non-specific oligonucleotide binding can be reduced using excess DNA from any convenient source that does not contain GTM oligonucleotides, such as salmon sperm DNA. Non-specific antibody binding can be reduced using an excess of a blocking protein such as serum albumin. It can be appreciated that numerous methods for detecting oligonucleotides and proteins are known in the art, and any strategy that can specifically detect GTM associated molecules can be used and be considered within the scope of this invention.

In embodiments relying upon antibody detection, GTM proteins or peptides can be expressed on a per cell basis, or on the basis of total cellular, tissue, or fluid protein, fluid volume, tissue mass (weight). Additionally, GTM in serum can be expressed on the basis of a relatively high-abundance serum protein such as albumin.

In addition to a substrate, a test kit can comprise capture reagents (such as probes), washing solutions (e.g., SSC, other salts, buffers, detergents and the like), as well as detection moieties (e.g., cy3, cy5, radiolabels, and the like). Kits can also include instructions for use and a package.

Although this invention is described with reference to specific embodiments thereof, it can be appreciated that other embodiments involving the use of the disclosed markers can be used without departing from the scope of this invention.

INDUSTRIAL APPLICABILITY

Methods for detecting GTM family members include detection of nucleic acids using microarray and/or real time PCR methods and detection of proteins and peptides. The compositions and methods of this invention are useful in the manufacture of diagnostic devices and kits, diagnosis of disease, evaluating efficacy of therapy, and for producing reagents suitable for measuring expression of GTM family members in biological samples.

REFERENCES

Emanuelsson O, Nielsen H, Brunak S, von Heijne G. Predicting subcellular localization of proteins based on their N-terminal amino acid sequence. J Mol Biol. 2000 Jul. 21; 300(4):1005-16.

Krogh A, Larsson B, von Heijne G, Sonnhammer E L. Predicting transmembrane protein topology with a hidden Markov model: application to complete genomes. J Mol Biol. 2001 Jan. 19; 305(3):567-80.

Smyth, G. K. (2005). Limma: linear models for microarray data. In: 'Bioinformatics and Computational Biology Solutions using R and Bioconductor'. R. Gentleman, V. Carey, S. Dudoit, R. Irizarry, W. Huber (eds), Springer, New York, pages 397-420.

R Development Core Team (2008). R: A language and environment for statistical computing. R Foundation for Statistical Computing, Vienna, Austria. ISBN 3-900051-07-0.

Wheeler D L, et al. Database Resources of the National Center for Biotechnology. Nucl Acids Res 31:28-33; 2003.

The invention claimed is:

1. A method for detecting gastric cancer, comprising:

(i) providing a sample of serum from a human being suspected of having gastric cancer;

(ii) providing samples of serum from a group of control human beings not having gastric cancer;

(iii) detecting the levels of zymogen granule protein 16 ("ZG16") and mucin 17 ("MUC17") in said sample in step (i) using rolling circle amplification;

(iv) detecting the levels of a gastric cancer markers ("GTM") zymogen granule protein 16 ("ZG16") and MUC17 in said sample in step (ii) using rolling circle amplification, and normalizing expression data;

(v) normalizing expression data obtained in step (iii) using quintile normalization; and (vi) comparing the expression of ZG16 and MUC17 in said sample in step (i) with the expression of ZG16 and MUC17 in step (ii), wherein an increase of normalized ZG16 expression and an increase of normalized MUC17 expression in the sample of serum from said human being compared to the normalized expression of ZG16 and MUC17 in a group of control samples of serum is indicative of gastric cancer.

2. The method of claim 1, wherein said method further comprises detecting the expression level of mucin 5AC ("MUC5AC").

3. The method of claim 1, wherein the one or more further GTM family member is selected from MUC5AC, carboxypeptidase N, polypeptide 2, 83 kDa chain ("CPN2"), matrix metalloproteinase 12 ("MMP12"), inhibin ("INHBA"), insulin-like growth factor 7 ("IGFBP7"), gamma-glutamyl hydrolase ("GGH"), leucine proline enriched proteoglycan ("LEPRE1"), cystatin S ("CST4"), secreted frizzled-related protein 4 ("SFRP4"), asporin ("ASPN"), cell growth regulator with EF hand domain 1 ("CGREF1"), kallikrein 10 (KLK10), tissue inhibitor of metalloproteinase 1 ("TIMP1"), secreted acidic cysteine-rich protein ("SPARC"), transforming growth factor, 13-induced ("TGFBI"), EGF-containing fibulin-like extracellular matrix protein 2 ("EFEMP2"), lumican ("LUM"), stannin ("SNN"), secreted phosphoprotein 1 ("SPP1"), chondroitin sulfate proteoglycan 2 ("CSPG2"), N-acylsphingosine amidohydrolase ("ASAH1"), serine protease 11 ("PRSS11"), secreted frizzled-related protein 2 ("SFRP2"), phospholipase A2, group XIIB ("PLA2G12B"), spondin 2, extracellular matrix protein ("SPON2"), olfactomedin 1 ("OLFM1"), thrombospondin repeat containing 1 ("TSRC1"), thrombospondin 2 ("THBS2"), adlican, cystatin SA ("CST2"), cystatin SN ("CST1"), lysyl oxidase-like enzyme 2 ("LOXL2"), thyroglobulin ("TG"), transforming growth factor beta1 ("TGFB1"), serine or cysteine proteinase inhibitor Clade H, member 1 ("SERPINH1"), serine or cysteine proteinase inhibitor Clade B, member 5 ("SERPINB5"), matrix metalloproteinase 2 ("MMP2"), proprotein convertase subtilisin/kexin type 5 ("PCSK5"), hyaluronan glycoprotein link protein 4 ("HAPLN4"), CA19-9, CA72-4, pepsinogen and CEA.

4. The method of claim 1, wherein the one or more further GTM family member is selected from the group consisting of cystatin SN, serpinH1 and serpinB5.

5. The method of claim 1, wherein said step of detecting is carried out by detecting the levels of a GTM mRNA.

6. The method of claim 1, wherein said step of detecting is carried out by detecting the levels of a GTM cDNA.

7. The method of claim 1, wherein said step of detecting is carried out using an oligonucleotide complementary to at least a portion of a ZG16 cDNA.

8. The method of claim 1, wherein said step of detecting is carried out using qRT-PCR method using a forward primer and a reverse primer.

9. The method of claim 1, wherein said step of detecting is carried out by detecting the levels of a ZG16 protein or peptide.

10. The method of claim 9 wherein said step of detecting is carried out using an antibody directed against said ZG16.

11. The method of claim 9, wherein said step of detecting is carried out using a sandwich-type immunoassay method, or using an antibody chip.

12. The method of claim 9, wherein said antibody is a monoclonal antibody.

13. The method of claim 9, wherein said antibody is a polyclonal antiserum.

* * * * *